US008034329B2

(12) United States Patent
Colter et al.

(10) Patent No.: US 8,034,329 B2
(45) Date of Patent: Oct. 11, 2011

(54) REPAIR AND REGENERATION OF RENAL TISSUE USING HUMAN UMBILICAL CORD TISSUE-DERIVED CELLS

(75) Inventors: David C. Colter, Hamilton, NJ (US); Anna Gosiewska, Skillman, NJ (US)

(73) Assignee: Advanced Technologies And Regenerative Medicine, LLC, Raynham, MA (US)

( * ) Notice: Subject to any disclaimer, the term of this patent is extended or adjusted under 35 U.S.C. 154(b) by 139 days.

(21) Appl. No.: 12/245,571

(22) Filed: Oct. 3, 2008

(65) Prior Publication Data

US 2009/0092653 A1    Apr. 9, 2009

Related U.S. Application Data

(60) Provisional application No. 60/977,775, filed on Oct. 5, 2007.

(51) Int. Cl.
*A01N 65/00* (2009.01)
(52) U.S. Cl. .................................................. 424/93.1
(58) Field of Classification Search .................. None
See application file for complete search history.

(56) References Cited

U.S. PATENT DOCUMENTS

| | | |
|---|---|---|
| 4,352,883 A | 10/1982 | Lim |
| 4,882,162 A | 11/1989 | Ikada et al. |
| 4,963,489 A | 10/1990 | Naughton et al. |
| 5,004,681 A | 4/1991 | Boyse et al. |
| 5,192,553 A | 3/1993 | Boyse et al. |
| 5,286,632 A | 2/1994 | Jones |
| 5,320,962 A | 6/1994 | Stiles et al. |
| 5,342,761 A | 8/1994 | MacLeod |
| 5,437,994 A | 8/1995 | Emerson et al. |
| 5,443,950 A | 8/1995 | Naughton et al. |
| 5,486,359 A | 1/1996 | Caplan et al. |
| 5,580,777 A | 12/1996 | Bernard et al. |
| 5,589,376 A | 12/1996 | Anderson et al. |
| 5,670,483 A | 9/1997 | Zhang et al. |
| 5,677,181 A | 10/1997 | Parish |
| 5,698,518 A | 12/1997 | Carson et al. |
| 5,707,643 A | 1/1998 | Ogura et al. |
| 5,736,516 A | 4/1998 | Louis |
| 5,811,094 A | 9/1998 | Caplan et al. |
| 5,827,735 A | 10/1998 | Young et al. |
| 5,834,308 A | 11/1998 | Peck et al. |
| 5,840,580 A | 11/1998 | Terstappen et al. |
| 5,842,477 A | 12/1998 | Naughton et al. |
| 5,843,780 A | 12/1998 | Thomson |
| 5,869,079 A | 2/1999 | Wong et al. |
| 5,902,598 A | 5/1999 | Chen et al. |
| 5,902,741 A | 5/1999 | Purchio et al. |
| 5,906,934 A | 5/1999 | Grande et al. |
| 5,919,702 A | 7/1999 | Purchio et al. |
| 5,942,225 A | 8/1999 | Bruder et al. |
| 5,955,343 A | 9/1999 | Holmes et al. |
| 5,962,325 A | 10/1999 | Naughton et al. |
| 5,994,094 A | 11/1999 | Hötten et al. |
| 6,001,647 A | 12/1999 | Peck et al. |
| 6,022,743 A | 2/2000 | Naughton et al. |
| 6,140,039 A | 10/2000 | Naughton et al. |
| 6,171,610 B1 | 1/2001 | Vacanti et al. |
| 6,200,606 B1 | 3/2001 | Peterson et al. |
| 6,200,806 B1 | 3/2001 | Thomson |
| 6,214,369 B1 | 4/2001 | Grande et al. |
| 6,251,090 B1 | 6/2001 | Avery et al. |
| 6,291,240 B1 | 9/2001 | Mansbridge et al. |
| 6,323,188 B1 | 11/2001 | Weissman |
| 6,326,201 B1 | 12/2001 | Fung et al. |
| 6,331,313 B1 | 12/2001 | Wong et al. |
| 6,355,239 B1 | 3/2002 | Bruder et al. |
| 6,355,699 B1 | 3/2002 | Vyakarnam et al. |
| 6,372,494 B1 | 4/2002 | Naughton et al. |
| 6,375,972 B1 | 4/2002 | Guo et al. |
| 6,387,367 B1 | 5/2002 | Davis-Sproul et al. |
| 6,391,297 B1 | 5/2002 | Halvorsen |
| 6,429,013 B1 | 8/2002 | Halvorsen et al. |
| 6,436,704 B1 | 8/2002 | Roberts et al. |
| 6,444,205 B2 | 9/2002 | Dinsmore et al. |
| 6,497,875 B1 | 12/2002 | Sorrell et al. |
| 6,511,511 B1 | 1/2003 | Slivka et al. |
| 6,528,245 B2 | 3/2003 | Sanchez-Ramos et al. |
| 6,534,084 B1 | 3/2003 | Vyakarnam et al. |
| 6,555,374 B1 | 4/2003 | Gimble et al. |
| 6,599,323 B2 | 7/2003 | Melican et al. |
| 6,610,535 B1 | 8/2003 | Lu et al. |
| 6,638,765 B1 | 10/2003 | Rosenberg |
| 6,673,606 B1 | 1/2004 | Tennekoon et al. |
| 6,680,198 B1 | 1/2004 | Snyder et al. |
| 6,686,198 B1 | 2/2004 | Melton et al. |
| 6,703,017 B1 | 3/2004 | Peck et al. |
| 6,916,655 B2 | 7/2005 | Yasumoto et al. |
| 7,413,734 B2 | 8/2008 | Mistry et al. |
| 7,510,873 B2 | 3/2009 | Mistry et al. |
| 7,524,489 B2 | 4/2009 | Messina et al. |
| 7,560,276 B2 | 7/2009 | Harmon et al. |
| 7,875,272 B2 | 1/2011 | Messina et al. |
| 7,875,273 B2 | 1/2011 | Messina et al. |

(Continued)

FOREIGN PATENT DOCUMENTS

CN    1407088    2/2003

(Continued)

OTHER PUBLICATIONS

Abbas, A.K. et al., *Cellular and Molecular Immunology*, 5th Ed., 2003, Saunders, Philadelphia, p. 171.

(Continued)

*Primary Examiner* — Q. Janice Li
(74) *Attorney, Agent, or Firm* — Patton Boggs LLP

(57) ABSTRACT

Methods for treating a patient having a disease or damage to at least one kidney are provided. The methods comprise administering cells obtained from human umbilical cord tissue, or administering pharmaceutical compositions comprising such cells or prepared from such cells. When administered, the cells promote and support the repair and regeneration of the diseased or damaged kidney tissue in the patient. Pharmaceutical compositions for use in the inventive methods, as well as kits for practicing the methods are also provided.

14 Claims, 8 Drawing Sheets

U.S. PATENT DOCUMENTS

| | | |
|---|---|---|
| 2001/0024824 A1 | 9/2001 | Moss et al. |
| 2001/0031256 A1 | 10/2001 | Edge |
| 2001/0046489 A1 | 11/2001 | Habener et al. |
| 2002/0022676 A1 | 2/2002 | He et al. |
| 2002/0028510 A1 | 3/2002 | Sanberg et al. |
| 2002/0062151 A1 | 5/2002 | Altman et al. |
| 2002/0064519 A1 | 5/2002 | Bruder et al. |
| 2002/0081725 A1 | 6/2002 | Tsang et al. |
| 2002/0098584 A1 | 7/2002 | Palmer et al. |
| 2002/0119565 A1 | 8/2002 | Clarke et al. |
| 2002/0123141 A1 | 9/2002 | Hariri |
| 2002/0150986 A1 | 10/2002 | Lau |
| 2002/0151056 A1 | 10/2002 | Sasai et al. |
| 2002/0160471 A1 | 10/2002 | Kisiday et al. |
| 2002/0160510 A1 | 10/2002 | Hariri |
| 2002/0164307 A1 | 11/2002 | Habener et al. |
| 2002/0164791 A1 | 11/2002 | Van Der Kooy et al. |
| 2002/0168763 A1 | 11/2002 | Yan et al. |
| 2002/0182728 A1 | 12/2002 | Ramiya et al. |
| 2002/0187550 A1 | 12/2002 | Dinsmore et al. |
| 2002/0192816 A1 | 12/2002 | Roberts et al. |
| 2003/0003574 A1 | 1/2003 | Toma et al. |
| 2003/0007954 A1 | 1/2003 | Naughton et al. |
| 2003/0022369 A1 | 1/2003 | Fillmore et al. |
| 2003/0031657 A1 | 2/2003 | Habener et al. |
| 2003/0032178 A1 | 2/2003 | Williams et al. |
| 2003/0032179 A1 | 2/2003 | Hariri |
| 2003/0032183 A1 | 2/2003 | Sheridan |
| 2003/0049837 A1 | 3/2003 | Weiss et al. |
| 2003/0059939 A1 | 3/2003 | Page et al. |
| 2003/0082155 A1 | 5/2003 | Habener et al. |
| 2003/0082160 A1 | 5/2003 | Yu et al. |
| 2003/0096409 A1 | 5/2003 | Yasumoto et al. |
| 2003/0104997 A1 | 6/2003 | Black et al. |
| 2003/0109036 A1 | 6/2003 | Wu |
| 2003/0113910 A1 | 6/2003 | Levanduski |
| 2003/0118566 A1 | 6/2003 | Neuman et al. |
| 2003/0124721 A1 | 7/2003 | Cheatham et al. |
| 2003/0138948 A1 | 7/2003 | Fisk et al. |
| 2003/0138951 A1 | 7/2003 | Yin |
| 2003/0148513 A1 | 8/2003 | Sugaya et al. |
| 2003/0161818 A1 | 8/2003 | Weiss et al. |
| 2003/0162290 A1 | 8/2003 | Inoue et al. |
| 2003/0170215 A1 | 9/2003 | Tsang et al. |
| 2003/0175963 A1 | 9/2003 | Rosenberg |
| 2003/0180269 A1 | 9/2003 | Hariri |
| 2003/0186439 A1 | 10/2003 | Nakauchi et al. |
| 2003/0199447 A1 | 10/2003 | Goldman et al. |
| 2003/0203484 A1 | 10/2003 | Black et al. |
| 2003/0207450 A1 | 11/2003 | Young et al. |
| 2003/0211087 A1 | 11/2003 | Goldman |
| 2003/0211603 A1 | 11/2003 | Earp et al. |
| 2003/0211605 A1 | 11/2003 | Lee et al. |
| 2003/0212024 A1 | 11/2003 | Keating et al. |
| 2003/0219894 A1 | 11/2003 | Seino et al. |
| 2003/0228295 A1 | 12/2003 | Svendsen |
| 2003/0235563 A1 | 12/2003 | Strom et al. |
| 2003/0235909 A1 | 12/2003 | Hariri et al. |
| 2004/0005704 A1 | 1/2004 | Csete et al. |
| 2004/0009593 A1 | 1/2004 | Keirstead et al. |
| 2004/0014206 A1 | 1/2004 | Robl et al. |
| 2004/0014210 A1 | 1/2004 | Jessell et al. |
| 2004/0014211 A1 | 1/2004 | Ogle et al. |
| 2004/0014662 A1 | 1/2004 | Lindquist et al. |
| 2004/0029269 A1 | 2/2004 | Goldman et al. |
| 2004/0033597 A1 | 2/2004 | Toma et al. |
| 2004/0037818 A1 | 2/2004 | Brand et al. |
| 2004/0048372 A1 | 3/2004 | Hariri |
| 2004/0058412 A1 | 3/2004 | Ho et al. |
| 2004/0063202 A1 | 4/2004 | Petersen et al. |
| 2004/0072344 A1 | 4/2004 | Inoue et al. |
| 2004/0136967 A1 | 7/2004 | Weiss et al. |
| 2005/0019865 A1 | 1/2005 | Kihm et al. |
| 2005/0032209 A1 | 2/2005 | Messina et al. |
| 2005/0037491 A1 | 2/2005 | Mistry et al. |
| 2005/0054098 A1 | 3/2005 | Mistry et al. |
| 2005/0058629 A1 | 3/2005 | Harmon et al. |
| 2005/0058630 A1 | 3/2005 | Harris et al. |
| 2005/0058631 A1 | 3/2005 | Kihm et al. |
| 2005/0074435 A1 | 4/2005 | Casper et al. |
| 2005/0148074 A1 | 7/2005 | Davies et al. |
| 2005/0249731 A1 | 11/2005 | Aslan et al. |
| 2006/0153815 A1 | 7/2006 | Seyda et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0171930 A1 | 8/2006 | Seyda et al. |
| 2006/0188983 A1 | 8/2006 | Harris et al. |
| 2006/0223177 A1 | 10/2006 | Harris et al. |
| 2006/0233765 A1 | 10/2006 | Messina et al. |
| 2006/0233766 A1 | 10/2006 | Messina et al. |
| 2006/0234376 A1 | 10/2006 | Mistry et al. |
| 2007/0009494 A1 | 1/2007 | Mistry et al. |
| 2007/0014771 A1 | 1/2007 | Mistry et al. |
| 2007/0036767 A1 | 2/2007 | Mistry et al. |
| 2007/0141700 A1 | 6/2007 | Harmon |
| 2007/0160588 A1 | 7/2007 | Kihm |
| 2007/0264269 A1 | 11/2007 | Harmon et al. |
| 2007/0275362 A1 | 11/2007 | Edinger et al. |
| 2008/0112939 A1 | 5/2008 | Colter et al. |
| 2008/0145934 A1 | 6/2008 | Harris et al. |
| 2008/0166328 A1 | 7/2008 | Harmon et al. |
| 2008/0305148 A1 | 12/2008 | Fu |
| 2009/0166178 A1 | 7/2009 | Harmon et al. |
| 2009/0169597 A1 | 7/2009 | Brown et al. |
| 2010/0158877 A1 | 6/2010 | Colter et al. |
| 2010/0158880 A1 | 6/2010 | Seyda et al. |
| 2010/0159025 A1 | 6/2010 | Kramer et al. |
| 2010/0159588 A1 | 6/2010 | Harmon et al. |
| 2010/0210013 A1 | 8/2010 | Mistry et al. |
| 2010/0215714 A1 | 8/2010 | Messina et al. |
| 2010/0247499 A1 | 9/2010 | Kihm et al. |
| 2010/0260843 A1 | 10/2010 | Messina et al. |

FOREIGN PATENT DOCUMENTS

| | | |
|---|---|---|
| JP | 2003-235549 | 8/2003 |
| JP | 2004-254682 | 9/2004 |
| WO | WO 90/11354 | 10/1990 |
| WO | WO 92/03917 | 3/1992 |
| WO | WO 93/04169 | 3/1993 |
| WO | WO 94/25584 | 11/1994 |
| WO | WO 95/17911 | 7/1995 |
| WO | WO 95/23216 | 8/1995 |
| WO | WO 96/01316 | 1/1996 |
| WO | WO 96/05309 | 2/1996 |
| WO | WO 98/17791 | 4/1998 |
| WO | WO 98/51317 | 11/1998 |
| WO | WO 99/03973 | 1/1999 |
| WO | WO 00/09666 | 2/2000 |
| WO | WO 00/73421 | 12/2000 |
| WO | WO 01/11011 | 2/2001 |
| WO | WO 01/19379 | 3/2001 |
| WO | WO 01/34775 | 5/2001 |
| WO | WO 02/46373 | 6/2002 |
| WO | WO 02/059278 | 8/2002 |
| WO | WO 02/062969 | 8/2002 |
| WO | WO 02/063962 | 8/2002 |
| WO | WO 02/064748 | 8/2002 |
| WO | WO 02/064755 | 8/2002 |
| WO | WO 02/086107 | 10/2002 |
| WO | WO 03/023020 | 3/2003 |
| WO | WO 03/025149 | 3/2003 |
| WO | WO 03/029443 | 4/2003 |
| WO | WO 03/029445 | 4/2003 |
| WO | WO 03/039489 | 5/2003 |
| WO | WO 03/042405 | 5/2003 |
| WO | WO 03/048336 | 6/2003 |
| WO | WO 03/055992 | 7/2003 |
| WO | WO 03/064601 | 8/2003 |
| WO | WO 03/066832 | 8/2003 |
| WO | WO 03/068937 | 8/2003 |
| WO | WO 03/070922 | 8/2003 |
| WO | WO 03/072728 | 9/2003 |
| WO | WO 03/080822 | 10/2003 |

| | | |
|---|---|---|
| WO | WO 03/087333 | 10/2003 |
| WO | WO 03/087392 | 10/2003 |
| WO | WO 03/089619 | 10/2003 |
| WO | WO 03/100038 | 12/2003 |
| WO | WO 03/102134 | 12/2003 |
| WO | WO 03/102151 | 12/2003 |
| WO | WO 03/104442 | 12/2003 |
| WO | WO 2004/011012 | 2/2004 |
| WO | WO 2004/011621 | 2/2004 |
| WO | WO 2004/016747 | 2/2004 |
| WO | WO 2004/023100 | 3/2004 |
| WO | WO 2004/072273 | 8/2004 |
| WO | WO 2005/001076 | 1/2005 |
| WO | WO 2005/001077 | 1/2005 |
| WO | WO 2005/001078 | 1/2005 |
| WO | WO 2005/001079 | 1/2005 |
| WO | WO 2005/001080 | 1/2005 |
| WO | WO 2005/003334 | 1/2005 |
| WO | WO 2005/021738 | 3/2005 |
| WO | WO 2005/038012 | 4/2005 |
| WO | WO 2005/042703 | 5/2005 |
| WO | WO 2006/055685 | 5/2006 |
| WO | WO 2006/071773 | 7/2006 |
| WO | WO 2006/071777 | 7/2006 |
| WO | WO 2006/071778 | 7/2006 |
| WO | WO 2006/071802 | 7/2006 |
| WO | WO 2006071794 A2 * | 7/2006 |
| WO | WO 2006/105152 | 10/2006 |
| WO | WO 2006/117237 | 11/2006 |
| WO | WO 2007/070870 | 6/2007 |
| WO | WO 2007/073552 | 6/2007 |
| WO | WO 2007/076522 | 7/2007 |
| WO | WO 2007/108003 | 9/2007 |
| WO | WO 2008/045498 | 4/2008 |
| WO | WO 2008/060541 | 5/2008 |
| WO | WO 2008/085221 | 7/2008 |
| WO | WO 2009/046335 | 4/2009 |
| WO | WO 2009/085860 | 7/2009 |
| WO | WO 2010/071862 | 6/2010 |
| WO | WO 2010/071863 | 6/2010 |
| WO | WO 2010/071864 | 6/2010 |
| WO | WO 2010/080364 | 7/2010 |
| WO | WO 2010/111663 | 9/2010 |

OTHER PUBLICATIONS

Anseth, K.S. et al., "In Situ Forming Degradable Networks And Their Application In Tissue Engineering and Drug Delivery," *J. of Controlled Release*, 2002; 78:199-209.

Brown, J.A. et al., "Blockade Of Programmed Death-1 Ligands on Dendritic Cells Enhances T Cell Activation and Cytokine Production," *J. Immunology*, 2003; 170:1257-1266.

Cheng, A., et al. "Nitric Oxide Acts In a Positive Feedback Loop With BDNF To Regulate Neural Progenitor Cell Proliferation and Differentiation In The Mammalian Brain," *Dev. Biol.*, 2003; 258:319-333.

Coumans, B. et al., "Lymphoid Cell Apoptosis Induced By Trophoblastic Cells: A Model Of Active Foeto-Placental Tolerance," *J. of Immunological Methods*, 1999; 224:185-196.

Haug et al.,"A Phase I Trial of Immunosuppression with Anti-ICAM-1 (CD54) mAb in Renal Allograft Recipients," *Transplantation*, 1993; 55:766-772.

Kelly, K.J., and Molitoris, B.A., "Acute Renal Failure in the New Millennium: Time to Consider Combination Therapy," *Semin Nephrol.*, 2000; 20(1):4-19.

U.S. Appl. No. 08/430,768, filed Apr. 27, 1995, Peterson et al.

Li, A. et al., "IL-8 Directly Enhanced Endothelial Cell Survival, Proliferation, And Matrix Metalloproteinases Production And Regulated Angiogenesis," *J. Immunol.*, 2003; 170(6):3369-3376.

Lieberthal and Nigam, "Acute Renal Failure II Experimental Models of Acute Renal Failure: Imperfect but Indispensable," *Am. J. Physiol. Renal Physicol.*, 2000; 278:F1-F12.

Messina, D.J., et al., "Comparison Of Pure And Mixed Populations Of Human Fetal-Derived Neural Progenitors Transplanted Into Intact Adult Rat Brain," *Exper. Neurol.*, 2003; 184:816-829.

Morigi, M. et al., "Mesenchymal Stem Cells are Renotropic, Helping to Repair the Kidney and Improve Function in Acute Renal Failure," *J. Am. Soc. Nephrol.*, 2004; 15(7):1794-1804.

Rosen, E.M. et al., "HGF/SF In Angiogenesis," *Ciba Found. Symp.*, 1997; 212:215-229.

Salcedo, R. et al., "Human Endothelial Cells Express CCR2 And Respond To MCP-1: Direct Role Of MCP-1 In Angiogenesis And Tumor Progression," *Blood*, 2000; 96(1):34-40.

Tögel et al., "Administered Mesenchymal Stem Cells Protect Against Ischemic Acute Renal Failure through Differentiation-Independent Mechanisms," *Am. J. Physiol. Renal Physicol*, 2000, 289:F31-F42.

Tusher, V.G. et al., "Significance Analysis Of Microarrays Applied To The Ionizing Radiation Response," *PNAS*, 2001; 98(9):5116-5121.

Wang, D. et al., "Synthesis and Characterization Of A Novel Degradable Phosphate-Containing Hydrogel," *Biomaterials*, 2003; 24:3969-3980.

In the U.S. Patent and Trademark Office, Non-Final Office Action in re: U.S. Appl. No. 10/877,012, dated Sep. 24, 2007, 18 pages.

In the U.S. Patent and Trademark Office, Final Office Action in re: U.S. Appl. No. 10/877,012, dated Mar. 15, 2007, 13 pages.

In the U.S. Patent and Trademark Office, Non-Final Office Action in re: U.S. Appl. No. 10/877,012, dated Jul. 18, 2006, 26 pages.

In the U.S. Patent and Trademark Office, Non-Final Office Action in re: U.S. Appl. No. 11/315,897, dated Jun. 13, 2008, 12 pages.

In the U.S. Patent and Trademark Office, Non-Final Office Action in re: U.S. Appl. No. 10/877,446, dated Feb. 28, 2008, 19 pages.

In the U.S. Patent and Trademark Office, Final Office Action in re: U.S. Appl. No. 10/877,446, dated Jun. 27, 2007, 24 pages.

In the U.S. Patent and Trademark Office, Non-Final Office Action in re: U.S. Appl. No. 10/877,446, dated Nov. 20, 2006, 24 pages.

In the U.S. Patent and Trademark Office, Non-Final Office Action in re: U.S. Appl. No. 10/877,269, dated Jan. 17, 2008, 10 pages.

In the U.S. Patent and Trademark Office, Final Office Action in re: U.S. Appl. No. 10/877,269, dated Aug. 14, 2007, 6 pages.

In the U.S. Patent and Trademark Office, Non-Final Office Action in re: U.S. Appl. No. 10/877,269, dated May 3, 2007, 12 pages.

In the U.S. Patent and Trademark Office, Non-Final Office Action in re: U.S. Appl. No. 11/315,898, dated Feb. 13, 2008, 12 pages.

In the U.S. Patent and Trademark Office, Final Office Action in re: U.S. Appl. No. 11/315,943, dated Aug. 20, 2008, 7 pages.

In the U.S. Patent and Trademark Office, Non-Final Office Action in re: U.S. Appl. No. 11/315,943, dated Feb. 12, 2008, 11 pages.

In the U.S. Patent and Trademark Office, Non-Final Office Action in re: U.S. Appl. No. 10/877,445, dated Jul. 11, 2008, 12 pages.

In the U.S. Patent and Trademark Office, Non-Final Office Action in re: U.S. Appl. No. 10/877,445, dated Mar. 19, 2008, 12 pages.

In the U.S. Patent and Trademark Office, Final Office Action in re: U.S. Appl. No. 10/877,445, dated Nov. 5, 2007, 17 pages.

In the U.S. Patent and Trademark Office, Non-Final Office Action in re: U.S. Appl. No. 10/877,445, dated May 17, 2007, 20 pages.

In the U.S. Patent and Trademark Office, Final Office Action in re: U.S. Appl. No. 10/877,445, dated Sep. 11, 2006, 30 pages.

In the U.S. Patent and Trademark Office, Non-Final Office Action in re: U.S. Appl. No. 10/877,445, dated Nov. 21, 2005, 17 pages.

In the U. S. Patent and Trademark Office, Non-Final Office Action in re: U.S. Appl. No. 11/322,372 dated Sep. 3, 2008, 13 pages.

In the U.S. Patent and Trademark Office, Non-Final Office Action in re: U.S. Appl. No. 10/877,541, dated Jul. 25, 2007, 13 pages.

In the U.S. Patent and Trademark Office, Advisory Office Action in re: U.S. Appl. No. 10/877,541, dated Apr. 18, 2007, 4 pages.

In the U.S. Patent and Trademark Office, Final Office Action in re: U.S. Appl. No. 10/877,541, dated Jan. 10, 2007, 19 pages.

In the U.S. Patent and Trademark Office, Non-Final Office Action in re: U.S. Appl. No. 10/877,541, dated Feb. 22, 2006, 13 pages.

In the U.S. Patent and Trademark Office, Advisory Office Action in re: U.S. Appl. No. 11/317,574, dated Jun. 4, 2008, 3 pages.

In the U.S. Patent and Trademark Office, Final Office Action in re: U.S. Appl. No. 11/317,574, dated Mar. 5, 2008, 10 pages.

In the U.S. Patent and Trademark Office, Final Office Action in re: U.S. Appl. No. 11/317,574, dated Aug. 10, 2007, 14 pages.

In the U.S. Patent and Trademark Office, Non-Final Office Action in re: U.S. Appl. No. 10/877,009 dated Jan. 9, 2008, 12 pages.

In the U.S. Patent and Trademark Office, Final Office Action in re: U.S. Appl. No. 10/877,009, dated Jul. 25, 2007, 17 pages.

In the U.S. Patent and Trademark Office, Non-Final Office Action in re: U.S. Appl. No. 10/877,009, dated Nov. 21, 2006, 15 pages.

In the U.S. Patent and Trademark Office, Non-Final Office Action in re: U.S. Appl. No. 10/876,998, dated Jun. 25, 2008, 9 pages.
In the U.S. Patent and Trademark Office, Final Office Action in re: U.S. Appl. No. 10/876,998, dated Feb. 27, 2008, 18 pages.
In the U.S. Patent and Trademark Office, Non-Final Office Action in re: U.S. Appl. No. 10/876,998, dated Jul. 13, 2007, 30 pages.
In the U.S. Patent and Trademark Office, Final Office Action in re: U.S. Appl. No. 10/876,998, dated Oct. 18, 2006, 29 pages.
In the U.S. Patent and Trademark Office, Non-Final Office Action in re: U.S. Appl. No. 10/876,998, dated Mar. 30, 2006, 24 pages.
In the U.S. Patent and Trademark Office, Non-Final Office Action in re: U.S. Appl. No. 11/321,863, dated Aug. 19, 2008, 15 pages.
In the U.S. Patent and Trademark Office, Non-Final Office Action in re: U.S. Appl. No. 11/322,003, dated Jun. 2, 2008, 14 pages.
In the U.S. Patent and Trademark Office, Non-Final Office Action in re: U.S. Appl. No. 11/321,864, dated Apr. 21, 2008, 7 pages.
In the U.S. Patent and Trademark Office, Final Office Action in re: U.S. Appl. No. 11/315,969, dated May 19, 2008, 9 pages.
In the U.S. Patent and Trademark Office, Non-Final Office Action in re: U.S. Appl. No. 11/315,969, dated Nov. 1, 2007, 12 pages.
In the U.S. Patent and Trademark Office, Final Office Action in re: U.S. Appl. No. 11/297,778, dated Apr. 11, 2008, 9 pages.
In the U.S. Patent and Trademark Office, Non-Final Office Action in re: U.S. Appl. No. 11/297,778, dated Feb. 22, 2007, 8 pages.
In the U.S. Patent and Trademark Office, Final Office Action in re: U.S. Appl. No. 11/304,091, dated Apr. 11, 2008, 11 pages.
In the U.S. Patent and Trademark Office, Non-Final Office Action in re: U.S. Appl. No. 11/304,091, dated Feb. 23, 2007, 9 pages.
In the U. S. Patent and Trademark Office, Final Office Action in re: U.S. Appl. No. 11/315,898, dated Sep. 16, 2008, 8 pages.
In the U. S. Patent and Trademark Office, Non-Final Office Action, in re: U.S. Appl. No. 11/297,156, dated Oct. 10, 2008, 11 pages.
In the U. S. Patent and Trademark Office, Non-Final Office Action in re: U.S. Appl. No. 11/317,574, dated Sep. 30, 2008, 23 pages.
In the U. S. Patent and Trademark Office, Non-Final Office Action in re: U.S. Appl. No. 11/315,969, dated Dec. 23, 2008, 11 pages.
In the U. S. Patent and Trademark Office, Non-Final Office Action in re: U.S. Appl. No. 10/951,357, dated Nov. 26, 2008, 19 pages.
In the U. S. Patent and Trademark Office, Non-Final Office Action in re: U.S. Appl. No. 11/321,864, dated Jan. 8, 2009, 10 pages.
In the U. S. Patent and Trademark Office, Final Office Action in re: U.S. Appl. No. 11/321,863, dated Feb. 12, 2009, 15 pages.
In the U. S. Patent and Trademark Office, Non-Final Office Action, in re: U.S. Appl. No. 11/315,943, dated Feb. 20, 2009, 9 pages.
In the U. S. Patent and Trademark Office, Non-Final Office Action in re: U.S. Appl. No. 10/877,445, dated Mar. 19, 2009, 15 pages.
In the U. S. Patent and Trademark Office, Non-Final Office Action in re: U.S. Appl. No. 11/481,481, dated Mar. 20, 2009, 12 pages.
In the U. S. Patent and Trademark Office, Final Office Action in re: U.S. Appl. No. 11/315,897, dated Mar. 20, 2009, 13 pages.
In the U. S. Patent and Trademark Office, Non-Final Office Action in re: U.S. Appl. No. 11/481,480, dated Mar. 20, 2009, 13 pages.
In the U. S. Patent and Trademark Office, Final Office Action in re: U.S. Appl. No. 11/322,003 dated Feb. 13, 2009, 17 pages.
In the U. S. Patent and Trademark Office, Final Office Action in re: U.S. Appl. No. 10/876,998 dated Feb. 13, 2009, 10 pages.
In the U. S. Patent and Trademark Office, Final Office Action in re: U.S. Appl. No. 11/322,372 dated Feb. 13, 2009, 14 pages.
In the U. S. Patent and Trademark Office, Non-Final Office Action in re: Application No. 11/315,898 dated Feb. 18, 2009, 10 pages.
In the U. S. Patent and Trademark Office, Non-Final Office Action in re: U.S. Appl. No. 11/304,091 dated Feb. 27, 2009, 11 pages.
In the U. S. Patent and Trademark Office, Non-Final Office Action in re: U.S. Appl. No. 11/481,456 dated Apr. 16, 2009, 14 pages.
In the U. S. Patent and Trademark Office, Non-Final Office Action in re: U.S. Appl. No. 11/317,574 dated Apr. 29, 2009, 21 pages.
In the U. S. Patent and Trademark Office, Advisory Action in re: U.S. Appl. No. 11/315,969 dated Sep. 29, 2009, 8 pages.
In the U. S. Patent and Trademark Office, Advisory Action in re: U.S. Appl. No. 11/322,372 dated May 12, 2009, 10 pages.
In the U. S. Patent and Trademark Office, Non-Final Office Action in re: U.S. Appl. No. 10/877,446 dated Jun. 12, 2009, 16 pages.

In the U. S. Patent and Trademark Office, Final Office Action in re: U.S. Appl. No. 11/322,372 dated Aug. 6, 2009, 12 pages.
In the U. S. Patent and Trademark Office, Final Office Action in re: U.S. Appl. No. 11/617,346 dated Aug. 11, 2009, 12 pages.
In the U. S. Patent and Trademark Office, Final Office Action in re: U.S. Appl. No. 11/481,456 dated Oct. 9, 2009, 11 pages.
In the U. S. Patent and Trademark Office, Final Office Action in re: U.S. Appl. No. 10/877,445 dated Aug. 25, 2009, 18 pages.
In the U. S. Patent and Trademark Office, Final Office Action in re: U.S. Appl. No. 11/321,863 dated Aug. 7, 2009, 11 pages.
In the U. S. Patent and Trademark Office, Final Office Action in re: U.S. Appl. No. 11/321,864 dated Aug. 17, 2009, 13 pages.
In the U. S. Patent and Trademark Office, Final Office Action in re: U.S. Appl. No. 11/315,969 dated May 13, 2009, 11 pages.
In the U. S. Patent and Trademark Office, Non-Final Office Action in re: U.S. Appl. No. 11/317,574 dated Dec. 28, 2009, 26 pages.
In the U. S. Patent and Trademark Office, Non-Final Office Action in re: U.S. Appl. No. 11/321,863 dated Jan. 7, 2010, 13 pages.
In the U. S. Patent and Trademark Office, Non-Final Office Action in re: U.S. Appl. No. 11/321,864 dated Jan. 27, 2010, 12 pages.
In the U. S. Patent and Trademark Office, Non-Final Office Action in re: U.S. Appl. No. 11/315,969 dated Jan. 27, 2010, 12 pages.
In the U. S. Patent and Trademark Office, Non-Final Office Action in re: U.S. Appl. No. 11/315,943 dated Feb. 19, 2010, 13 pages.
In the U. S. Patent and Trademark Office, Final Office Action in re: U.S. Appl. No. 11/316,104 dated Mar. 24, 2010, 12 pages.
In the U. S. Patent and Trademark Office, Non-Final Office Action in re: U.S. Appl. No. 11/481,456 dated May 14, 2010, 9 pages.
In the U. S. Patent and Trademark Office, Non-Final Office Action in re: U.S. Appl. No. 11/481,481 dated May 13, 2010, 9 pages.
In the U. S. Patent and Trademark Office, Final Office Action in re: U.S. Appl. No. 11/315,897 dated May 14, 2010, 13 pages.
In the U. S. Patent and Trademark Office, Non-Final Office Action in re: U.S. Appl. No. 11/481,480 dated May 17, 2010, 10 pages.
In the U. S. Patent and Trademark Office, Final Office Action in re: U.S. Appl. No. 10/877,445 dated Jul. 8, 2010, 20 pages.
In the U. S. Patent and Trademark Office, Final Office Action in re: U.S. Appl. No. 10/876,998 dated Aug. 3, 2010, 14 pages.
In the U. S. Patent and Trademark Office, Non-Final Office Action in re: U.S. Appl. No. 11/321,863 dated Aug. 17, 2010, 15 pages.
In the U. S. Patent and Trademark Office, Final Office Action in re: U.S. Appl. No. 11/617,346 dated Aug. 20, 2010, 12 pages.
In the U. S. Patent and Trademark Office, Final Office Action in re: U.S. Appl. No. 11/321,864 dated Aug. 31, 2010, 7 pages.
In the U. S. Patent and Trademark Office, Final Office Action in re: U.S. Appl. No. 11/315,969 dated Aug. 31, 2010, 6 pages.
In the U. S. Patent and Trademark Office, Final Office Action in re: U.S. Appl. No. 11/322,372 dated Aug. 31, 2010, 11 pages.
In the U. S. Patent and Trademark Office, Non-Final Office Action in re: U.S. Appl. No. 11/316,104 dated Sep. 21, 2010, 13 pages.
In the U. S. Patent and Trademark Office, Final Office Action in re: U.S. Appl. No. 11/317,574 dated Oct. 6, 2010, 16 pages.
In the U. S. Patent and Trademark Office, Non-Final Office Action in re: U.S. Appl. No. 12/054,718 dated Sep. 29, 2010, 18 pages.
In the U. S. Patent and Trademark Office, Non-Final Office Action in re: U.S. Appl. No. 11/322,372 dated Jan. 21, 2010, 10 pages.
In the U. S. Patent and Trademark Office, Final Office Action in re: U.S. Appl. No. 11/481,481 dated Sep. 18, 2009, 11 pages.
In the U. S. Patent and Trademark Office, Advisory Action in re: U.S. Appl. No. 11/315,897 dated Jun. 30, 2009, 3 pages.
In the U. S. Patent and Trademark Office, Non-Final Action in re: U.S. Appl. No. 11/315,897 dated Sep. 2, 2009, 12 pages.
In the U. S. Patent and Trademark Office, Final Action in re: U.S. Appl. No. 11/481,480 dated Sep. 17, 2009, 12 pages.
In the U. S. Patent and Trademark Office, Final Action in re: U.S. Appl. No. 10/877,446 dated Jun. 4, 2010, 17 pages.
In the U. S. Patent and Trademark Office, Final Action in re: U.S. Appl. No. 11/617,346 dated Apr. 15, 2010, 7 pages.
In the U. S. Patent and Trademark Office, Non-Final Action in re: U.S. Appl. No. 11/316,104 dated Oct. 31, 2008, 15 pages.
In the U. S. Patent and Trademark Office, Final Action in re: U.S. Appl. No. 10/876,998 dated May 27, 2009, 14 pages.

In the U. S. Patent and Trademark Office, Non-Final Action in re: U.S. Appl. No. 10/876,998 dated Nov. 24, 2009, 7 pages.
In the U. S. Patent and Trademark Office, Final Action in re: U.S. Appl. No. 11/322,003 dated Feb. 13, 2009, 17 pages.
In the U. S. Patent and Trademark Office, Non-Final Office Action in re: U.S. Appl. No. 12/337,439 dated Jan. 6, 2011, 11 pages.
In the U. S. Patent and Trademark Office, Non-Final Action in re: U.S. Appl. No. 10/876,998 dated Feb. 1, 2011, 11 pages.
In the U. S. Patent and Trademark Office, Non-Final Action in re: U.S. Appl. No. 11/481,456 dated Feb. 3, 2011, 10 pages.
In the U. S. Patent and Trademark Office, Non-Final Action in re: U.S. Appl. No. 11/481,481 dated Feb. 3, 2011, 10 pages.
In the U. S. Patent and Trademark Office, Non-Final Action in re: U.S. Appl. No. 12/389,305 dated Feb. 8, 2011, 14 pages.
In the U. S. Patent and Trademark Office, Non-Final Action in re: U.S. Appl. No. 11/481,480 dated Feb. 3, 2011, 10 pages.
Aboody, K.S. et al., "Neural Stem Cells Display Extensive Tropism for Pathology In Adult Brain: Evidence From Intracranial Gliomase," *PNAS*, 2000; 97(23):12846-12851.
Agbulut, O. et al., "Comparison of Human Skeletal Myoblasts and Bone Marrow-Derived CD133+ Progenitors for the Repair of Infarcted Myocardium," *Journal of the American College of Cardiology*, 2004; 44(2):458-463.
Age-Related Eye Disease Study Research Group, "A Randomized, Placebo-Controlled, Clinical Trial of High-Dose Supplementation With Vitamins C And E, Beta Carotene, and Zinc For Age-Related Macular Degeneration And Vision Loss," AREDS Report No. 8 *Arch.*, Ophthalmol. 2001;119(10):1417-1436.
Aggarwal et al., "Human Mesenchymal Stem Cells Modulate Allogeneic Immune Cell Responses," *Blood*, 2005; 105(4):1815-1822.
Aldskogius, H. et al., "Strategies For Repair Of the Deafferented Spinal Cord," *Brain Res. Rev.*, 2002; 40:301-308.
Alini, M. et al., "A Biological Approach to Treating Disc Degeneration: Not for Today, But Maybe for Tomorrow," Eur. Spine J., 2002; 11 (Supp. 2 ): S215-220.
Allcock, H.R. et al., "Synthesis Of Poly[(Amino Acid Alkyl Ester)Phosphazenes]1-3," *Macromolecules*, 1977; 10(4):824-830.
Altman, G.H. et al., "Advanced Bioreactor With Controlled Application of Multi-Dimensional Strain for Tissue Engineering," *J. Biomech. Eng.*, 2002; 124:742-749.
Altman, R.D. et al., "Radiographic Assessment Of Progression in Osteoarthritis," *Arthritis & Rheum.*, 1987; 30(11):1214-1225.
Armulik, A. et al., "Endothelial/Pericyte Interactions," *Circ. Res.*, 2005; 97:512-523.
Aston, J. E., et al., "Repair of Articular Surfaces by Allografts of Articular and Growth-Plate Cartilage," *Journal of Bone and Joint Surgery*, 1986; 68-B(1):29-35.
Auda-Boucher, G. et al., "Staging of the Commitment Of Murine Cardiac Cell Progenitors," *Dev. Bio.*, 2000; 225(1):214-225.
Avital, I. et al., "Isolation, Characterization, and Transplantation of Bone Marrow-Derived Hepatocyte Stem Cells," *Biochem. & Biophys. Res. Comm.*, 2001; 288:156-164.
Azizi, S.A. et al., "Engraftment and Migration Of Human Bone Marrow Stromal Cells Implanted In The Brains of Albino Rats—Similarities to Astrocyte Grafts," *Proc. Natl. Acad. Sci. USA*, 1998; 95:3908-3913.
Bai, M., et al, "Dimerization of the Extracellular Calcium-sensing Receptor (CaR) on the Cell Surface of CaR-Transfected HEK293 Cells," *J. Biol Chem.*, 1998; 273(36): 23605-23610.
Baker, K.A. et al., "Intrastriatal And Intranigral Grafting Of hNT Neurons in The 6-OHDA Rat Model of Parkinson's Disease," *Exper. Neurol.*, 2000; 162:350-360.
Bakhshi, et al. "Mesenchymal stem cells from the Wharton's jelly of umbilical cord segments provide stromal support for the maintenance of cord blood hematopoietic stem cells during long-term ex vivo culture", Transfusion, 2008; 48: 2638-2644.
Balis, F. et al., "Central Nervous System Pharmacology Of Antileukemic Drugs," *Am. J. of Pediatric Hematol. Oncol.*, 1989; 11(1):74-86.
Balkema, G.W. et al., "Impaired Visual Thresholds in Hypopigmented Animals," *Visual Neuroscience*, 1991; 6:577-585.

Bao, Z.Z. et al., "Regulation Of Chamber-Specific Gene Expression In The Developing Heart by IrX 4," *Science*, 1999; 283(5405):1161-1164 (Abstract 1 page).
Barberi, T. et al., "Neural Subtype Specification Of Fertilization And Nuclear Transfer Embryonic Stem Cells and Application In Parkinsonian Mice," *Nature Biotechnology*, 2003; 21(10):1200-1207.
Beck, R.W. et al., "A Clinical Comparison Of Visual Field Testing With A New Automated Perimeter, The Humphrey Field Analyzer, And The Goldmann Perimeter," *Ophthalmology*, 1985; 92(1):77-82.
Bennett et al., "A Peripheral Mononeuropathy in Rate that Produces Disorders of Pain Sensation Like Those Seen in Man," Pain, 1988; 33:87-107.
Bergers, G. et al., "The Role of Pericytes in Blood-Vessel Formation And Maintenance," *Neuro-Oncology*, 2005; 7:452-464.
Bhindi, R. et al., "Rat Models Of Mycocardial Infarction," *Thromb Haemost*, 2006; 96:602-610.
Björklund, L.M. et al., "Embryonic Stem Cells Develop Into Functional Dopaminergic Neurons After Transplantation In A Parkinson Rat Model," *PNAS*, 2002; 99(4):2344-2349.
Blakemore et al., "Modelling Large Areas of Demyelination in the Rat Reveals the Potential and Possible Limitations of Transplanted Glial Cells for Remyelination in the CNS," *GLIA*, 2002; 38:155-168.
Bradley, B.A., "The Role of HLA Matching in Transplantation," *Immunol. Lett.*, 1991; 29:55-59.
Brodsky, S.V., "Coagulation, Fibrinolysis And Angiogenesis: New Insights From Knockout Mice," *Exp. Nephrol.*, 2002; 10:299-306.
Brooks, P., "Inflammation As an Important Feature Of Osteoarthritis," *Bull. World Health Org.*, 2003; 81(9):689-690.
Bruder et al., "Mesenchymal Stem Cell Surface Antigen SB-10 Corresponds to Activated Leukocyte Cell Adhesion Molecule and Is Involved in Osteogenic Differentiation," *Journal of Bone and Mineral Research*, 1998; 13(4):655-663.
Bunge et al., "The Role of the Schwann Cell in Trophic Support and Regeneration," Journal of Neurology, 1994; 241:536.
Burnstein, R.M. et al., "Differentiation And Migration Of Long Term Expanded Human Neural Progenitors In A Partial Lesion Model of Parkinson's Disease," *Intern. J. of Biochem. & Cell Biology*, 2004; 36:702-713.
Bussolati et al., "Isolation of Renal Progenitor Cells from Adult Human Kidney," *American Journal of Pathology*, 2005; 166(2):545-555.
Caballero, S. et al., "The Many Possible Roles of Stem Cells in Age-Related Macular Degeneration," *Graefe's Arch. Clin. Exp. Ophthalmol.*, 2004; 242:85-90.
Campbell, I.K. et al., "Human Articular Cartilage And Chondrocytes Produce Hemopoietic Colony-Stimulating Factors In Culture in Response To IL-1," *J. of Immun.*, 1991; 147(4):1238-1246.
Can et al., "Concise Review: Human Umbilical Cord Stroma with Regard to the Source of Fetus-Derived Stem Cells," Stem Cells, 2007; 25:2886-2895.
Cao, Q. et al., "Stem Cell Repair of Central Nervous System Injury," *J. of Neuroscience Res.*, 2002; 68:501-510.
Caplan, A.I. et al., "Mesenchymal Stem Cells: Building Blocks for Molecular Medicine In The 21st Century," *Trends in Molecular Med.*, 2001; 7(6):259-264.
Carter, D. et al., "Characterization of MSC Potential to Treat GVHD Using Molecular Markers Linked to MSC-Mediated Immunosuppression In Vitro," *Blood*, 2005; 106(11) part 2, Abstract No. 4322, 160B.
"Cell Lysis, p. 2" http://www.piercenet.com/objects/view.cfm?type=Page&ID=1904ED25-8FA4-475C-8068-C2EB13D5F4E7; accessed Aug. 7, 2008.
Chagraoui, J. et al., "Fetal Liver Stroma Consists Of Cells In Epithelial-To-Mesenchymal Transition," *Blood*, 2003; 101(8):2973-2982.
Chen, D. et al. "Differential Roles for Bone Morphogenic Protein (BMP) Receptor Type IB and IA in Differentiation And Specification Of Mesenchymal Precursor Cells To Osteoblast and Adipocyte Lineages," *J. Cell Biol.*, 1998; 142(1):295-305.
Chen, H. et al., "The Effect of Hypothermia on Transient Middle Cerebral Artery Occlusion in the Rat," *J. Cereb. Blood Flow Metab.*, 1992; 12(4):621-628.

Chen, J. et al., "Intravenous Administration of Human Umbilical cord Blood Reduces Behavioral Deficits After Stroke in Rats," *Stroke*, 2001; 32:2682-2688.

Chen, J. et al., "Therapeutic Benefit of Intravenous Administration of Bone Marrow Stromal Cells after Cerebral Ischemia in Rats," *Stroke*, 2001; 32(4):1005-1011.

Chujo, T. et al., "Effects of Growth Differentiation Factor-5 on the Intervertebral Disc-In Vitro Bovine Study and In Vivo Rabbit Disc Degeneration Model Study," Spine, 2006; 31: 2909-2917.

Constantini, S. et al., "The Effects of Methylprednisolone And The Ganglioside GM1 On Acute Spinal Cord Injury in Rats," *J. Neurosurg.*, 1994; 80(1):97-111.

D'Cruz, P.M. et al., "Mutation Of the Receptor Tyrosine Kinase Gene Mertk In The Retinal Dystrophic RCS Rat," *Hum. Mol. Genet.*, 2000; 9(4):645-651.

Daley, G.Q. et al., "Realistic Prospects for Stem Cell Therapeutics," *Hematol.*, 2003; 398-418.

Danon, D. et al., "Macrophage Treatment Of Pressure Sores in Paraplegia," *J. Wound Care*, 1998; 7(6):281-283.

Danon, D. et al., "Treatment Of Human Ulcers by Application Of Macrophages Prepared From A Blood Unit," *Exp. Gerontol.*, 1997; 32(6):633-641.

Dawson, T.M. et al., "Neuroprotective And Neurorestorative Strategies for Parkinson's Disease," *Nat. Neurosci.*, 2002; 5 Suppl.:1058-1061.

del Monte, F. et al., "Improvement In Survival And Cardiac Metabolism After Gene Transfer Of Sarcoplasmic Reticulum Ca $^{2+}$-ATPase In A Rat Model Of Heart Failure," *Circulation*, 2001;104:1424-1429.

Diao et al, "Human Umbilical Cord Mesenchymal Stem Cells: Osteogenesis In Vivo as Seed Cells for Bone Tissue Engineering," *J. BioMed Mater Res.*, 2009; 91A:123-131.

Dickinson, A.M. et al., "Non-HLA Immunogenetics in Hematopoietic Stem Cell Transplantation," *Curr. Opin. Immunol.*, 2005; 17(5):517-525.

Dimri, G.P. et al., "A Biomarker That Identifies Senescent Human Cells In Culture And In Aging Skin In Vivo," *Proc. Natl. Acad. Sci. USA*, 1995; 92:9363-9367.

Domb, A. et al., "Degradable Polymers For Site-Specific Drug Delivery," *Polymers for Advanced Technologies*, 1992; 3:279-292.

Doshi, S.N. et al., "Evolving Role Of Tissue Factor and Its Pathway Inhibitor," *Critical Care Med.*, 2002; 30(5):S241-S250.

Doyle, J., "Spiraling Complexity, Robustness, And Fragility In Biology," http://www.cds.caltech.edu/~doyle/CmplxNets/Bio1.pdf, available online Feb. 28, 2004.

Draper et al., "Surface Antigens of Human Embryonic Stem Cells: Changes Upon Differentiation in Culture," J. Anat., 2002; 200:249-258.

Dutton, R, et al., "Precursor Cells in the Subventricular Zone of the Adult Mouse Are Actively Inhibited from Differentiating into Neurons," *Dev Neurosci*, 2000; 22:96-105.

Du, Y. et al., "Functional Reconstruction Of Rabbit Corneal Epithelium By Human Limbal Cells Cultured On Amniotic Membrane," *Molecular Vision*, 2003; 9:635-643.

Dykens, J. et al., "Photoreceptor Preservation In The S334ter Model Of Retinitis Pigmentosa By A Novel Estradiol Analog", *Biochemical Pharmacology*, 2004; 68: 1971-1984.

Eagle, H., "The Specific Amino Acid Requirements Of A Mammalian Cell (Strain L) In Tissue Culture," *J. Biol. Chem.*, 1955; 214:839-852.

Eblenkamp, M. et al., "Umbilical Cord Stromal Cells (UCSC). Cells Featuring Osteogenic Differentiation Potential," *Der Orthopade*, Dec. 2004; 33:1338-1345 (English abstract on p. 1339).

Edelstein, M. L. et al., "Gene Therapy Clinical Trials Worldwide 1989-2004—An Overview," *J. Gene Med.*, 2004; 6(6):597-602.

Edlund, H., "Pancreatic Organogenesis—Developmental Mechanisms And Implications For Therapy," *Nat. Rev. Genet.*, 2002; 3:524-532.

Efrat, S. et al., "Cell Replacement Therapy For Type 1 Diabetes," *Trends in Molecular Medicine*, 2002; 8(7):334-339.

Ehtesham, M. et al., "Induction Of Glioblastoma Apoptosis Using Neural Stem Cell-Mediated Delivery Of Tumor Necrosis Factor-Related Apoptosis-Inducing Ligand," *Cancer Res.*, 2002; 62:7170-7174.

Ehtesham, M. et al., "The Use Of Interleukin 12-Secreting Neural Stem Cells For The Treatment Of Intracranial Glioma," *Cancer Res.*, 2002; 5657-5663.

Eisenhofer, G.E. et al., "Tyrosinase: A Developmentally Specific Major Determinant Of Peripheral Dopamine," *FASEB J.*, 2003; 17:1248-1255.

Ende, N. et al., "Parkinson's Disease Mice And Human Umbilical Cord Blood," *J. Med.*, 2002; 33(1-4):173-180.

Engstad, C.S. et al., "The Effect of Soluble β-1,3-Glucan And Lipopolysaccharide On Cytokine Production and Coagulation Activation In Whole Blood," *Int. Immunopharmacol.*, 2002; 2:1585-1597.

Enzmann, V. et al., "Enhanced Induction Of RPE Lineage Markers In Pluripotent Neural Stem Cells Engrafted Into The Adult Rat Subretinal Space," *Investig. Ophthalmol. Visual Sci.*, 2003; 44:5417-5422.

Erices et al., "Mesenchymal Progenitor Cells in Human Umbilical Cord Blood," *Br. J. Haematol.*, 2000; 109:235-242.

Evers, B.M., et al., "Stem Cells in Clinical Practice," *J Am Coll Surg.* 2003; 197(3):458-478.

Fazleabas, A.T. et al., "Endometrial Function: Cell Specific Changes in the Uterine Environment," *Mol. & Cellular. Endo.*, 2002; 186:143-147.

Fernandes, A.M. et al., "Mouse Embryonic Stem Cell Expansion in a Microcarrier-based Stirred Culture System," *Journal of Biotechnology*, 2007; 132:227-236.

Fiegel, H.C. et al., "Liver-Specific Gene Expression In Cultured Human Hematopoietic Stem Cells," *Stem Cells*, 2003; 21:98-104.

Fields, G.B., "Induction of Protein-Like Molecular Architecture by Self-Assembly Processes," *Bioorg. Med. Chem.*, 1999; 7:75-81.

Fischer, D. et al., "Lens-Injury-Stimulated Axonal Regeneration Throughout The Optic Pathway Of Adult Rats," *Exp. Neurol.*, 2001; 172:257-272.

Foley, A. et al., "Heart Induction: Embryology To Cardiomyocyte Regeneration," *Trends Cardiovasc. Med.*, 2004; 14(3):121-125.

Franc, S. et al., "Microfibrillar Composition Of Umbilical Cord Matrix : Characterization Of Fibrillin, Collagen VI And Intact Collagen V," *Placenta*, 1988; 19:95-104.

Freed, C.R. et al., "Transplantation Of Embryonic Dopamine Neurons for Severe Parkinson's Disease," *N. Engl. J. Med.*, 2001; 344(10):710-719.

Frenkel, O. et al., "Activated Macrophages For Treating Skin Ulceration: Gene Expression In Human Monocytes After Hypo-Osmotic Shock," *Clin. Exp. Immunol.*, 2002; 128:59-66.

Friedman, J.A. et al., "Biodegradable Polymer Grafts For Surgical Repair Of The Injured Spinal Cord," *Neurosurgery*, 2002; 51(3):742-751.

Fukuchi, Y. et al., "Human Placenta-Derived Cells Have Mesenchymal Stem/Progenitor Cell Potential," *Stem Cells*, 2004; 22:649-658.

Fukuda, K., "Reprogramming Of Bone Marrow Mesenchymal Stem Cells Into Cardiomyocytes," *C.R. Biol.*, 2002; 325:1027-1038.

Gellersen, B. et al., "Cyclic AMP And Progesterone Receptor Cross-Talk In Human Endometrium: A Decidualizing Affair," *J. Endocrinol.*, 2003; 178(3):357-372.

Gerdes, D. et al., "Cloning And Tissue Expression Of Two Putative Steroid Membrane Receptors," *Biol. Chem.*, 1998; 379:907-911.

Giunta et al., "Inflammaging as a Prodrome to Alzheimer's Disease," Journal of Neuroinflammation, 2008; 5(1):51.

Gong, C., et al., "Intracerebral Hemorrhage-Induced Neuronal Death," *Neurosurgery*, 2001; 48(4):875-883.

Gong, C., et al., "Acute Inflammatory Reaction Following Experimental Intracerebral Hemorrhage in Rat," *Brain Res*, 2000; 871:57-65.

Gökhan, S. et al., "Basic And Clinical Neuroscience Applications Of Embryonic Stem Cells," *Anat. Rec. (New Anat)*, 2001; 265:142-156.

Goodwin, H.S. et al., "Multilineage Differentiation Activity by Cells Isolated from Umbilical Cord Blood: Expression of Bone, Fat, and Neural Markers," *Biology of Blood and Marrow Transplantation*, 2001; 7:581-588.

Gosiewska, A. et al., "Development Of A Three-Dimensional Transmigration Assay for Testing Cell-Polymer Interactions For Tissue Engineering Applications," *Tissue Eng.*, 2001; 7(3):267-277.

Gottleib, D.I. "Large-Scale Sources of Neural Stem Cells," *Annu. Rev. Neurosci.*, 2002; 25:381-407.

Gröhn, P. et al., "Collagen-Coated $BA^{2+}$-Alginate Microcarriers for the Culture of Anchorage-Dependent Mammalian Cells," *BioTechniques*, 1997; 22(5): 970-975.

Gupta, S. et al., "Isolation and Characterization of Kidney-Derived Stem Cells," *J. of Am. Soci. of Nephrol.*, 2006; 17(11):3028-3040.

Halvorsen, Y.C. et al., "Extracellular Matrix Mineralization And Osteoblast Gene Expression By Human Adipose Tissue-Derived Stromal Cells," *Tissue Eng.*, 2001; 7(6):729-741.

Hanahan, D. "Heritable Formation of Pancreatic β-Cell Tumours In Transgenic Mice Expressing Recombinant Insulin/Simian Virus 40 Oncogenes," *Nature*, 1985; 315:115-122.

Hartgerink, J.D. et al., "Peptide-Amphiphile Nanofibers: A Versatile Scaffold for the Preparation of Self-Assembling Materials," *PNAS*, 2002; 99(8):5133-5138.

Haruta, M. et al., "In Vitro And In Vivo Characterization Of Pigment Epithelial Cells Differentiated From Primate Embryonic Stem Cells," *Investig. Ophthalmol. & Visual Sci.*, 2004; 45(3):1020-1025.

Hayflick, L., "The Longevity of Cultured Human Cells," *J. Am. Geriatr. Soc.*, 1974; 22(1):1-12.

Hayflick, L., "The Strategy of Senescence," *Gerontologist*, 1974; 14(1):37-45.

Haynesworth et al., "Cell Surface Antigens on Human Marrow-Derived Mesenchymal Cells are Detected by Monoclonal Antibodies," Bone, 1992; 13:69-80.

Herrera, M.B. et al., "Mesenchymal Stem Cells Contribute to the Renal Repair of Acute Tubular Epithelial Injury," *Int. J. Mol. Med.*, 2004; 14(6):1035-1041.

Hill, D.P. et al., "Screening for Novel Pattern Formation Genes Using Gene Trap Approaches," *Methods in Enzymology*, 1993; 225:664-681.

Hill, M. et al., "Treatment for Swallowing Difficulties (Dysphagia) In Chronic Muscle Disease," *The Cochrane Library Cochrane Database Syst Rev.*, 2004; 2:1-12.

Hishikawa, K. et al., "Musculin/MyoR is Expressed in Kidney Side Population Cells and Can Regulate Their Function," *Journal of Cell Biology*, 2005; 169(6):921-928.

Holz, F.G. et al., "Intraocular Microablation Of Choroidal Tissue By A 308 nm AIDA Excimer Laser For RPE-Transplantation In Patients With Age-Related Macular Degeneration," *Biomed. Technik*, 2003; 48:82-85.

Hongpaisan, J., "Inhibition of Proliferation of Contaminating Fibroblasts By D-Valine in Cultures Of Smooth Muscle Cells From Human Myometrium," *Cell Biol. Int.*, 2000; 24(1):1-7.

Hoynowski, S.M. et al., "Characterization and Differentiation Of Equine Umbilical Cord-Derived Matrix Cells," *Biochemical and Biophysical Research Communications*, 2007; 362:347-353.

Hu, A. et al., "Hepatic Differentiation From Embryonic Stem Cells In Vitro," *Chin. Med. J.*, 2003; 116(12):1893-1897.

Hua, Y., et al., "Plasminogen Activator Inhibitor-1 Induction after Experimental Intracerebral Hemorrhage," *J. Cereb Blood Flow Metab*, 2002; 22:55-61.

Hua, Y., et al., "Behavioral Tests After Intracerebral Hemorrhage in the Rat," *Stroke*, 2002; 33:2478-2484.

Hughes, G.C. et al., "Therapeutic Angiogenesis in Chronically Ischemic Porcine Myocardium: Comparative Effects Of BFGF And VEGF," *Ann. Thorac. Surg.*, 2004; 77:812-818.

Hutmacher, D.W., "Scaffold Design And Fabrication Technologies for Engineering Tissues—State Of The Art And Future Perspectives," *J. Biomater. Sci. Polymer Edn.*, 2001;12(1):107-124.

Igura et al. "Human Placental Derived Stem Cells Differentiate into Neural Cells," Blood , 2002; 100(11): 517A (Abstract 2021).

In't Anker, P., et al., "Isolation of Mesenchymal Stem Cells of Fetal or Maternal Origin from Human Placenta," *Stem Cells*, 2004; 22:1338-1345.

Isacson, O., "The Production And Use Of Cells As Therapeutic Agents in Neurodegenerative Diseases," *The Lancet (Neurology)*, 2003; 2:417-424.

Isacson, O., et al., "Specific Axon Guidance Factors Persist In The Adult Brain As Demonstrated by Pig Neuroblasts Transplanted To The Rat," *Neurosci.*, 1996; 75(3):827-837.

Ishii, M. et al., "Molecular Markers Distinguish Bone Marrow Mesenchymal Stem Cells From Fibroblasts," *Biochemical and Biophysical Research Communications*, 2005; 332:297-303.

Ito, Y. et al., "A Quantitative Assay Using Basement Membrane Extracts To Study Tumor Angiogenesis In Vivo," *Int. J. Cancer*, 1996; 67:148-152.

Jackson, K.A. et al., "Regeneration Of Ischemic Cardiac Muscle and Vascular Endothelium By Adult Stem Cells," *J. Clin. Invest.*, 2001; 107:1395-1402.

Jaffe, E.A. et al., "Culture Of Human Endothelial Cells Derived From Umbilical Veins; Identification by Morphologic and Immunologic Criteria" *J Clin Invest*, 1973; 52:2745-2756.

Janderová, L. et al., "Human Mesenchymal Stem Cells As an In Vitro Model For Human Adipogenesis," *Obes. Res.*, 2003; 11(1):65-74.

Jang, Y.K. et al., "Retinoic Acid-Mediated Induction Of Neurons And Glial Cells From Human Umbilical Cord-Derived Hematopoietic Stem Cells," *J. Neurosci. Res.*, 2004; 75:573-584.

Jikuhara, T. et al., "Left Atrial Function As A Reliable Predictor Of Exercise Capacity in Patients With Recent Myocardial Infarction," *Chest*, 1997; 111(4):922-928.

Jin et al., "Neurogenesis in Dentate Subgranular Zone and Rostral Subventricular Zone After Focal Cerebral Ischemia in the Rat," *PNAS*, 2001; 98(8):4710-4715.

Johe, K.K. et al., "Single Factors Direct the Differentiation Of Stem Cells From The Fetal And Adult Central Nervous System," *Genes & Devel.*, 1996; 10:3129-3140.

Johnstone, B. et al., "In Vitro Chondrogenesis Of Bone-Marrow-Derived Mesenchymal Progenitor Cells," *Exp. Cell Res.*, 1998; 238:265-272.

Jomura, S. et al., "Potential Treatment of Cerebral Global Ischemia with Oct-4+ Umbilical Cord Matrix Cells," *Stem Cells*, 2006, AlphaMed Press, Downloaded from www.StemCells.com at Ethicon, Inc. on Sep. 11, 2006 and Supplemental Data: 2.

Jones, J. et al., "Insulin-Like Growth Factors and their Binding Proteins: Biological Actions," Endocrine Review, 1995; 16(1):3-34.

Jones-Villeneuve, E.M. et al., "Retinoic Acid-Induced Neural Differentiation Of Embryonal Carcinoma Cells," *Mol. & Cellu. Biol.*, 1983; 3(12):2271-2279.

Jørgensen, N.R. et al., "Intercellular Calcium Signaling Occurs Between Human Osteoblasts and Osteoclasts and Requires Activation of Osteoclast P2X7 Receptors," *The Journal of Biological Chemistry*, 2002; 277(9):7574-7580.

Joussen, A.M. "Cell Transplantation in Age Related Macular Degeneration: Current Concepts and Future Hopes," *Graefe's Arch. Clin. Exp. Ophthalmol.*, 2004; 242:1-2.

Kadiyala, S. et al., "Culture Expanded Canine Mesenchymal Stem Cells Possess Osteochondrogenic Potential In Vivo and In Vitro," *Cell Transplant.*, 1997; 6(2):125-134.

Kawata, M. et al., "Transcriptional Control Of HLA-A,B,C Antigen In Human Placental Cytotrophoblast Isolated Using Trophoblast- and HLA-Specific Monoclonal Antibodies and the Fluorescence-Activated Cell Sorter," *J. Exp. Med.*, 1984; 160:633-651.

Keyvani et al., "Plasticity-Associated Molecular and Structural Events in the Injured Brain," *Journal of Neuropathology Experimental Neurology*, 2002; 61(10):831-840.

Kicic, A. et al., "Differentiation Of Marrow Stromal Cells Into Photoreceptors In The Rat Eye," *J. of Neurosci.*, 2003; 23(21):7742-7749.

Kim, J. et al., "Dopamine Neurons Derived From Embryonic Stem Cells Function In An Animal Model Of Parkinson's Disease," *Nature*, 2002; 418:50-56.

Kim, J.Y. et al., "Ocular Surface Reconstruction: Limbal Stem Cell Transplantation," *Ophthal. Clin. N. Am.*, 2003; 16:67-77.

Kim, S.K. et al., "Intercellular Signals Regulating Pancreas Development And Function," *Genes Dev.*, 2001; 15:111-127.

Kirschstein, R. et al., "Can Stem Cells Repair a Damaged Heart?" *Stem Cells: Scientific Progress and Future Research Directions*, 2001; 87-92.

Kitamura, S. et al., "Establishment and Characterization of Renal Progenitor Like Cells from S3 Segment of Nephron in Rat Adult Kidney," *The FASEB Journal*, 2005; 19:1789-1797.

Klass et al., "Intravenous Mononuclear Marrow Cells Reverse Neuropathic Pain from Experimental Mononeuropathy," International Anesthesia Research Society, 2007; 104:944-949.

Klassen, H. et al., "Stem Cells And Retinal Repair," *Prog. Retin. Eye Res.*, 2004; 23:149-181.

Kolb, B, "Synaptic Plasticity and the Organization of Behaviour after Early and Late Brain Injury," *Canadian Journal of Experimental Psychology*, 1999; 53(1):62-76.

Kurtz, A. et al., "Activity in Fetal Bovine Serum that Stimulates Erythroid Colony Formation in Fetal Mouse Livers is Insulinlike Growth Factor I," *J. Clin. Invest.*, 1985; 76:1643-1648.

Kusama, V. et al., "Growth and morphogenesis of mouse prostate epithelial cells in collagen gel matrix culture" *Cell Biol Int Rep*, 1989; 13:569-575.

Laface, D. et al., "Gene Transfer Into Hematopoietic Progenitor Cells Mediated By An Adeno-Associated Virus Vector," *Virology*, 1988; 162:483-486.

Lang, K.J.D. et al., "Differentiation Of Embryonic Stem Cells To A Neural Fate: A Route To Re-Building The Nervous System?" *J. of Neurosci. Res.*, 2004; 76:184-192.

Langeggen, H. et al., "HUVEC Take Up Opsonized Zymosan Particles And Secrete Cytokines IL-6 and IL-8 In Vitro," *FEMS Immunol. Med. Microbiol.*, 2003; 36:55-61.

Le Belle, J.E. et al., "Stem Cells for Neurodegenerative Disorders: Where Can We Go From Here?," *Biodrugs*, 2002; 16(6):389-401.

Le Bouteiller, P. et al., "Soluble HLA-G1 At The Materno-Foetal Interface—A Review," *Placenta*, 2003; 24(Suppl. A):S10-S15.

Li, C.D. et al, "Mesenchymal Stem Cells Derived From Human Placenta Suppress Allogeneic Umbilical Cord Blood Lymphocyte Proliferation," *Cell Research*, 2005; 15(7):539-547.

Li, L.X. et al., "Inherited Retinal Dystrophy In The RCS Rat: Prevention Of Photoreceptor Degeneration By Pigment Epithelial Cell Transplantation," *Exp. Eye Res.*, 1988; 47:911-917.

Li, Y. et al., "Transplanted Olfactory Ensheathing Cells Promote Regeneration Of Cut Adult at Optic Nerve Axons," *J. of Neuro.*, 2003; 23(21):7783-7788.

Li, Y. et al., "Intracerebral Transplantation Of Bone Marrow Stromal Cells In A 1-Methyl-4-Phenyl-1,2,3,6-Tetrahydropyridine Mouse Model Of Parkinson's Disease," *Neuroscience Letts.*, 2001; 315:67-70.

Li, Y. et al., "Intact, Injured, Necrotic and Apoptotic Cells after Focal Cerebral Ischemia in the Rat," *J. Neurol. Sci.*, 1998; 156:119-132.

Li, Y. et al., "Ultrastructural and Light Microscopic Evidence of Apoptosis after Middle Cerebral Artery Occlusion in the Rat," *Am. J. Pathol.*, 1995; 146(5):1045-1051.

Li, Y. et al., "Human Marrow Stromal Cell Therapy for Stroke in Rat Neurotrophins and Functional Recovery," *Neurology*, 2002; 59:514-523.

Liddiard, et al., "An Improved Method for the Preparation of Human Fetal and Adult Hepatocytes," *Arch. Toxicol.*, 1980; 44:107-112.

Lindenlaub, T. et al., "Partial Sciatic Nerve Transection as a Model of Neuropathic Pain: A Qualitative and Quantitative Study," *PAIN*, 2000; 89: 97-106.

Lindvall, O. et al., "Stem Cell Therapy For Human Neurodegenerative Disorders—How To Make It Work," *Nature Medicine*, 2004;10(Suppl.):S42-S50.

Liu, Y. et al., "Molecular And Genetic Mechanisms Of Obesity: Implications For Future Management," *Curr. Mol. Med.*, 2003; 3(4):325-340.

Liu et al, "Constitutive and Regulated Expression of Telomerase Reverse Transcriptase (hTERT) in Human Lymphocytes," Proc. Natl. Acad. Sci., 1999; 96:5147-5152.

Lockhart, D.J. et al., "Expression Monitoring by Hybridization to High-Density Oligonucleotide Arrays," *Nat. Biotechnol.*, 1996; 14:1675-1680.

Lodie, T.A. et al., "Systematic Analysis of Reportedly Distinct Populations of Mulitpotent Bone Marrow-Derived Stem Cells Reveals a Lack of Distinction," *Tissue Engineering*, 2002; 8(5):739-751.

Lois, C. et al., "Chain Migration of Neuronal Precursors," *Science*, 1996; 271:978-981.

Lund, R.D. et al., "Cell Transplantation As A Treatment For Retinal Disease," *Progress in Retinal and Eye Research*, 2001; 20(4):415-449.

Lund, R.D. et al., "Subretinal Transplantation Of Genetically Modified Human Cell Lines Attenuates Loss Of Visual Function In Dystrophic Rats," *PNAS*, 2001; 98(17):9942-9997.

Lund, R.L. et al., "Retinal Transplantation: Progress And Problems in Clinical Application," *J. Leukocyte Biol.*, 2003; 74:151-160.

Luo, D. et al., "Synthetic DNA Delivery Systems," *Nat. Biotechnol.*, 2000; 18(1):33-36.

Luyten, F.P. et al., "Skeletal Tissue Engineering: Opportunities and Challenges," *Best Pract. Res. Clin. Rheumatol.*, 2001; 15(5):759-769.

Ma, L. et al., "Human Umbilical Cord Wharton's Jelly-Derived Mesenchymal Stem Cells Differentiation into Nerve-Like Cells," *Chinese Med. Jour.*, 2005; 118(23):1987-1993.

MacDONALD, R.J. "Expression Of The Pancreatic Elastase I Gene In Transgenic Mice," *Hepatology*, 1987; 7(1):42S-51S.

Mackay, A.M. et al., "Chondrogenic Differentiation Of Cultured Human Mesenchymal Stem Cells From Marrow," *Tissue Engineering*, 1998; 4(4):415-428.

Makino, S. et al., "Cardiomyocytes can be generated from marrow stromal cells in vitro," J. Clin. Invest., 1999; 103:697-705.

Marx, W.F. et al., "Endovascular Treatment Of Experimental Aneurysms by Use Of Biologically Modified Embolic Devices: Coil-Mediated Intraaneurysamal Delivery Of Fibroblast Tissue Allografts," *Am. J. Neuroradiol.*, 2001; 22:323-333.

Mason, A.J. et al., "The Hypogonadal Mouse: Reproductive Functions Restored by Gene Therapy," *Science*, 1986; 234:1372-1378.

Matsushita et al., "Evidence for Apoptosis After Intracerebral Hemorrhage in Rat Striatum," *Journal of Cerebral Blood Flow & Metabolism*, 2000; 20:396-404.

Mayer-Proschel, M. et al., "Isolation Of Lineage-Restricted Neuronal Precursors From Multipotent Neuroepithelial Stem Cells," *Neuron.*, 1997; 19:773-785.

Medicetty, S. et al., "Transplantation of Human Umbilical Cord Matrix Stem Cells Alleviates Apomorphine-Induced Rotations in Parkinsonian Rats", 2003, XP-002383776, 1 page.

Meier et al., "Spastic Paresis After Perinatal Brain Damage in Rats is Reduced by Human Cord Blood Monomuclear Cells," Pediatric Research, 2006; 59(2):244-249.

Melero-Martin, J. et al., "Optimal In-Vitro Expansion of Chondroprogenitor Cells in Monolayer Culture," *Biotechnology and Bioengineering*, 2006; 93(3):519-533.

Merx, M.W. et al., "Transplantation Of Human Umbilical Vein Endothelial Cells Improves Left Ventricular Function In A Rat Model Of Myocardial Infarction," *Basic Res. Cardiol.*, 2005; 100:208-216.

Miñambres et al., "Cerebral Apoptosis in Severe Traumatic Brain Injury Patients: An In Vitro, In Vivo, and Postmortem Study," *Journal of Neurotrauma*, 2008; 25:581-591.

Mitchell, K.E. et al., "Matrix Cells From Wharton's Jelly Form Neurons And Glia," *Stem Cells*, 2003; 21:50-60.

Moll, S. et al., "Monitoring Warfarin Therapy In Patients With Lupus Anticoagulants," *Ann. Intern. Med.*, 1997; 127(3):177-185.

Mombaerts, P. et al., "Creation Of A Large Genomic Deletion At The T-Cell Antigen Receptor β-Subunit Locus In Mouse Embryonic Stem Cells By Gene Targeting," *Proc. Nat. Acad. Sci. USA*, 1991; 88:3084-3087.

Morgenstern, J.P. et al., "Advanced Mammalian Gene Transfer: High Titre Retroviral Vectors With Multiple Drug Selection Markers And A Complementary Helper-Free Packaging Cell Line," *Nucleic Acids Res.*, 1990; 18(12):3587-3596.

Moore, A.E. et al., "Parkinsonian Motor Deficits are Reflected by Proportional A9/A10 Dopamine Neuron Degeneration in the Rat," *Exp. Neurol.*, 2001; 172(2):363-376.

Morishima, Y. et al., "The Clinical Significance of Human Leukocyte Antigen (HLA) Allele Compatibility in Patients Receiving a Marrow Transplant from Serologically HLA-A, HLA-B, and HLA-DR Matched Unrelated Donors," *Blood*, 2002; 99(11):4200-4206.

Moulder, J.E., "Pharmacological Intervention To Prevent Or Ameliorate Chronic Radiation Injuries," *Semin. Radiat. Oncol.*, 2003; 13(1):73-84.

Nakamura, T. et al., "Ocular Surface Reconstruction Using Cultivated Mucosal Epithelial Stem Cells," *Cornea*, 2003; 22(Supp. 1):S75-S80.

Naughton, B.A. et al., "Cells isolated from Wharton's jelly of the human umbilical cord develop a cartilage phenotype when treated with TGF-b in vitro," 1997; *FASEB J* 11:A19 (Abstract 108).

Nicosia, R.F. et al., "Modulation Of Microvascular Growth And Morphogenesis By Reconstituted Basement Membrane Gel In Three-Dimensional Cultures Of Rat Aorta: A Comparative Study Of Angiogenesis In Matrigal, Collagen, Fibrin, And Plasma Clot," In Vitro *Cell Dev. Biol.*, 1990; 26:119-128.

Ninichuk, V. et al., "Multipotent Mesenchymal Stem Cells Reduce Interstitial Fibrosis But Do Not Delay Progression of Chronic Kidney Disease in Collagen4A3-Deficient Mice," *Kidney Int.*, 2006; 70(1):121-129.

Nishishita, T. et al., "A Potential Pro-Angiogenic Cell Therapy With Human Placenta-Derived Mesenchymal Cells," *Biochemical and Biophysical Research Communications*, 2004; 325:24-31.

Nixon, P.J. et al., "The Contribution Of Cone Responses To Rat Electroretinograms," *Clin. Experiment Ophthalmol.*, 2001; 29(3):193-196.

Nork, T.M. et al., "Swelling and Loss of Photoreceptors in Chronic Human and Experimental Glaucomas," *Arch. Ophthalmol.*, 2000; 118:235-245.

Nusinowitz, S. et al., "Rod Multifocal Electroretinograms In Mice," *Invest Ophthalmol Vis. Sci.*, 1999; 40(12): 2848-2858.

Oh, S.H. et al., "Hepatocyte Growth Factor Induces Differentiation Of Adult Rat Bone Marrow Cells Into A Hepatocyte Lineage In Vitro," *Biochem. & Biophys. Res. Comm.*, 2000; 279(2):500-504.

Okumoto, K. et al., "Differentiation Of Bone Marrow Cells Into Cells That Express Liver-Specific Genes In Vitro: Implication Of The Notch Signals In Differentiation," *Biochem. & Biophys. Res. Commun.*, 2003; 304:691-695.

Oliver, J.A. et al., "The Renal Papilla is a Niche for Adult Kidney Stem Cells," *J. Clin Invest.*, 2004, 114(6):795-804.

Orlic, D. et al., "Stem Cells for Myocardial Regeneration," *Circ. Res.*, 2002; 91:1092-1102.

Ornitz, D.M. et al., "Elastase I Promoter Directs Expression Of Human Growth Hormone and SV40 T Antigen Genes To Pancreatic Acinar Cells in Transgenic Mice," *Cold Spring Harbor Symp. Quant. Biol.*, 1985; 50:399-409.

Osborne, N.N. et al., "Some Current Ideas On The Pathogenesis And The Role Of Neuroprotection In Glaucomatous Optic Neuropathy," *Eur. J. Ophthalmol.*, 2003; 13(Supp. 3):S19-S26.

Palù, G. et al., "In Pursuit Of New Developments For Gene Therapy Of Human Diseases," *J. Biotechnol.*, 1999; 68:1-13.

Panepucci, R.A. et al., "Comparison of Gene Expression of Umbilical Cord Vein and Bone Marrow-Derived Mesenchymal Stem Cells," *Stem Cells*, 2004; 22:1263-1278.

Parent et al., "Rat Forebrain Neurogenesis and Striatal Neuron Replacement After Focal Stroke," *Ann. Neurol.*, 2002; 52:802-813.

Pera, M.F. et al., "Human Embryonic Stem Cells", *J. Cell Science*, 2000; 113:5-10.

Pesce et al., "Myoendothelial Differentiation of Human Umbilical Cord Blood-Derived Stem Cells in Ischemic Limb Tissues," *Circulation Research*, 2003; 93:e51-e62.

Petersdorf, E.W., "HLA Matching in Allogeneic Stem Cell Transplantation," *Curr. Op. Hematol*, 2004; 11:386-391.

Phipps, J.A. et al., "Paired-Flash Identification Of Rod And Cone Dysfunction In The Diabetic Rat," *Investigative Ophthalmology & Visual Science*, 2004; 45:4592-4600.

Pisharodi, M. et al., "An Animal Model for Neuron-Specific Spinal Cord Lesions by the Microinjection of N-Methylaspartate, Kainic Acid, and Quisqualic Acid," 1985; *Appl. Neurophysiology* 48:226-233.

Pittenger, M.F. et al., "Multilineage Potential Of Adult Human Mesenchymal Stem Cells," *Science*, 1999; 284:143-47 and seven pages of online supplementary material.

Pittenger, M.F. et al., "Mesenchymal Stem Cells and Their Potential as Cardiac Therapeutics," *Circ. Res.*, 2004; 95:9-20.

Plaia, T., et al., "Characterization Of A New NIH-Registered Variant Human Embryonic Stem Cell Line, BG01V: A Tool for Human Embryonic Stem Cell Research," *Stem Cells*, 2006: 24: 531-546.

Plate, KH, "Mechanisms of Angiogenesis in the Brain," *Journal of Neuropathology Experimental Neurology*, 1999; 58(4):313-320.

Pountos, I. et al., "Mesenchymal Stem Cell Tissue Engineering: Techniques for Isolation, Expansion and Application," *Injury, Int. J. Care Injured*, 2007; 38:S23-S33.

Rabbany, S.Y. et al., "Molecular Pathways Regulating Mobilization Of Marrow-Derived Stem Cells For Tissue Revascularization," *TRENDS in Molecular Med.*, 2003; 9(3):109-117.

Rafii, S. et al., "Therapeutic Stem And Progenitor Cell Transplantation For Organ Vascularization and Regeneration," *Nature Med.*, 2003; 9(6):702-712.

Rahman, Z. et al., "Isolation and Primary Culture Urothelial Cells from Normal Human Bladder," *Urol. Research*, 1987; 15:315-320.

Ramon-Cueto, A. et al., "Functional Recovery Of Paraplegic Rats And Motor Axon Regeneration In Their Spinal Cords By Olfactory Ensheathing Glia," *Neuron*, 2000; 25:425-435.

Readhead, C. et al., "Expression Of A Myelin Basic Protein Gene In Transgenic Shiverer Mice: Correction Of The Dysmyelinating Phenotype," *Cell*, 1987; 48:703-712.

Refaie, A. et al., "Experimental Islet Cell Transplantation In Rats: Optimization Of The Transplantation Site," *Trans. Proc.*, 1998; 30:400-403.

Rehman, J. et al., "Secretion of Angiogenic and Antiapoptotic Factors by Human Adipose Stromal Cells," *Circulation*, 2004; 109:1292-1298.

Reubinoff, B.E. et al., "Neural Progenitors From Human Embryonic Stem Cells," *Nature Biotechnology*, 2001; 19:1134-1140.

Reyes, M. et al., "Purification And Ex Vivo Expansion Of Postnatal Human Marrow Mesodermal Progenitor Cells," *Blood*, 2001; 98(9):2615-2625.

Rezai, K.A. et al., "Iris Pigment Epithelium Transplantation," *Graefe's Arch. Clin. Ophthalmol.*, 1997; 235:558-562.

Rickard, D.J. et al., "Induction Of Rapid Osteoblast Differentiation In Rat Bone Marrow Stromal Cell Cultures By Dexamethasone And BMP-2," *Dev. Biol.*, 1994; 161:218-228.

Rios, M. et al., "Catecholamine Synthesis is Mediated by Tyrosinase in the Absence of Tyrosine Hydroxylase," *J. Neurosci.*, 1999, 19(9):3519-3526.

Romanov, Y.A. et al., "Searching For Alternative Sources Of Postnatal Human Mesenchymal Stem Cells: Candidate MSC-Like Cells from Umbilical Cord," *Stem Cells*, 2003; 21:105-110.

Roskams, A.J. et al., "Directing Stem Cells And Progenitor Cells On The Stage Of Spinal Cord Injury," *Exp. Neurol.*, 2005; 193:267-272.

Russo, E., Cultivating Policy from Cell Types, *The Scientist*, 2001; 15(11):6 (printout is numbered 1-6).

Rutherford, A. et al., "Eyeing-Up Stem Cell Transplantation," *Trends in Molecular Medicine*, 2001; 7(1):11.

Sagrinati, C. et al., "Isolation and Characterization of Multipotent Progenitor Cells from the Bowman's Capsule of Adult Human Kidney," *Journal of American Society of Nephrology*, 2006; 17:2443-2456.

Sahn, D.J. et al., "Recommendations Regarding Quantitation In M-Mode Echocardiography: Results Of A Survey Of Echocardiographic Measurements," *Circulation*, 1978; 58(6):1072-1083.

Sakariassen, K.S. et al., "Methods And Models To Evaluate Shear-Dependent And Surface Reactivity-Dependent Antithrombotic Efficacy," *Thromb. Res.*, 2001; 104:149-174.

Salgado, A.J. et al., "Bone Tissue Engineering: State of the Art and Future Trends," *Macromol. Biosci.*, 2004; 4:743-765.

Schallert, T. et al., "Use-Dependent Structural Events in Recovery of Function," *Brain Plasticity, Adv. Neurol.*, 1997; 73:229-238.

Schouten, J.W. et al., "A Review and Rationale for the Use of Cellular Transplantation as a Therapeutic Strategy for Traumatic Brain Injury," *Journal of Neurotrauma*, 2004; 21(11):1501-1538.

Schraermeyer, U. et al., "Subretinally Transplanted Embryonic Stem Cells Rescue Photoreceptor Cells From Degeneration in the RCS Rats," *Cell Transplantation*, 2001; 10:673-680.

Schreuder, G.M. et al., "The HLA Dictionary 1999: A Summary of HLA-A, -B, -C, -DRB1/3/4/5, -DQB1 Alleles and Their Association with Serologically Defined HLA-A, -B, -C, -DR and -DQ Antigens," *Tissue Antigens*, 1999; 54:409-437.

Schwartz, R.E. et al., "Multipotent Adult Progenitor Cells From Bone Marrow Differentiate Into Functional Hepatocyte-Like Cells," *J. of Clin. Invest.*, 2002; 109:1291-1302.

Seaver, S.S. et al. "The chick oviduct in tissue culture. I. Initial characterization of growing primary oviduct tissue cultures," *Exp. Cell Res.*, 1984; 155: 241-251.

Sébire, G. et al., "In Vitro Production Of IL-6, IL-1β, And Tumor Necrosis Factor-αby Human Embryonic Microglial And Neural Cells," *J. Immunol.*, 1993; 150(4):1517-1523.

Seiji, T. et al., Possibility of Regenerative Medicine Using Human Amniotic Cells, *Regenerative Medicine*, 2002; 1(2):79-85—with English language abstract.

Sethe, S. et al., "Aging Of Mesenchymal Stem Cells," *Ageing Research Reviews*, 2006; 5:91-116.

Seyfried, D. et al., "Effects of Intravenous Administration of Human Bone Marrow Stromal Cells After Intracerebral Hemorrhage in Rats," *J Neurosurg*, 2006; 104:313-318.

Seyfried, D. et al., "Improvement in Neurological Outcome after Administration of Atorvastatin Following Experimental Intracerebral Hemorrhage in Rats," *J Neurosurg*, 2004; 101:104-107.

Shake et al., "Mesenchymal stem cell implantation in a swine myocardial infarct model: engraftment and functional effects," Ann Thorac Surg, 2002; 73:1919-1926.

Shani, M., "Tissue-Specific Expression Of Rat Myosin Light-Chain 2 Gene in Transgenic Mice," *Nature*, 1985; 314:283-286.

Shimizu, T. et al., "Cell Sheet Engineering For Myocardial Tissue Reconstruction," *Biomaterials*, 2003; 24:2309-2316.

Shimizu, T. et al., "Fabrication of Pulsatile Cardiac Tissue Grafts Using a Novel 3-Dimensional Cell Sheet Manipulation Technique and Temperature-Responsive Cell Culture Surfaces," *Circulation Research*, 2002; 90:e40-e48.

Shuto, T. et al., "Dexamethasone Stimulates Osteoclast-Like Cell Formation By Inhibiting Granulocyte-Macrophage Colony-Stimulating Factor Production In Mouse Bone Marrow Cultures," *Endocrinology*, 1994; 134(3):1121-1126.

Siminoff, R. et al., "Properties Of Reptilian Cutaneous Mechanoreceptors," *Exp. Neurol.*, 1968; 20:403-414.

Song, H. et al., "Astroglia Induce Neurogenesis From Adult Neural Stem Cells," *Nature*, 2002; 417:39-44.

Sordillo, L.M. et al., "Culture Of Bovine Mammary Epithelial Cells In D-Valine Modified Medium: Selective Removal Of Contaminating Fibroblasts," *Cell Biol. Int. Rep.*, 1988; 12(5):354-365.

Street, C.N. et al., "Stem Cells: A Promising Source Of Pancreatic Islets For Transplantation In Type 1 Diabetes," *Curr. Top Dev. Biol.*, 2003; 58:111-136.

Stroemer et al., "Enhanced Neocortical Neural Sprouting, Synaptogenesis, and Behavioral Recovery with D-Amphetamine Therapy after Neocortical Infarction in Rats," *Stroke*, 1998; 29:2381-2395.

Stroemer et al., "Neocortical Neural Sprouting, Synaptogenesis, and Behavioral Recovery After Neocortical Infarction in Rats," *Stroke*, 1995; 26:2135-2144.

Svendsen, C.N. "The Amazing Astrocyte," *Nature*, 2002; 417:29-32.

Svendsen, C.N. et al., "Long-Term Survival of Human Central Nervous System Progenitor Cells Transplanted Into A Rat Model Of Parkinson's Disease," *Experim. Neurol.*, 1997; 148:135-146.

Swanson, R.A. et al., "A Semiautomated Method for Measuring Brain Infarct Volume," *J. Cereb. Blood Flow Metab.*, 1990; 10:290-293.

Swift, G.H. et al., "Tissue-Specific Expression Of The Rat Pancreatic Elastase I Gene In Transgenic Mice," *Cell*, 1984; 38:639-646.

Taylor, D.A. et al., "Regenerating Functional Myocardium: Improved Performance After Skeletal Myoblast Tranplantation," *Nature Medicine*, 1998; 4(8):929-1200.

Taylor, D.A. et al., "Cardiac Chimerism As A Mechanism For Self-Repair: Does It Happen And If So To What Degree?" *Circulation*, 2002; 106:2-4.

Thorsby, E. et al., "Role of HLA Molecules in the Induction of Alloimmune Responses: Clinical Significance in the Cyclosporine Era," *Transplant Proc.*, 2004; 36(Suppl 2S):16S-21S.

Timmermans, F. et al., "Stem Cells For The Heart, Are We There Yet?" *Cardiology*, 2003; 100(4):176-185.

Toma, C. et al., "Human Mesenchymal Stem Cells Differentiate To A Cardiomyocyte Phenotype In The Adult Murine Heart," *Circulation*, 2002; 105:93-98.

Tomita, M. et al., "Bone Marrow-Derived Stem Cells Can Differentiate Into Retinal Cells In Injured Rat Retina," *Stem Cells*, 2002; 20:279-283.

Tremain, N. et al., "MicroSAGE Analysis of 2,353 Expressed Genes in a Single Cell-Derived Colony of Undifferentiated Human Mesenchymal Stem Cells Reveals mRNAs of Multiple Cell Lineages," Stem Cells, 2001; 19:408-418.

Tresco, P.A. et al., "Cellular Transplants As Sources for Therapeutic Agents," *Advanced Drug Delivery Reviews*, 2000; 42:3-27.

Turner, D., "The Human Leucocyte Antigen (HLA) System," *Vox Sang.*, 2004; 87(Suppl 1):S87-S90.

Turner, J.F., "Inherited Retinal Dystrophy In The RCS Rat: Prevention Of Photoreceptor Degeneration By Pigment Epithelial Cell Transplantation," *Exp. Eye Res.*, 1988; 47:911-917.

Ujike, H. et al., "Gene Expression Related to Synaptogenesis, Neuritogenesis, and MAP Kinase in Behavioral Sensitization to Psychostimulants," *Ann. N.Y. Acad. Sci.*, 2002; 965:55-67.

Ulloa-Montoya, F. et al., "Culture Systems for Pluripotent Stem Cells," *Journal of Bioscience and Bioengineering*, 2005; 100(1):12-27.

"Unigene Entry for Hs.522632, Homo Sapiens TMP Metallopeptidase Inhibitor 1 (TIMP1)," printed from http://www.ncbi.nlm.nih.gov/UniGene on Oct. 12, 2006.

Urbich, C. et al., "Endothelial Progenitor Cells Characterization and Role in Vascular Biology," *Circ. Res.*, 2004; 95:343-353.

Vajsar, J. et al., "Walker-Warburg Syndrome," *Orphanet Journal of Rare Diseases*, 2006; 1:29.

Van Hoffelen, S.J. et al., "Incorporation of Murine Brain Progenitor Cells Into the Developing Mammalian Retina," *Invest. Ophthalmol. Vis. Sci.*, 2003; 44(1):426-434.

Vassliopoulos, G. et al., "Transplanted Bone Marrow Regenerates Liver By Cell Fusion," *Nature*, 2003; 422:901-904.

Verma, I. M. et al., "Gene Therapy—Promises, Problems and Prospects," *Nature*, 1997; 389:239-242.

Vermot-Desroches, C. et al., "Heterogeneity Of Antigen Expression Among Human Umbilical Cord Vascular Endothelial Cells: Identification Of Cell Subsets By Co-Expression Of Haemopoietic Antigens," *Immunol. Lett.*, 1995; 48:1-9.

Villegas-Perez, M.P. et al., "Influences Of Peripheral Nerve Grafts On The Survival And Regrowth Of Axotomized Retinal Ganglion Cells in Adult Rats," *J. Neurosci.*, 1988; 8(1):265-280.

Villegas-Perez, M.P. et al., "Rapid and Protracted Phases Of Retinal Ganglion Cell Loss Follow Axotomy In The Optic Nerve Of Adult Rats," *J. Neurobiology*, 1993; 24(1):23-36.

Von Koskull, H. et al., "Induction Of Cytokeratin Expression In Human Mesenchymal Cells," *J. Cell Physiol.*, 1987; 133:321-329.

Walboomers, X .F. et al., "Cell And Tissue Behavior On Micro-Grooved Surfaces," *Odontology*, 2001; 89:2-11.

Walter et al., "Statin Therapy Accelerates Reendothelialization A Novel Effect Involving Mobilization and Incorporation of Bone Marrow-Derived Endothelial Progenitor Cells," *Circulation*, 2002; 105:3017-3024.

Wang, X . et al., "Cell Fusion Is The Principal Source Of Bone-Marrow-Derived Hepatocytes," *Nature*, 2003; 422:897-900.

Wegman, A. et al., "Nonsteroidal Anti-Inflammatory Drugs Or Acetaminophen For Osteoarthritis Of The Hip Or Knee? A Synstematic Review Of Evidence And Guidelines," *J. Rheumatol.*, 2004; 31(2):344-354.

Weiss, M.L. et al., "Transplantation Of Porcine Umbilical Cord Matrix Cells Into The Rat Brain," *Exp. Neur.*, 2003; 182:288-299.

Weiss, M.L. et al., "Human Umbilical Cord Matrix Stem Cells: Preliminary Characterization And Effect Of Transplantation In A Rodent Model Of Parkinson's Disease," *Stem Cells*, 2006; 24:781-792.

Wenning, G.K. et al., "Neural Transplantation in Animal Models of Multiple System Atrophy: A Review," *J. Nueral Transm.*, 1999; Suppl.(55):103-113.

Williams, J.T. et al., "Cells Isolated From Adult Human Skeletal Muscle Capable Of Differentiating Into Multiple Mesodermal Phenotypes," *Am. Surg.* 1999; 65(I):22-6.

Wobus, A.M. et al., "Retinoic Acid Accelerates Embryonic Stem Cell-Derived Cardiac Differentiation and Enhances Development Of Ventricular Cardiomyocytes," *J. Mol. Cell Cardiol.*, 1997; 29:1525-1539.

Wolford, L.M. et al., "Considerations in Nerve Repair," *BUMC Proceedings*, 2003; 16(2):152-156.

Woodbury, D., et al., "Adult Rat And Human Bone Marrow Stromal Cells Differentiate Into Neurons," *J. Neurosci. Res.*, 2000; 61:364-370.

Wulf, G.G. et al., "Mesengenic Progenitor Cells Derived From Human Placenta," *Tissue Engineering*, 2004; 10(7/8):1136-1147.

Xi, G, et al., "Mechanisms of Edema Formation After Intracerebral Hemorrhage Effects of Extravasated Red Blood Cells on Blood Flow and Blood-Brain Barrier Integrity," *Stroke*, 2001; 32:2932-2938.

Xu, C. et al., "Characterization And Enrichment Of Cardiomyocytes Derived From Human Embryonic Stem Cells," *Circ. Res.*, 2002; 91:501-508.

Xu, Y. et al., "Dopamine, In The Presence Of Tyrosinase, Covalently Modifies And Inactivates Tyrosine Hydroxylase," *J. Neurosci. Res.*, 1998; 54:691-697.

Yamashima, T., "Implication of Cysteine Proteases Calpain, Cathepsin and Caspase in Ischemic Neuronal Death of Primates," *Progress in Neurobiology*, 2000; 62:273-295.

Yang, C. et al., "Enhancement Of Neovascularization With Cord Blood CD133+ Cell-Derived Endothelial Progenitor Cell Transplantation," *Thrombosis and Haemostasis*, 2004; 91:1202-1212.

Yang, H. et al., "Region-Specific Differentiation Of Neural Tube-Derived Neuronal Restricted Progenitor Cells After Heterotopic Transplantation," *PNAS*, 2000; 97(24):13366-13371.

Ye Q. et al., "Recovery Of Placental-Derived Adherent Cells With Mesenchymal Stem Cell Characteristics", *Blood*, 2001; 98(11 Part 2):147B (Abstract No. 4260).

Yip, H.K., et al., "Axonal Regeneration Of Retinal Ganglion Cells: Effect Of Trophic Factors," *Prog. Retin Eye Res.*, 2000; 19(5):559-575.

Yokoo, T. et al., "Stem Cell Gene Therapy For Chronic Renal Failure," *Curr Gene Ther.*, 2003; 3:387-394.

Yu, M. et al., "Mid-Trimester Fetal Blood-Derived Adherent Cells Share Characteristics Similar To Mesenchymal Stem Cells But Full-Term Umbilical Cord Blood Does Not," *British J. of Haematology*, 2004; 124:666-675.

Zangani, D. et al., "Multiple Differentiation Pathways Of Rat Mammary Stromal Cells In Vitro: Acquisition Of A Fibroblast, Adipocyte Or Endothelial Phenotype Is Dependent On Hormonal and Extracellular Matrix Stimulation," *Differentiation*, 1999; 64:91-101.

Zhang, L. et al., "A Test for Detecting Long-Term Sensorimotor Dysfunction in the Mouse after Focal Cerebral Ischemia," *J. Neurosci. Methods*, 2002; 117:207-214.

Zhang, S. et al., "In Vitro Differentiation Of Transplantable Neural Precursors From Human Embryonic Stem Cells," *Nature Biotechnology*, 2001; 19:1129-1133.

Zhang, X. et al., "Efficient Adeno-Associated Virus-Mediated Gene Expression in Human Placenta-Derived Mesenchymal Cells," *Microbiol. Immunol.*, 2003; 47(1):109-116.

Zhang, Y. et al., "Comparison of Mesenchymal Stem Cells from Human Placenta and Bone Marrow," *Chinese Medical Journal*, 2004; 117(6):882-887.

Zhang, Z.G. et al., "Correlation of VEGF and Angiopoietin Expression with Disruption of Blood-Brain Barrier and Angiogenesis after Focal Cerebral Ischemia," *J. Cereb. Blood Flow Metab.*, 2002; 22(4):379-392.

Zimmerman, S. et al., "Lack Of Telomerase Activity In Human Mesenchymal Stem Cells," *Leukemia*, 2003; 17:1146-1149.

Zuloff-Shani, A. et al., "Macrophage Suspensions Prepared From A Blood Unit for Treatment Of Refractory Human Ulcers," *Transfus. Apheresis Sci.*, 2004; 30:163-167.

\* cited by examiner

Serum Creatinine

REPAIR AND REGENERATION OF RENAL TISSUE USING HUMAN UMBILICAL CORD TISSUE-DERIVED CELLS

CROSS-REFERENCE TO RELATED APPLICATIONS

This application claims benefit to U.S. Provisional Patent Application No. 60/977,775, filed Oct. 5, 2007, the contents of which are incorporated by reference herein, in their entirety.

FIELD

The invention relates generally to the field of cell-based therapeutics. More specifically, the invention relates to the use of umbilical cord tissue-derived cells to repair and regenerate diseased or damaged kidneys.

BACKGROUND

Various publications, including patents, published applications, technical articles and scholarly articles are cited throughout the specification. Each of these cited publications is incorporated by reference herein, in its entirety and for all purposes.

Kidney disease is a serious, unmet medical condition with an annual U.S. cost burden exceeding $27 billion. Currently, more than 40 million Americans are at risk for or have kidney disease, and the incidence is increasing at an alarming rate of 6% per year. Therefore, by the year 2020, an estimated one in four people will have end-stage renal disease (ESRD), requiring either dialysis or kidney transplantation. To alleviate these economic and medical challenges, novel, transformational technologies for the treatment of both acute renal failure (ARF) and chronic kidney disease (CKD) are necessary.

Acute renal failure, also referred to as acute tubular necrosis, is a common syndrome affecting up to 7% of all hospitalized patients (Kelly et al. (2000) *Semin. Nephrol.* 1:4-19). ARF is the sudden loss of the ability of the kidneys to excrete wastes, concentrate urine, and conserve electrolytes. ARF most often occurs after an individual is exposed to nephrotoxic agents or following an ischemic-reperfusion event. Other causes include infection, urinary tract obstruction and some blood and autoimmune disorders. These insults induce damage to the functional component of the kidney, the nephron. More specifically, cells of the proximal tubule become necrotic. The tubule cells then detach from the tubular basement membrane, obstructing the tubular lumen. This obstruction leads to an increase in intratubular pressure, causing filtrate leakage from the nephron into the surrounding renal parenchyma. The reduction in nephron function and the accumulation of filtrate in the kidney tissue leads to a decrease in the rate of glomerular filtration, and ultimately renal failure ensues. Although ARF is a serious, life-threatening disorder, it is reversible.

Several therapeutic methods have been proposed, aimed at reducing or eliminating ARF. Most notably, advanced dialysis techniques are frequently employed. Nonetheless, the mortality rate among dialysis-treated ARF patients still remains 30-80%, indicating that dialysis has little therapeutic value in treating ARF. (Morigi et al. (2004) *J. Am. Soc. Nephrol.* 15:1794-804). In addition, pharmacological-based therapies such as dopamine, furosmide, mannitol or atrial natriuretic peptide administration, have failed in clinical studies (Haug et al. (1993) *Transplantation* 55:766-772; Lieberthal and Nigam (2000) *Am. J. Physiol. Renal Physiol.* 278: F1-F12). These data suggest that the traditional strategy for developing an ARF therapy is inadequate and that a new rationale must be implemented.

Recovery of renal function following ARF is dependent on the replacement of necrotic tubular cells with functional tubular epithelium. After injury, tubules are capable of self repair, forming new proximal tubular cells to replace failing or necrotic cells. The origin of the progenitor cells that give rise to new tubular cells is unknown. However, it is possible that tubular regeneration follows the stem cell/transit-amplifying cell paradigm described for more rapidly regenerating organ systems.

Recent studies have demonstrated that bone marrow-derived mesenchymal stem cells (MSCs) are renotropic and help to repair the kidneys after drug- and ischemia-induced ARF (Morigi et al. 2004). It has also been recently shown that intracarotid administration of $1 \times 10^6$ MSCs per rat with ischemia/reperfusion injury resulted in significantly improved renal function (Togel et al. (2005) *Am. J. Physiol. Renal Physiol.* 289(1):F31-42). It was further shown that the protective effects of MSCs were independent of stem cell differentiation, but rather were the result of secretion of renoprotective trophic factors.

In contrast to ARF, chronic kidney disease (CKD) is a gradual and progressive loss of kidney function. It is generally irreversible and ultimately leads to end-stage renal disease. In the United States, CKD is becoming increasingly common and is associated with poor health outcomes and high medical costs. The National Kidney Foundation estimates that 20 million Americans have CKD, and at least 20 million additional people are at risk for developing CKD. If left untreated, CKD can lead to significant morbidity and mortality from anemia, electrolyte imbalances, bone disease, cardiovascular disease, and kidney failure.

Progressive renal disease results from a combination of the initial disease injury (e.g, hypertension), followed by a maladaptive renal response to that injury. Such a response includes the production of pro-inflammatory and pro-fibrotic cytokines and growth factors. Therefore, one strategy to slow CKD progression is to ameliorate the inflammatory and fibrotic response as well as repair or reverse existing kidney damage. It has been shown that the administration of growth factors can slow CKD progression. For example, bone morphogenic protein-7 (BMP-7) prevented tubular atrophy, interstitial inflammation and fibrosis in rats with unilateral ureteric obstruction. Similarly, BMP-7 administration reduced tubulointerstitial fibrosis and glomerulosclerosis in the MRL lpr/lpr mouse model of lupus nephritis. In addition, hepatocyte growth factor has been shown to have potent anti-inflammatory and anti-fibrotic efficacy in a wide variety of animal models of kidney injury. Other factors that have shown therapeutic promise include transforming growth factor-$\beta$1, vascular endothelial growth factor (VEGF), connective tissue growth factor, fibroblast growth factor-2 (FGF-2), Interleukins, tumor necrosis factor, and monocyte chemotactic protein-1. These studies all demonstrate that the administration of growth factors is a promising therapeutic approach for the preventative treatment of CKD.

Despite existing medical treatment options, mortality rates remain very high and the incidence of kidney disease is on the rise. Therefore, a need exists in the art for an improved, potentially curative therapy. Today, no therapeutic intervention attempts to halt or even reverse kidney disease progression. The present invention provides therapeutic methods that show great renoprotective promise, and promote endogenous renal regeneration, replace necrotic renal cells and ultimately prevent ESRD.

SUMMARY

In accordance with one aspect, the invention provides methods for treating a patient having a disease of or damage to at least one kidney. For example, the damage to the kidney may be induced by age, trauma, toxin exposure, drug exposure, radiation exposure, oxidation, immune-complex deposition, or transplant rejection. The methods comprise administration to the patient of umbilical cord tissue-derived cells in an amount effective to treat the disease or damage. The umbilical cord tissue from which the cells are obtained is preferably substantially free of blood. The umbilical cord tissue-derived cells are preferably capable of self-renewal and expansion in culture and have the potential to differentiate, for example, to a kidney phenotype; require L-valine for growth; can grow in at least about 5% oxygen; do not produce CD117 or HLA-DR; express alpha smooth muscle actin; and express, relative to a human fibroblast, mesenchymal stem cell, or iliac crest bone marrow cell increased levels of interleukin 8, or reticulon 1. In some embodiments, the umbilical cord tissue-derived cells express oxidized low density lipoprotein receptor 1, reticulon, chemokine receptor ligand 3, and/or granulocyte chemotactic protein 2. In preferred aspects, the umbilical cord tissue-derived cells express CD10, CD13, CD44, CD73, and CD90. In some embodiments, the umbilical cord tissue-derived cells are induced in vitro to differentiate into renal lineage cells prior to administration to the patient. The umbilical cord tissue-derived cells may be genetically engineered to express a gene product that promotes repair and/or regeneration of kidney tissue. In some embodiments of the invention, the umbilical cord tissue-derived cells are administered with at least one other cell type, such as but not limited to a proximal tubule epithelial cell, loop of Henle epithelial cell, distal tubule cell, collecting duct cell, glomerulus parietal cell, glomerulus podocyte, mesangial cell, vascular endothelial cell, intersticial cell, or other multipotent or pluripotent stem cell. The at least one other cell type may be administered simultaneously with, or before, or after, the umbilical cord tissue-derived cells. In some aspects of the invention, the umbilical cord tissue-derived cells are administered with at least one agent. The agent may be administered simultaneously with, before, or after administration of the umbilical cord tissue-derived cells. In some preferred aspects of the invention, the umbilical cord tissue-derived cells exert a trophic effect on the kidney of the patient. In accordance with some aspects of the invention, the cells may be administered by injection or infusion. In some embodiments, the cells are administered encapsulated within an implantable device. In some embodiments of the invention, the cells are administered by implantation of a device comprising the cells.

In accordance with another aspect, the invention provides methods of treating a patient having a disease of or damage to at least one kidney by administering to the patient a composition comprising a soluble cell fraction, lysate, extracellular matrix, or conditioned medium prepared from umbilical cord tissue-derived cells, wherein the umbilical cord tissue is substantially free of blood, and wherein the cells are capable of self-renewal and expansion in culture and have the potential to differentiate; require L-valine for growth; can grow in at least about 5% oxygen; do not produce CD117 or HLA-DR; express alpha smooth muscle actin; and express, relative to a human fibroblast, mesenchymal stem cell, or iliac crest bone marrow cell increased levels of interleukin 8, or reticulon 1.

In accordance with another aspect, the present invention provides pharmaceutical compositions for treating a patient having a disease of or damage to at least one kidney, the composition comprising a pharmaceutically acceptable carrier and umbilical cord tissue-derived cells in an amount effective to treat the disease or injury, wherein the umbilical cord tissue is substantially free of blood, and wherein the cells are capable of self-renewal and expansion in culture and have the potential to differentiate; require L-valine for growth; can grow in at least about 5% oxygen; do not produce CD117 or HLA-DR; express alpha smooth muscle actin; and express, relative to a human fibroblast, mesenchymal stem cell, or iliac crest bone marrow cell increased levels of interleukin 8, or reticulon 1. In some embodiments, the damage to the kidney may be caused by age, trauma, toxin exposure, drug exposure, radiation exposure, oxidation, immune-complex deposition, or transplant rejection. In some embodiments, the umbilical cord tissue-derived cells are induced in vitro to differentiate into renal lineage cells prior to formulation of the composition. In some embodiments, the umbilical cord tissue-derived cells are genetically engineered to express a gene product that promotes repair and/or regeneration of kidney tissue. In some embodiments, the pharmaceutical composition includes at least one other cell type. The at least one other cell type may be but is not limited to a proximal tubule epithelial cell, loop of Henle epithelial cell, distal tubule cell, collecting duct cell, glomerulus parietal cell, glomerulus podocyte, mesangial cell, vascular endothelial cell, intersticial cell, or other multipotent or pluripotent stem cell. In some preferred embodiments, the pharmaceutical composition further includes at least one agent. In some preferred embodiments, the pharmaceutical composition is formulated for administration by injection or infusion. In some preferred embodiments of the pharmaceutical composition of the invention, the umbilical cord tissue-derived cells are encapsulated within an implantable device. In some embodiments of the pharmaceutical composition of the invention, the cells are seeded on a matrix.

In accordance with another aspect, the present invention provides pharmaceutical compositions for treating a patient having a disease of or damage to at least one kidney, comprising a pharmaceutically acceptable carrier and a lysate, extracellular matrix, or conditioned medium prepared from umbilical cord tissue-derived cells, wherein the umbilical cord tissue is substantially free of blood, and wherein the cells are capable of self-renewal and expansion in culture and have the potential to differentiate; require L-valine for growth; can grow in at least about 5% oxygen; do not produce CD117 or HLA-DR; express alpha smooth muscle actin; and express, relative to a human fibroblast, mesenchymal stem cell, or iliac crest bone marrow cell increased levels of interleukin 8, or reticulon 1.

In accordance with another aspect, the invention provides kits for treating a patient having a disease of or damage to at least one kidney, comprising a pharmaceutically acceptable carrier, umbilical cord tissue-derived cells in an amount effective to treat the disease or injury, wherein the umbilical cord tissue is substantially free of blood, and wherein the cells are capable of self-renewal and expansion in culture and have the potential to differentiate; require L-valine for growth; can grow in at least about 5% oxygen; do not produce CD117 or HLA-DR; express alpha smooth muscle actin; and express, relative to a human fibroblast, mesenchymal stem cell, or iliac crest bone marrow cell increased levels of interleukin 8, or reticulon 1, and instructions for using the kit in a method for treating a patient having a disease of or damage to at least one kidney. In some embodiments, the kit includes at least one reagent for and instructions for culturing the cells. In some embodiments, the kit includes a population of at least one other cell type. In some embodiments, the kit includes at least one agent.

Also provided by the present invention are kits for treating a patient having a disease of or damage to at least one kidney, comprising a pharmaceutically acceptable carrier, a lysate, extracellular matrix, or conditioned medium prepared from umbilical cord tissue-derived cells obtained from human umbilical cord tissue, wherein the umbilical cord tissue is substantially free of blood, and wherein the cells are capable of self-renewal and expansion in culture and have the potential to differentiate; require L-valine for growth; can grow in at least about 5% oxygen; do not produce CD117 or HLA-DR; express alpha smooth muscle actin; and express, relative to a human fibroblast, mesenchymal stem cell, or iliac crest bone marrow cell increased levels of interleukin 8, or reticulon 1, and instructions for using the kit components in a method for treating a patient having a disease or damage to at least one kidney.

The foregoing and other features and advantages of the invention will be apparent from the following, more particular description of preferred embodiments of the invention, as illustrated in the accompanying drawings.

DETAILED DESCRIPTION

Figure 1:
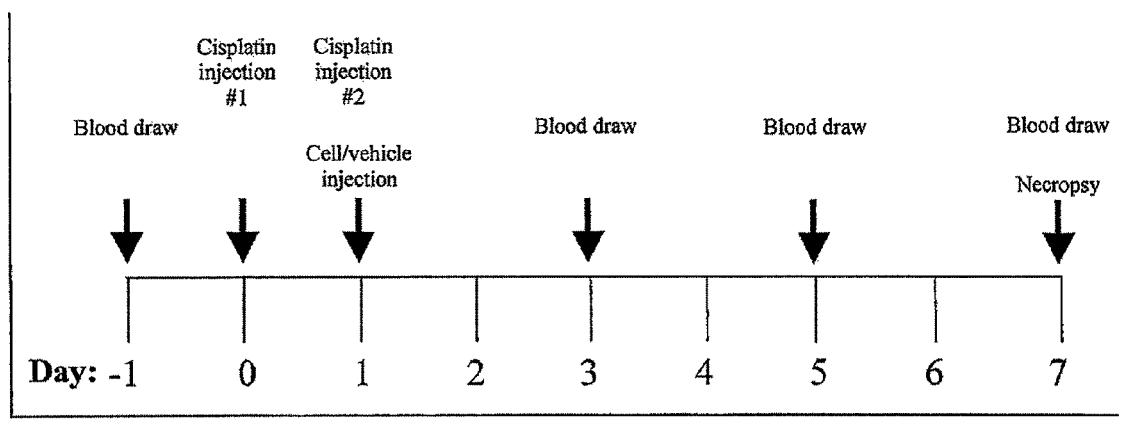
FIG. 1 shows the timeline for the execution of kidney damage and repair experimentation. Bold arrows denote time at which either cisplatin, cells or HBSS vehicle was injected, as well as when blood draws and necropsy occurred.

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

As used in this specification and the appended claims, the singular forms "a," "an," and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Derived" is used to indicate that the cells have been obtained from their biological source and grown, expanded in culture, immortalized, or otherwise manipulated in vitro.

"Isolated" means altered "by the hand of man" from the natural state. If a molecule or composition occurs in nature, it has been "isolated" if it has been changed or removed from its original environment, or both.

The term "express," "expressed," or "expression" of a nucleic acid molecule or gene refers to the biosynthesis of a gene product, for example, the biosynthesis of a polypeptide.

"Trophic factors" are substances that promote survival, growth, differentiation, proliferation and/or maturation of a cell, or stimulate increased biological activity of a cell.

"Damage" refers to any physical harm, injury, degeneration, or trauma to the kidney.

"Pathology" refers to any structural or functional indicia of a deviation from the normal state of a cell, tissue, organ, or system, as measured by any means suitable in the art.

A "disease" is any deviation from or impairment in the health, condition, or functioning of a cell, tissue, organ, system, or organism on the whole, as measured by any means suitable in the art.

A "primary disease" of the kidney is any disease that originates in, exclusively targets, substantially exclusively targets, or substantially targets the kidney.

A "secondary disease" of the kidney is any disease that is not a primary disease of the kidney. By way of example and not of limitation, such diseases may non-exclusively target, incidentally target, spread to, or otherwise affect the kidney. This term encompasses diseases of the kidney that arise from infections or diseases of other organs or systems of the body, or systemic diseases that induce, sustain, or enhance pathology to the kidneys.

"Renal" means of or relating to one or more kidneys.

"Treat," treating" or "treatment" refer to any success or indicia of success in the attenuation or amelioration of disease, damage, or condition, including any objective or subjective parameter such as abatement, remission, diminishing of symptoms or making the disease, damage, or condition more tolerable to the patient, slowing in the rate of degeneration or decline, making the final point of degeneration less debilitating, improving a subject's physical or mental well-being, or prolonging the length of survival. The treatment or amelioration of symptoms can be based on objective or subjective parameters; including the results of a physical examination, neurological examination, and/or psychiatric evaluations.

"Effective amount" or "therapeutically effective amount" are used interchangeably herein, and refer to an amount of a compound, material, or composition, as described herein effective to achieve a particular biological result such as, but not limited to, biological results disclosed, described, or exemplified herein. Such results may include, but are not limited to, the treatment of kidney disease or damage in a subject, as determined by any means suitable in the art.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

It has been discovered in accordance with the present invention that damaged kidneys can be repaired and regenerated by administration of umbilical cord tissue-derived cells, thereby reversing acute renal failure and enhancing the survival of animals that have suffered an insult to their kidneys. It has also further been discovered that administration of such cells to the animals normalized levels of blood urea nitrogen and serum creatinine in the injured animals. Accordingly, the invention features methods for treating subjects having a disease of or damage to at least one kidney. In general, the methods comprise administering to the subject a therapeutically effective amount of umbilical cord tissue-derived cells such that repair and/or regeneration of the afflicted kidney(s) occurs.

A mammalian umbilical cord can be recovered upon or shortly after termination of either a full-term or pre-term pregnancy, for example, following expulsion after birth or surgical removal following a Cesarean section. Blood and debris are removed from the umbilical cord tissue prior to isolation of cells, for example, by washing with any suitable medium or buffer.

Cells can be isolated from umbilical cord tissue by mechanical force or by enzymatic digestion. Preferred enzymes are metalloproteases, neutral proteases and mucolytic proteases. For example, various combinations of collagenase, dispase, and hyaluronidase can be used to dissociate cells from the umbilical cord tissue. The skilled artisan will appreciate that many such enzyme treatments are known in the art for isolating cells from various tissue sources. For example, the LIBERASE® Blendzyme (Roche) series of enzyme combinations are suitable for use in the instant methods. Other sources of enzymes are known, and the skilled artisan may also obtain such enzymes directly from their natural sources. The skilled artisan is also well-equipped to assess new, or additional enzymes or enzyme combinations for their utility in isolating the cells of the invention. Preferred enzyme treatments are 0.5, 1, 1.5, or 2 hours long or longer.

Isolated cells can be used to initiate cell cultures. Isolated cells are transferred to sterile tissue culture vessels either uncoated or coated with extracellular matrix or ligands such as laminin, collagen (native, denatured or crosslinked), gelatin, fibronectin, and other extracellular matrix proteins. Umbilical cord tissue-derived cells are cultured in any culture medium capable of sustaining growth of the cells such as, but not limited to, DMEM (high or low glucose), advanced DMEM, DMEM/MCDB 201, Eagle's basal medium, Ham's F10 medium (F10), Ham's F-12 medium (F12), Hayflick's Medium, Iscove's modified Dulbecco's medium, Mesenchymal Stem Cell Growth Medium (MSCGM), DMEM/F12, RPMI 1640, and CELL-GRO-FREE. The culture medium can be supplemented with one or more components including, for example, fetal bovine serum, preferably about 2-15% (v/v); equine serum; human serum; fetal calf serum; beta-mercaptoethanol, preferably about 0.001% (v/v); one or more growth factors, for example, platelet-derived growth factor (PDGF), epidermal growth factor (EGF), fibroblast growth factor (FGF), vascular endothelial growth factor (VEGF), insulin-like growth factor-1 (IGF-1), leukocyte inhibitory factor (LIF) and erythropoietin; amino acids, including L-valine; and one or more antibiotic and/or antimycotic agents to control microbial contamination, such as, for example, penicillin G, streptomycin sulfate, amphotericin B, gentamicin, and nystatin, either alone or in combination.

The cells are seeded in culture vessels at a density to allow cell growth. In one embodiment, the cells are cultured at about 0 to about 5 percent by volume $CO_2$ in air. In some embodiments, the cells are cultured at about 2 to about 25 percent $O_2$ in air, preferably about 5 to about 20 percent $O_2$ in air. The cells preferably are cultured at about 25 to about 40° C. and more preferably are cultured at 37° C. The medium in the culture vessel can be static or agitated, for example, using a bioreactor. Umbilical cord tissue-derived cells are preferably grown under low oxidative stress (e.g., with addition of glutathione, Vitamin C, Catalase, Vitamin E, N-Acetylcysteine), meaning no or minimal free radical damage to the cultured cells.

Umbilical cord tissue-derived cells can be passaged, or removed to a separate culture vessel containing fresh medium of the same or a different type as that used initially, where the population of cells can be mitotically expanded. The cells of the invention may be used at any point between passage 0 and senescence. The cells preferably are passaged between about 3 and about 25 times, more preferably are passaged about 4 to about 12 times, and preferably are passaged 10 or 11 times. Cloning and/or subcloning may be performed to confirm that a clonal population of cells has been isolated.

Different cell types present in umbilical cord tissue can be fractionated into subpopulations. This may be accomplished using standard techniques for cell separation including, but not limited to, enzymatic treatment; cloning and selection of specific cell types, for example but not limited to selection based on morphological and/or biochemical markers; selective growth of desired cells (positive selection), selective destruction of unwanted cells (negative selection); separation based upon differential cell agglutinability in the mixed population as, for example, with soybean agglutinin; freeze-thaw procedures; differential adherence properties of the cells in the mixed population; filtration; conventional and zonal centrifugation; centrifugal elutriation (counter-streaming centrifugation); unit gravity separation; countercurrent distribution; electrophoresis; fluorescence activated cell sorting (FACS); and the like.

Examples of cells isolated from umbilical cord tissue were deposited with the American Type Culture Collection on Jun. 10, 2004, and assigned ATCC Accession Numbers as follows: (1) strain designation UMB 022803 (P7) was assigned Accession No. PTA-6067; and (2) strain designation UMB 022803 (P17) was assigned Accession No. PTA-6068.

Umbilical cord tissue-derived cells can be characterized by, for example, by growth characteristics (e.g., population doubling capability, doubling time, passages to senescence), karyotype analysis (e.g., normal karyotype; maternal or neonatal lineage), flow cytometry (e.g., FACS analysis), immunohistochemistry and/or immunocytochemistry (e.g., for detection of epitopes), gene expression profiling (e.g., gene chip arrays; polymerase chain reaction (for example, reverse transcriptase PCR, real time PCR, and conventional PCR)), protein arrays, protein secretion (e.g., by plasma clotting assay or analysis of PDC-conditioned medium, for example, by Enzyme Linked ImmunoSorbent Assay (ELISA)), mixed lymphocyte reaction (e.g., as measure of stimulation of PBMCs), and/or other methods known in the art.

In various aspects, the umbilical cord tissue-derived cells have one or more of the following growth features: require L-valine for growth in culture; are capable of growth in atmospheres containing oxygen from about 5% to at least about 20%; have the potential for at least about 40 doublings in culture before reaching senescence; and attach and expand on a coated or uncoated tissue culture vessel, wherein the coated tissue culture vessel comprises a coating of gelatin, laminin, collagen, polyornithine, vitronectin or fibronectin.

In certain embodiments the cells have a normal karyotype, which is maintained as the cells are passaged. Karyotyping is particularly useful for identifying and distinguishing neonatal from maternal cells derived from placenta. Methods for karyotyping are available and known to those of skill in the art.

In other embodiments, the cells can be characterized by production of certain proteins, including production of at least one of tissue factor, vimentin, and alpha-smooth muscle actin; and production of at least one of CD10, CD13, CD44, CD73, CD90, PDGFr-alpha, PD-L2 and HLA-A,B,C cell surface markers, as detected by flow cytometry. In other embodiments, the cells may be characterized by lack of production of at least one of CD31, CD34, CD45, CD80, CD86, CD117, CD141, CD178, B7-H2, HLA-G, and HLA-DR, HLA-DP, and/or HLA-DQ cell surface markers, as detected by any suitable means such as flow cytometry. Particularly preferred are cells that produce at least two of tissue factor, vimentin, and alpha-smooth muscle actin. More preferred are those cells producing all three of the proteins tissue factor, vimentin, and alpha-smooth muscle actin.

In other embodiments, the cells have, relative to a human cell that is a fibroblast, a mesenchymal stem cell, or an iliac crest bone marrow cell, increased expression of a gene encoding at least one of interleukin 8; reticulon 1; chemokine (C-X-C motif) ligand 1 (melonoma growth stimulating activity, alpha); chemokine (C-X-C motif) ligand 6 (granulocyte chemotactic protein 2); chemokine (C-X-C motif) ligand 3; tumor necrosis factor, alpha-induced protein 3.

In yet other embodiments, the cells have, relative to a human cell that is a fibroblast, a mesenchymal stem cell, or an iliac crest bone marrow cell, reduced expression of a gene encoding at least one of: short stature homeobox 2; heat shock 27 kDa protein 2; chemokine (C-X-C motif) ligand 12 (stromal cell-derived factor 1); elastin (supravalvular aortic stenosis, Williams-Beuren syndrome); Homo sapiens mRNA; cDNA DKFZp586M2022 (from clone DKFZp586M2022); mesenchyme homeo box 2 (growth arrest-specific homeo box); sine oculis homeobox homolog 1 (Drosophila); crystallin, alpha B; disheveled associated activator of morphogenesis 2; DKFZP586B2420 protein; similar to neuralin 1; tetranectin (plasminogen binding protein); src homology three (SH3) and cysteine rich domain; cholesterol 25-hydroxylase; runt-related transcription factor 3; interleukin 11 receptor, alpha; procollagen C-endopeptidase enhancer; frizzled homolog 7 (Drosophila); hypothetical gene BC008967; collagen, type VIII, alpha 1; tenascin C (hexabrachion); iroquois homeobox protein 5; hephaestin; integrin, beta 8; synaptic vesicle glycoprotein 2; neuroblastoma, suppression of tumorigenicity 1; insulin-like growth factor binding protein 2, 36 kDa; Homo sapiens cDNA FLJ12280 fis, clone MAMMA 1001744; cytokine receptor-like factor 1; potassium intermediate/small conductance calcium-activated channel, subfamily N, member 4; integrin, beta 7; transcriptional co-activator with PDZ-binding motif (TAZ); sine oculis homeobox homolog 2 (Drosophila); KIAA1034 protein; vesicle-associated membrane protein 5 (myobrevin); EGF-containing fibulin-like extracellular matrix protein 1; early growth response 3; distal-less homeo box 5; hypothetical protein FLJ20373; aldo-keto reductase family 1, member C3 (3-alpha hydroxysteroid dehydrogenase, type II); biglycan; transcriptional co-activator with PDZ-binding motif (TAZ); fibronectin 1; proenkephalin; integrin, beta-like 1 (with EGF-like repeat domains); Homo sapiens mRNA full length insert cDNA clone EUROIMAGE 1968422; EphA3; KIAA0367 protein; natriuretic peptide receptor C/guanylate cyclase C (atrionatriuretic peptide receptor C); hypothetical protein FLJ14054; Homo sapiens mRNA; cDNA DKFZp564B222 (from clone DKFZp564B222); BCL2/adenovirus E1B 19 kDa interacting protein 3-like; AE binding protein 1; and cytochrome c oxidase subunit VIIa polypeptide 1 (muscle).

In some embodiments, the cells can be characterized by secretion of at least one of MCP-1, IL-6, IL-8, GCP-2, HGF, KGF, FGF, HB-EGF, BDNF, TPO, MIP1b, 1309, MDC, RANTES, and TIMP1. In some embodiments, the cells can be characterized by lack of secretion of at least one of TGF-beta2, ANG2, PDGFbb, MIP1b, and VEGF, as detected by ELISA.

In preferred embodiments, the cell comprises two or more of the above-listed growth, protein/surface marker production, gene expression or substance-secretion characteristics. More preferred are those cells comprising, three, four, or five or more of the characteristics. Still more preferred are cells comprising six, seven, or eight or more of the characteristics. Still more preferred are those cells comprising all of above characteristics.

Among cells that are preferred for use with the various aspects of the invention are cells having the characteristics described above and more particularly those wherein the cells have normal karyotypes and maintain normal karyotypes with passaging, and further wherein the cells express each of the markers CD10, CD13, CD44, CD73, CD90, PDGFr-alpha, and HLA-A,B,C, wherein the cells produce the immunologically-detectable proteins which correspond to the listed markers. Still more preferred are those cells which in addition to the foregoing do not produce proteins corresponding to any of the markers CD31, CD34, CD45, CD117, CD141, or HLA-DR,DP,DQ, as detected by any means suitable in the art, such as flow cytometry. Highly preferred are cells that do not express CD117 or HLA-DR.

In highly preferred aspects, the methods comprise administering cells obtained or isolated from human umbilical cord tissue to a subject in need of treatment for at least one diseased or damaged kidney, wherein the cells are capable of self-renewal and expansion in culture, require L-valine for growth, can grow in at least about 5% oxygen, do not produce CD117 or HLA-DR, express alpha smooth muscle actin, and express, relative to a human fibroblast, mesenchymal stem cell, or iliac crest bone marrow cell increased levels of interleukin 8, or reticulon 1. Cells isolated from human umbilical cord tissue may be expanded in culture prior to administration. In some embodiments, the cells obtained from human umbilical cord tissue have the potential to differentiate into cells of at least a kidney phenotype. Expression of Pax-2, a transcription factor expressed by renal epithelial progenitor cells, may be used to identify differentiation of the umbilical cord tissue-derived cells to a kidney phenotype or renal cell lineage. Renal cell differentiation of the umbilical cord tissue-derived cells also is demonstrated by tubulogenesis and branching morphogenesis in three-dimensional collagen gels.

Certain cells having the potential to differentiate along lines leading to various phenotypes are unstable and thus can spontaneously differentiate. Presently preferred for use with the invention are cells that do not spontaneously differentiate, for example, along kidney cell lines. Preferred cells, when grown in Growth Medium, are substantially stable with respect to the cell markers produced on their surface, and with respect to the expression pattern of various genes, for example as determined using gene expression profiling, for example, by using nucleic acid or polypeptide arrays. The cells remain substantially constant, for example in their surface marker characteristics over passaging, through multiple population doublings.

In the inventive methods, the umbilical cord tissue-derived cells can be administered in conjunction with other therapeutic cells, and/or with a biologically active agent, such as antithrombogenic agents, anti-apoptotic agents, anti-inflammatory agents, immunosuppressants (e.g., cyclosporine, rapamycin), antioxidants, or other agents ordinarily used in the art to treat kidney damage or disease such as eprodisate and triptolide. Umbilical cord tissue-derived cells may be administered in conjunction with an HMG-CoA reductase inhibitor, including but not limited to simvastatin, pravastatin, lovastatin, fluvastatin, cerivastatin, and atorvastatin. The umbilical cord tissue-derived cells can be administered in sequence with, or co-administered with the other cells or agent. Lysates, soluble cell fractions, membrane-enriched cell fractions, cell culture media (e.g., conditioned media), or extracellular matrix derived from umbilical cord tissue-derived cells can also be administered to patients as appropriate, including co-administered with umbilical cord tissue-derived cells themselves, and additional cells or agents. The particular agent chosen can be at the discretion of the medical professional directing the treatment of the patient, and can vary according to the particular needs or condition of the patient. The agent chosen can be used for various purposes such as, but not limited to, facilitating the administration of the cells, improving the repair and/or regeneration of the kidney, improving the overall health of the patient, reducing pain, reducing or preventing rejection of the transplanted cells, and the like.

The facilitation of repair and regeneration of kidney tissue may be by way of trophic factors secreted by the umbilical cord tissue-derived cells. For example, renoprotective efficacy may be conferred through umbilical cord tissue-derived cell paracrine or trophic factor mediated mechanisms. Such factors include, for example, hepatocyte growth factor (HGF), bone morphogenic protein-7 (BMP-7), transforming growth factor beta (TGF-$\beta$), matrix metalloproteinase-2 (MMP-2), and basic fibroblast growth factor (bFGF). Administration of umbilical cord tissue-derived cells may provide a continuous release of one or more renoprotective factors. The trophic support or release of renoprotective factors by the umbilical cord tissue-derived cells may used in place of or in addition to administration of one or more renoprotective factors.

The methods have utility to treat kidney damage. The methods have utility for treating kidney damage including acute kidney failure or injury or chronic kidney disease resulting in morbidity or reduced life expectancy. Some non-limiting examples of damage that can be repaired and reversed by the invention include surgical removal of any portion (or all) of the kidney, drug-induced damage, toxin-induced damage, radiation-induced damage, environmental exposure-induced damage, sonic damage, heat damage, hypoxic damage, oxidation damage, viral damage, age or senescence-related damage, inflammation-induced damage, immune cell-induced damage, for example, transplant rejection, immune complex-induced damage, and the like. Five major drug categories associated with renal pathology are drugs that target hemodynamic, metabolic, fibrotic, inflammatory, or immunomodulatory processes. Umbilical cord tissue-derived cells may exert their effect by acting on one or more of these physiological processes.

The cells can be administered as a pharmaceutical/therapeutic cell composition that comprises a pharmaceutically-acceptable carrier and umbilical cord tissue-derived cells as described and exemplified herein. Therapeutic cell compositions can comprise umbilical cord tissue-derived cells induced to differentiate along a kidney cell pathway or lineage. The therapeutic cell compositions can comprise cells or cell products that stimulate cells in the patient's kidney to divide, differentiate, or both. It is preferred that the therapeutic cell composition induce, facilitate, or sustain repair and/or regeneration of the kidneys in the patient to which they are administered.

The cells can be administered to the patient by injection. For example, the cells can be injected directly into one or both kidneys of the patient, or can be injected onto the surface of the kidney, into an adjacent area, or even to a more remote area with subsequent migration to the patient's kidneys. In some preferred aspects, the cells can home to the diseased or damaged area. Particularly preferred are cells that can be injected intravenously and locate appropriately to the desired site of action, for example, kidney cells or their progenitors preferably are capable of locating and homing to the kidney or its structures or substructures.

The cells can also be administered in the form of a device such as a matrix-cell complex. Device materials include but are not limited to bioresorbable materials such as collagens, 35/65 Poly(epsilon-caprolactone)(PCL)/Poly(glycolic acid) (PGA), Panacryl™ bioabsorbable constructs, Vicryl™ polyglactin 910, and self-assembling peptides and non-resorbable materials such as fluoropolymers (e.g., Teflon® fluoropolymers), plastic, and metal. Matrices include biocompatible scaffolds, lattices, self-assembling structures and the like, whether bioabsorbable or not, liquid, gel, or solid. Such matrices are known in the arts of therapeutic cell treatment, surgical repair, tissue engineering, and wound healing. Preferably the matrices are pretreated with the therapeutic cells. More preferably the matrices are populated with cells in close association to the matrix or its spaces. The cells can adhere to the matrix or can be entrapped or contained within the matrix spaces. Most preferred are matrix-cell complexes in which the cells are growing in close association with the matrix and when used therapeutically, growth, repair, and/or regeneration of the patient's own kidney cells is stimulated and supported, and proper angiogenesis is similarly stimulated or supported. The matrix-cell compositions can be introduced into a patient's body in any way known in the art, including but not limited to implantation, injection, surgical attachment, transplantation with other tissue, and the like. In some embodiments, the matrices form in vivo, or even more preferably in situ, for example in situ polymerizable gels can be used in accordance with the invention. Examples of such gels are known in the art.

The cells of the invention can also be seeded onto such three-dimensional matrices, such as scaffolds and implanted in vivo, where the seeded cells may proliferate on or in the framework, or help to establish replacement tissue in vivo with or without cooperation of other cells. Growth of umbilical cord tissue-derived cells on the three-dimensional framework preferably results in the formation of a three-dimensional tissue, or foundation thereof, which can be utilized in vivo, for example to repair and/or regenerate damaged or diseased tissue. For example, the three-dimensional scaffolds can be used to form tubular structures, for example for use in repair of renal blood vessels, or various other aspects of the renal system or kidney structures.

The cells can be seeded on a three-dimensional framework or matrix, such as a scaffold, a foam or hydrogel and administered accordingly. The framework can be configured into various shapes such as substantially flat, substantially cylindrical or tubular, or can be completely free-form as may be required or desired for the corrective structure under consideration. Two or more substantially flat frameworks can be laid atop another and secured together as necessary to generate a multilayer framework.

In some aspects, the cells grow on the three dimensional structure, and in some aspects, the cells only survive, or even die, although in doing so they stimulate or promote repair and regeneration of kidney tissue, for example, and preferably facilitate or sustain vascularization.

On such three-dimensional frameworks, the cells can be co-administered with other kidney cell types, or other soft tissue type progenitors, including stem cells. When grown in this three-dimensional system, the proliferating cells mature and segregate properly to form components of adult tissues analogous to counterparts found naturally in vivo.

The matrices described and exemplified herein can be designed such that the matrix structure supports the umbilical cord tissue-derived cells without subsequent degradation, supports the cells from the time of seeding until the tissue transplant is remodeled by the host tissue, or allows the seeded cells to attach, proliferate, and develop into a tissue structure having sufficient mechanical integrity to support itself in vitro, at which point, the matrix is degraded.

The matrices, scaffolds, foams and self-assembling systems contemplated for use herein can be implanted in combination with any one or more cells, growth factors, drugs, or other components, such as bioactive agents that promote healing, regeneration, repair, or in-growth of tissue, or stimulate vascularization or innervation thereof or otherwise enhance or improve the therapeutic outcome or the practice of the invention, in addition to the cells of the invention. In one preferred aspect, a device comprising one or more HMG CoA reductase inhibitors is seeded with umbilical cord tissue-derived cells. The HMG CoA reductase inhibitor may be pumped to the device. One or more HMG CoA reductase inhibitors may be incorporated into the device. In some embodiments, a device seeded with the cells of the invention is treated with one or more HMG CoA reductase inhibitors. The device may be implanted in vivo.

The cells can be grown freely in culture, removed from the culture and inoculated onto a three-dimensional framework. Inoculation of the three-dimensional framework with a concentration of cells, e.g., approximately $10^6$ to $5\times10^7$ cells per milliliter, preferably results in the establishment of the three-dimensional support in relatively shorter periods of time. Moreover in some application it may be preferable to use a greater or lesser number of cells depending on the result desired.

In some aspects, it is useful to re-create in culture the cellular microenvironment found in vivo, such that the extent to which the cells are grown prior to implantation in vivo or used in vitro may vary. The cells can be inoculated onto the framework before or after forming the shape desired for implantation, e.g., ropes, tubes, filaments, and the like. Following inoculation of the cells onto the framework, the framework is preferably incubated in an appropriate growth medium. During the incubation period, the inoculated cells will grow and envelop the framework and may for example bridge, or partially bridge any interstitial spaces therein. It is preferable, but not required to grow the cells to an appropriate degree which reflects the in vivo cell density of the kidney tissue being repaired or regenerated. In other embodiments, the presence of the cells, even in low numbers on the framework encourages in-growth of endogenous healthy cells to facilitate healing for example of the damaged or injured tissue.

Examples of matrices, for example scaffolds which may be used for aspects of the invention include mats (woven, knitted, and more preferably nonwoven) porous or semiporous foams, self assembling peptides and the like. Nonwoven mats may, for example, be formed using fibers comprised of natural or synthetic polymers. In a preferred embodiment, absorbable copolymers of glycolic and lactic acids (PGA/PLA), sold under the tradename VICRYL® (Ethicon, Inc., Somerville, N.J.) are used to form a mat. Foams, composed of, for example, poly(epsilon-caprolactone)/poly(glycolic acid) (PCL/PGA) copolymer, formed by processes such as freeze-drying, or lyophilization, as discussed in U.S. Pat. No. 6,355,699, can also serve as scaffolds. Gels also form suitable matrices, as used herein. Examples include in situ polymerizable gels, and hydrogels, for example composed of self-assembling peptides. These materials are frequently used as supports for growth of tissue. In situ-forming degradable networks are also suitable for use in the invention (see, e.g., Anseth, K. S. et al., 2002, *J. Controlled Release* 78: 199-209; Wang, D. et al., 2003, *Biomaterials* 24: 3969-3980; U.S. Patent Publication 2002/0022676 to He et al.). These materials are formulated as fluids suitable for injection, then may be induced by a variety of means (e.g., change in temperature, pH, exposure to light) to form degradable hydrogel networks in situ or in vivo.

The framework can be a felt, which can be comprised of a multifilament yarn made from a bioabsorbable material, e.g., PGA, PLA, PCL copolymers or blends, or hyaluronic acid. The yarn is made into a felt using standard textile processing techniques consisting of crimping, cutting, carding and needling. Te cells of the invention can be seeded onto foam scaffolds that may be composite structures. In addition, the three-dimensional framework may be molded into a useful shape, such as a specific structure in or around the kidney to be repaired, replaced, or augmented.

The framework can be treated prior to inoculation of the cells of the invention in order to enhance cell attachment. For example, prior to inoculation with the cells of the invention, nylon matrices could be treated with 0.1 molar acetic acid and incubated in polylysine, PBS, and/or collagen to coat the nylon. Polystyrene could be similarly treated using sulfuric acid.

In addition, the external surfaces of the three-dimensional framework can be modified to improve the attachment or growth of cells and differentiation of tissue, such as by plasma coating the framework or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate), a cellular matrix, and/or other materials such as, but not limited to, gelatin, alginates, agar, agarose, and plant gums, among others.

The scaffold can be comprised of or treated with materials that render it non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as ePTFE, and segmented polyurethaneurea silicones, such as PUR-SPAN® (The Polymer Technology Group, Inc., Berkeley, Calif.). These materials can be further treated to render the scaffold non-thrombogenic. Such treatments include antithrombotic agents such as heparin, and treatments which alter the surface charge of the material such as plasma coating.

Different proportions of the various types of collagen, for example, deposited on the framework can affect the growth of tissue-specific or other cells which may be later inoculated onto the framework or which may grow onto the structure in vivo. Alternatively, the framework can be inoculated with a mixture of cells which synthesize the appropriate collagen types desired. Depending upon the tissue to be cultured, the appropriate collagen type to be inoculated on the framework or produced by the cells seeded thereon may be selected. For example, the relative amounts of collagenic and elastic fibers present in the framework can be modulated by controlling the ratio of collagen-producing cells to elastin-producing cells in the initial inoculum. For example, since the inner walls of arteries are rich in elastin, an arterial scaffold should contain a co-culture of smooth muscle cells which secrete elastin.

The seeded or inoculated three-dimensional framework of the invention can be for transplantation or implantation of either the cultured cells obtained from the matrix or the cultured matrix itself in vivo. The three-dimensional scaffolds may, according to the invention, be used to replace or augment existing tissue, to introduce new or altered tissue, to modify artificial prostheses, or to join together biological tissues or structures. For example and not by way of limitation, the three-dimensional framework can also be used to construct single and multi-layer tubular tissues in vitro that can serve as a replacement for damaged or diseased tubular tissue in vivo.

A scaffold can be cut into a strip (e.g., rectangular in shape) of which the width is approximately equal to the inner circumference of a tubular organ, for example, calyces or the ureter, into which it will ultimately be inserted. The cells can be inoculated onto the scaffold and incubated by floating or suspending in liquid media. At the appropriate stage of confluence, the scaffold can be rolled up into a tube by joining the long edges together. The seam can be closed by suturing the two edges together using fibers of a suitable material of an appropriate diameter.

According to the invention, a scaffold can be formed as a tube, inoculated with umbilical cord tissue-derived cells, and suspended in media in an incubation chamber. In order to prevent cells from occluding the lumen, one of the open ends of the tubular framework can be affixed to a nozzle. Liquid media can be forced through this nozzle from a source chamber connected to the incubation chamber to create a current through the interior of the tubular framework. The other open end can be affixed to an outflow aperture which leads into a collection chamber from which the media can be recirculated through the source chamber. The tube can be detached from the nozzle and outflow aperture when incubation is complete. This method is described by Ballermann, B. J., et al., Int. Application No. WO 94/25584 and in U.S. application Ser. No. 08/430,768, both of which are incorporated herein by reference in its entirety.

In general, two three-dimensional frameworks can be combined into a tube in accordance with the invention using any of the following methods. Two or more flat frameworks can be laid atop another and sutured together. This two-layer sheet can then be rolled up, and, as described above, joined together and secured.

One tubular scaffold that is to serve as the inner layer can be inoculated with umbilical cord tissue-derived cells and incubated. A second scaffold can be grown as a flat strip with width slightly larger than the outer circumference of the tubular framework. After appropriate growth is attained, the flat framework can be wrapped around the outside of the tubular scaffold followed by closure of the seam of the two edges of the flat framework and, preferably, securing the flat framework to the inner tube.

Two or more tubular meshes of slightly differing diameters can be grown separately. The framework with the smaller diameter can be inserted inside the larger one and secured.

For each of these methods, more layers can be added by reapplying the method to the double-layered tube. The scaffolds can be combined at any stage of growth of the umbilical cord tissue-derived cells, and incubation of the combined scaffolds can be continued when desirable.

The lumenal aspect of the tubular construct can be comprised of or treated with materials that render the lumenal surface of the tubular scaffold non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as ePTFE, and segmented polyurethaneurea silicones, such as PURSPAN® (The Polymer Technology Group, Inc., Berkeley, Calif.). These materials can be further treated to render the lumenal surface of the tubular scaffold non-thrombogenic. Such treatments include anti-thrombotic agents such as heparin, and treatments which alter the surface charge of the material such as plasma coating.

In some presently preferred embodiments, the methods comprise inducing the therapeutic postpartum-derived cells to differentiate along a kidney cell pathway, towards kidney cell phenotypes, or progenitors or more primitive relatives of the foregoing. The therapeutic cell compositions can integrate into the patient's kidney, or alternatively can provide support for growth or stimulation to differentiate for naturally present kidney stem cells. Therapeutic cells can be coadministered with cell lysates, or with other allogeneic, syngeneic or autologous cells. The survival of the cells delivered in administering the therapeutic cell compositions is not determinative of the success or results of their use, rather improvement in kidney health, or overall patient health is outcome determinative. Thus, the cells need not integrate with the patient's kidney, or even into blood vessels, but the indicia of improvements in kidney health in the patient before and after treatment preferably include at least one of objective measurements of kidney health such as but not limited to improvements made in serum or urinalysis for creatinine, urea, protein, blood urea nitrogen (BUN), and osmolarity tests, and subjective assessments (including self-assessment) of the patient's condition.

A successful treatment could thus comprise treatment of a patient with a disease, pathology, or trauma to the kidney with a therapeutic cell composition comprising the umbilical cord tissue-derived cells, in the presence or absence of another cell type. For example, and not by way of limitation, the cells preferably at least partially integrate, multiply, or survive in the patient. In other preferred embodiments, the patient experiences benefits from the therapy, for example from the ability of the cells to support the growth of other cells, including stem cells or progenitor cells present in the kidney, from the tissue in-growth or vascularization of the tissue, and from the presence of beneficial cellular factors, chemokines, cytokines and the like, but the cells do not integrate or multiply in the patient. In some aspects, the patient benefits from the therapeutic treatment with the cells, but the cells do not survive for a prolonged period in the patient. For example, in one embodiment, the cells gradually decline in number, viability or biochemical activity, in other embodiments, the decline in cells may be preceded by a period of activity, for example growth, division, or biochemical activity. In other embodiments, senescent, nonviable or even dead cells are able to have a beneficial therapeutic effect.

The administering is preferably in vivo by transplanting, implanting, injecting, fusing, delivering via catheter, or providing as a matrix-cell complex, or any other means known in the art for providing cell therapy.

In some aspects, the inventive methods can further comprise evaluating the patient for improvements in kidney structure and/or function, or improvements in overall health. Such evaluations can proceed according to any means suitable in the art, including those described and exemplified herein.

Also featured in accordance with the present invention are kits for practicing the inventive methods. In one aspect, kits for treating a patient having a disease of or damage to at least one kidney are provided. The kits comprise a pharmaceutically acceptable carrier, cells obtained from human umbilical cord tissue in an amount effective to treat the disease or injury, such as those cells that are described and exemplified herein, and instructions for using the kit in a method for treating a patient having a disease of or damage to at least one kidney. The kits may further comprise at least one reagent and instructions for culturing the cells. The kits may further comprise a population of at least one other cell type, and/or at least one agent.

In some aspects, the kits comprise a pharmaceutically acceptable carrier, a lysate, extracellular matrix, or conditioned medium prepared from cells obtained from human umbilical cord tissue, which cells have the characteristics that are described and exemplified herein. The kits have utility to facilitate the repair and/or regeneration of a kidney that is damaged or diseased.

The following examples are provided to describe the invention in greater detail. They are intended to illustrate, not to limit, the invention.

EXAMPLE 1

Isolation of Umbilical Cord Tissue-Derived Cells

Umbilical cords were obtained from National Disease Research Interchange (NDRI, Philadelphia, Pa.). The tissues were obtained following normal deliveries. The cell isolation protocol was performed aseptically in a laminar flow hood. To remove blood and debris, the cord was washed in phosphate buffered saline (PBS; Invitrogen, Carlsbad, Calif.) in the presence of antimycotic and antibiotic (100 units/milliliter penicillin, 100 micrograms/milliliter streptomycin, 0.25 micrograms/milliliter amphotericin B). The tissues were then mechanically dissociated in 150 $cm^2$ tissue culture plates in the presence of 50 milliliters of medium (DMEM-Low glucose or DMEM-High glucose; Invitrogen), until the tissue was minced into a fine pulp. The chopped tissues were transferred to 50 milliliter conical tubes (approximately 5 grams of tissue per tube). The tissue was then digested in either DMEM-Low glucose medium or DMEM-High glucose medium, each containing antimycotic and antibiotic as described above. In some experiments, an enzyme mixture of collagenase and dispase was used ("C:D;" collagenase (Sigma, St Louis, Mo.), 500 Units/milliliter; and dispase (Invitrogen), 50 Units/milliliter in DMEM:—Low glucose medium). In other experiments a mixture of collagenase, dispase and hyaluronidase ("C:D:H") was used (collagenase, 500 Units/milliliter; dispase, 50 Units/milliliter; and hyaluronidase (Sigma), 5 Units/milliliter, in DMEM:—Low glucose). The conical tubes containing the tissue, medium and digestion enzymes were incubated at 37° C. in an orbital shaker (Environ, Brooklyn, N.Y.) at 225 rpm for 2 hrs.

After digestion, the tissues were centrifuged at 150×g for 5 minutes, the supernatant was aspirated. The pellet was resuspended in 20 milliliters of Growth Medium (DMEM:Low glucose (Invitrogen), 15 percent (v/v) fetal bovine serum (FBS; defined bovine serum; Lot#AND 18475; Hyclone, Logan, Utah), 0.001% (v/v) 2-mercaptoethanol (Sigma), 1 milliliter per 100 milliliters of antibiotic/antimycotic as described above. The cell suspension was filtered through a 70-micrometer nylon cell strainer (BD Biosciences). An additional 5 milliliters rinse comprising Growth Medium was passed through the strainer. The cell suspension was then passed through a 40-micrometer nylon cell strainer (BD Biosciences) and chased with a rinse of an additional 5 milliliters of Growth Medium.

The filtrate was resuspended in Growth Medium (total volume 50 milliliters) and centrifuged at 150×g for 5 minutes. The supernatant was aspirated and the cells were resuspended in 50 milliliters of fresh Growth Medium. This process was repeated twice more.

Upon the final centrifugation supernatant was aspirated and the cell pellet was resuspended in 5 milliliters of fresh Growth Medium. The number of viable cells was determined using Trypan Blue staining. Cells were then cultured under standard conditions.

The cells isolated from umbilical cords were seeded at 5,000 cells/$cm^2$ onto gelatin-coated T-75 $cm^2$ flasks (Corning Inc., Corning, N.Y.) in Growth Medium with antibiotics/antimycotics as described above. After 2 days (in various experiments, cells were incubated from 2-4 days), spent medium was aspirated from the flasks. Cells were washed with PBS three times to remove debris and blood-derived cells. Cells were then replenished with Growth Medium and allowed to grow to confluence (about 10 days from passage 0) to passage 1. On subsequent passages (from passage 1 to 2 and so on), cells reached sub-confluence (75-85 percent confluence) in 4-5 days. For these subsequent passages, cells were seeded at 5000 cells/$cm^2$. Cells were grown in a humidified incubator with 5 percent carbon dioxide and atmospheric oxygen, at 37° C.

EXAMPLE 2

Evaluation of Human Postpartum-Derived Cell Surface Markers by Flow Cytometry

Umbilical cord tissue was characterized using flow cytometry to provide a profile for the identification of cells obtained therefrom.

Cells were cultured in Growth Medium (Gibco Carlsbad, Calif.) with penicillin/streptomycin. Cells were cultured in plasma-treated T75, T150, and T225 tissue culture flasks (Corning, Corning, N.Y.) until confluent. The growth surfaces of the flasks were coated with gelatin by incubating 2% (w/v) gelatin (Sigma, St. Louis, Mo.) for 20 minutes at room temperature.

Adherent cells in flasks were washed in PBS and detached with Trypsin/EDTA. Cells were harvested, centrifuged, and resuspended in 3% (v/v) FBS in PBS at a cell concentration of $1 \times 10^7$ per milliliter. In accordance to the manufacture's specifications, antibody to the cell surface marker of interest (see below) was added to one hundred microliters of cell suspension and the mixture was incubated in the dark for 30 minutes at 4° C. After incubation, cells were washed with PBS and centrifuged to remove unbound antibody. Cells were resuspended in 500 microliter PBS and analyzed by flow cytometry. Flow cytometty analysis was performed with a FACScalibur instrument (Becton Dickinson, San Jose, Calif.).

The following antibodies to cell surface markers were used.

| Antibody | Manufacture | Catalog Number |
|---|---|---|
| CD10 | BD Pharmingen (San Diego, CA) | 555375 |
| CD13 | BD Pharmingen | 555394 |
| CD31 | BD Pharmingen | 555446 |
| CD34 | BD Pharmingen | 555821 |
| CD44 | BD Pharmingen | 555478 |
| CD45RA | BD Pharmingen | 555489 |
| CD73 | BD Pharmingen | 550257 |
| CD90 | BD Pharmingen | 555596 |
| CD117 | BD Pharmingen | 340529 |
| CD141 | BD Pharmingen | 559781 |
| PDGFr-alpha | BD Pharmingen | 556002 |
| HLA-A, B, C | BD Pharmingen | 555553 |
| HLA-DR, DP, DQ | BD Pharmingen | 555558 |
| IgG-FITC | Sigma (St. Louis, MO) | F-6522 |
| IgG-PE | Sigma | P-4685 |

Cells were analyzed at passages 8, 15, and 20, and umbilical cord tissue-derived cells from different donors were compared to each other. In addition, cells cultured on gelatin-coated flasks were compared to cells cultured on uncoated flasks.

Umbilical cord tissue-derived cells showed positive expression of CD10, CD13, CD44, CD73, CD 90, PDGFr-alpha and HLA-A, B, C, indicated by the increased values of fluorescence relative to the IgG control. These cells were negative for detectable expression of CD31, CD34, CD45, CD117, CD141, and HLA-DR, DP, DQ, indicated by fluorescence values comparable to the IgG control. Variations in fluorescence values of positive curves were accounted for. The mean (i.e., CD13) and range (i.e., CD90) of the positive curves showed some variation, but the curves appeared normal, confirming a homogenous population. Both curves individually exhibited values greater than the IgG control.

Cells at passage 8, 15, and 20 all expressed CD10, CD13, CD44, CD73, CD 90, PDGFr-alpha and HLA-A, B, C, indicated by increased fluorescence relative to the IgG control. These cells were negative for CD31, CD34, CD45, CD117, CD141, and HLA-DR, DP, DQ, indicated by fluorescence values consistent with the IgG control.

Isolates from separate donors each showed positive expression of CD10, CD13, CD44, CD73, CD 90, PDGFr-alpha and HLA-A, B, C, reflected in the increased values of fluorescence relative to the IgG control. These cells were negative for expression of CD31, CD34, CD45, CD117, CD141, and HLA-DR, DP, DQ with fluorescence values consistent with the IgG control.

Cells expanded on gelatin and uncoated flasks all were positive for expression of CD10, CD13, CD44, CD73, CD 90, PDGFr-alpha and HLA-A, B, C, with increased values of fluorescence relative to the IgG control. These cells were negative for expression of CD31, CD34, CD45, CD117, CD141, and HLA-DR, DP, DQ, with fluorescence values consistent with the IgG control.

Thus, umbilical cord tissue-derived cells are positive for CD10, CD13, CD44, CD73, CD90, PDGFr-alpha, HLA-A, B,C and negative for CD31, CD34, CD45, CD117, CD141 and HLA-DR, DP, DQ. This identity was consistent between variations in variables including the donor, passage, and culture vessel surface coating. Some variation in individual fluorescence value histogram curve means and ranges was observed, but all positive curves under all conditions tested were normal and expressed fluorescence values greater than the IgG control, thereby confirming that the cells comprise a homogenous population that has positive expression of the markers.

EXAMPLE 3

Immunohistochemical Characterization of Cell Phenotypes

Human umbilical cord tissue was harvested and immersion-fixed in 4% (w/v) paraformaldehyde overnight at 4° C. Immunohistochemistry was performed using antibodies directed against the following epitopes: vimentin (1:500; Sigma, St. Louis, Mo.), desmin (1:150, raised against rabbit; Sigma; or 1:300, raised against mouse; Chemicon, Temecula, Calif.), alpha-smooth muscle actin (SMA; 1:400; Sigma), cytokeratin 18 (CK18; 1:400; Sigma), von Willebrand Factor (vWF; 1:200; Sigma), and CD34 (human CD34 Class III; 1:100; DAKOCytomation, Carpinteria, Calif.). In addition, the following markers were tested: anti-human GROalpha-PE (1:100; Becton Dickinson, Franklin Lakes, N.J.), anti-human GCP-2 (1:100; Santa Cruz Biotech, Santa Cruz, Calif.), anti-human oxidized LDL receptor 1 (ox-LDL R1; 1:100; Santa Cruz Biotech), and anti-human NOGO-A (1:100; Santa Cruz Biotech). Fixed specimens were trimmed with a scalpel and placed within OCT embedding compound (Tissue-Tek OCT; Sakura, Torrance, Calif.) on a dry ice bath containing ethanol. Frozen blocks were then sectioned (10 μm thick) using a standard cryostat (Leica Microsystems) and mounted onto glass slides for staining.

Immunohistochemistry was performed similar to previous studies (Messina et al. (2003) Exper. Neurol. 184:816-29). In brief, tissue sections were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma) for 1 hour to access intracellular antigens. In instances where the epitope of interest would be located on the cell surface (CD34, ox-LDL R1), Triton was omitted in all steps of the procedure in order to prevent epitope loss. Furthermore, in instances where the primary antibody was raised against goat (GCP-2, ox-LDL R1, NOGO-A), 3% (v/v) donkey serum was used in place of goat serum throughout the procedure. Primary antibodies, diluted in blocking solution, were then applied to the sections for a period of 4 hours at room temperature. Primary antibody solutions were removed, and cultures washed with PBS prior to application of secondary antibody solutions (1 hour at room temperature) containing block along with goat anti-mouse IgG-Texas Red (1:250; Molecular Probes, Eugene, Oreg.) and/or goat anti-rabbit IgG-Alexa 488 (1:250; Molecular Probes) or donkey anti-goat IgG-FITC (1:150; Santa Cruz Biotech). Cultures were washed, and 10 micromolar DAPI (Molecular Probes) was applied for 10 minutes to visualize cell nuclei.

Fluorescence was visualized using the appropriate fluorescence filter on an Olympus inverted epi-fluorescent microscope (Olympus, Melville, N.Y.). Positive staining was represented by fluorescence signal above control staining. Representative images were captured using a digital color videocamera and ImagePro software (Media Cybernetics, Carlsbad, Calif.). For triple-stained samples, each image was taken using only one emission filter at a time.

Vimentin, desmin, SMA, CK18, vWF, and CD34 markers were expressed in a subset of the cells found within umbilical cord. In particular, vWF and CD34 expression were restricted to blood vessels contained within the cord. CD34+ cells were on the innermost layer (lumen side). Vimentin expression was found throughout the matrix and blood vessels of the cord. SMA was limited to the matrix and outer walls of the artery & vein, but not contained with the vessels themselves. CK18 and desmin were observed within the vessels only, desmin being restricted to the middle and outer layers. The expression of GROalpha, GCP-2, ox-LDL R1, and NOGO-A were not observed within umbilical cord tissue.

EXAMPLE 4

Oligonucleotide Array Analysis

Affymetrix GeneChip® arrays were used to compare gene expression profiles of umbilical cord tissue-derived cells with fibroblasts, human mesenchymal stem cells, and another cell line derived from human bone marrow. This analysis provided a characterization of the postpartum-derived cells and identified unique molecular markers for these cells.

Human umbilical cords were obtained from National Disease Research Interchange (NDRI, Philadelphia, Pa.) from normal full term deliveries with patient consent. The tissues were received and cells were isolated as described above. Cells were cultured in Growth Medium (using DMEM-LG) on gelatin-coated tissue culture plastic flasks. The cultures were incubated at 37° C. with 5% $CO_2$.

Human dermal fibroblasts were purchased from Cambrex Incorporated (Walkersville, Md.; Lot number 9F0844) and ATCC CRL-1501 (CCD39SK). Both lines were cultured in DMEM/F12 medium (Invitrogen, Carlsbad, Calif.) with 10% (v/v) fetal bovine serum (Hyclone) and penicillin/streptomycin (Invitrogen). The cells were grown on standard tissue-treated plastic.

Human mesenchymal stem cells (hMSC) were purchased from Cambrex Incorporated (Walkersville, Md.; Lot numbers 2F1655, 2F1656 and 2F1657) and cultured according to the manufacturer's specifications in MSCGM Media (Cambrex). The cells were grown on standard tissue cultured plastic at 37° C. with 5% $CO_2$.

Human iliac crest bone marrow was received from NDRI with patient consent. The marrow was processed according to the method outlined by Ho, et al. (WO03/025149). The marrow was mixed with lysis buffer (155 mM $NH_4Cl$, 10 mM $KHCO_3$, and 0.1 mM EDTA, pH 7.2) at a ratio of 1 part bone marrow to 20 parts lysis buffer. The cell suspension was vortexed, incubated for 2 minutes at ambient temperature, and centrifuged for 10 minutes at 500×g. The supernatant was discarded and the cell pellet was resuspended in Minimal Essential Medium-alpha (Invitrogen) supplemented with 10% (v/v) fetal bovine serum and 4 mM glutamine. The cells were centrifuged again and the cell pellet was resuspended in fresh medium. The viable mononuclear cells were counted using trypan-blue exclusion (Sigma, St. Louis, Mo.). The mononuclear cells were seeded in tissue-cultured plastic flasks at 5×104 cells/$cm^2$. The cells were incubated at 37° C. with 5% $CO_2$ at either standard atmospheric $O_2$ or at 5% $O_2$. Cells were cultured for 5 days without a media change. Media and non-adherent cells were removed after 5 days of culture. The adherent cells were maintained in culture.

Actively growing cultures of cells were removed from the flasks with a cell scraper in cold PBS. The cells were centrifuged for 5 minutes at 300×g. The supernatant was removed and the cells were resuspended in fresh PBS and centrifuged again. The supernatant was removed and the cell pellet was immediately frozen and stored at −80° C. Cellular mRNA was extracted and transcribed into cDNA, which was then transcribed into cRNA and biotin-labeled. The biotin-labeled cRNA was hybridized with HG-U133A GeneChip oligonucleotide array (Affymetrix, Santa Clara Calif.). The hybridization and data collection was performed according to the manufacturer's specifications. Analyses were performed using "Significance Analysis of Microarrays" (SAM) version 1.21 computer software (Stanford University; Tusher et al. (2001) Proc. Natl. Acad. Sci. USA 98:5116-21).

Fourteen different populations of cells were analyzed. The cells along with passage information, culture substrate, and culture media are listed in Table 1.

TABLE 1

Cells analyzed by the microarray study. Cell lines are listed by identification code along with passage at time of analysis, cell growth substrate and growth medium

| Cell Population | Passage | Substrate | Medium |
| --- | --- | --- | --- |
| Umbilical cord (022803) | 2 | Gelatin | DMEM, 15% FBS, 2-ME |
| Umbilical cord (042103) | 3 | Gelatin | DMEM, 15% FBS, 2-ME |
| Umbilical cord (071003) | 4 | Gelatin | DMEM, 15% FBS, 2-ME |
| ICBM (070203) (5% O2) | 3 | Plastic | MEM, 10% FBS |
| ICBM (062703) (std. O2) | 5 | Plastic | MEM, 10% FBS |
| ICBM (062703) (5% O2) | 5 | Plastic | MEM, 10% FBS |
| hMSC (Lot 2F1655) | 3 | Plastic | MSCGM |
| hMSC (Lot 2F1656) | 3 | Plastic | MSCGM |
| hMSC (Lot 2F 1657) | 3 | Plastic | MSCGM |
| hFibroblast (9F0844) | 9 | Plastic | DMEM-F12, 10% FBS |
| hFibroblast (CCD39SK) | 4 | Plastic | DMEM-F12, 10% FBS |

The data were evaluated by a Principle Component Analysis, analyzing the 290 genes that were differentially expressed in the cells. This analysis allows for a relative comparison for the similarities between the populations. Table 2 shows the Euclidean distances that were calculated for the comparison of the cell pairs. The Euclidean distances were based on the comparison of the cells based on the 290 genes that were differentially expressed among the cell types. The Euclidean distance is inversely proportional to similarity between the expression of the 290 genes (i.e., the greater the distance, the less similarity exists).

TABLE 2

The Euclidean Distances for the Cell Pairs

| Cell Pair | Euclidean Distance |
| --- | --- |
| ICBM-hMSC | 24.71 |
| Placenta-umbilical | 25.52 |
| ICBM-Fibroblast | 36.44 |
| ICBM-placenta | 37.09 |
| Fibroblast-MSC | 39.63 |
| ICBM-Umbilical | 40.15 |
| Fibroblast-Umbilical | 41.59 |
| MSC-Placenta | 42.84 |
| MSC-Umbilical | 46.86 |
| ICBM-placenta | 48.41 |

Tables 3 and 4 below show the expression of genes increased in umbilical cord tissue-derived cells (Table 3), and reduced in umbilical cord tissue-derived cells (Table 4). The column entitled "Probe Set ID" refers to the manufacturer's identification code for the sets of several oligonucleotide probes located on a particular site on the chip, which hybridize to the named gene (column "Gene Name"), comprising a sequence that can be found within the NCBI (GenBank) database at the specified accession number (column "NCBI Accession Number").

TABLE 3

Genes shown to have specifically increased expression in the umbilical cord tissue-derived cells as compared to other cell lines assayed
Genes Increased in Umbilical cord tissue-Derived Cells

| Probe Set ID | Gene Name | NCBI Accession Number |
|---|---|---|
| 202859_x_at | interleukin 8 | NM_000584 |
| 211506_s_at | interleukin 8 | AF043337 |
| 210222_s_at | reticulon 1 | BC000314 |
| 204470_at | chemokine (C—X—C motif) ligand 1 (melanoma growth stimulating activity | NM_001511 |
| 206336_at | chemokine (C—X—C motif) ligand 6 (granulocyte chemotactic protein 2) | NM_002993 |
| 207850_at | chemokine (C—X—C motif) ligand 3 | NM_002090 |
| 203485_at | reticulon 1 | NM_021136 |
| 202644_s_at | tumor necrosis factor, alpha-induced protein 3 | NM_006290 |

TABLE 4

Genes shown to have decreased expression in umbilical cord tissue-derived cells as compared to other cell lines assayed
Genes Decreased in Umbilical cord tissue- and Placenta-Derived Cells

| Probe Set ID | Gene name | NCBI Accession Number |
|---|---|---|
| 210135_s_at | short stature homeobox 2 | AF022654.1 |
| 205824_at | heat shock 27 kDa protein 2 | NM_001541.1 |
| 209687_at | chemokine (C—X—C motif) ligand 12 (stromal cell-derived factor 1) | U19495.1 |
| 203666_at | chemokine (C—X—C motif) ligand 12 (stromal cell-derived factor 1) | NM_000609.1 |
| 212670_at | elastin (supravalvular aortic stenosis, Williams-Beuren syndrome) | AA479278 |
| 213381_at | Homo sapiens mRNA; cDNA DKFZp586M2022 (from clone DKFZp586M2022) | N91149 |
| 206201_s_at | mesenchyme homeo box 2 (growth arrest-specific homeo box) | NM_005924.1 |
| 205817_at | sine oculis homeobox homolog 1 (Drosophila) | NM_005982.1 |
| 209283_at | crystallin, alpha B | AF007162.1 |
| 212793_at | dishevelled associated activator of morphogenesis 2 | BF513244 |
| 213488_at | DKFZP586B2420 protein | AL050143.1 |
| 209763_at | similar to neuralin 1 | AL049176 |
| 205200_at | tetranectin (plasminogen binding protein) | NM_003278.1 |
| 205743_at | src homology three (SH3) and cysteine rich domain | NM_003149.1 |
| 200921_s_at | B-cell translocation gene 1, anti-proliferative | NM_001731.1 |
| 206932_at | cholesterol 25-hydroxylase | NM_003956.1 |
| 204198_s_at | runt-related transcription factor 3 | AA541630 |
| 219747_at | hypothetical protein FLJ23191 | NM_024574.1 |
| 204773_at | interleukin 11 receptor, alpha | NM_004512.1 |
| 202465_at | procollagen C-endopeptidase enhancer | NM_002593.2 |
| 203706_s_at | frizzled homolog 7 (Drosophila) | NM_003507.1 |
| 212736_at | hypothetical gene BC008967 | BE299456 |
| 214587_at | collagen, type VIII, alpha 1 | BE877796 |
| 201645_at | tenascin C (hexabrachion) | NM_002160.1 |
| 210239_at | iroquois homeobox protein 5 | U90304.1 |
| 203903_s_at | hephaestin | NM_014799.1 |
| 205816_at | integrin, beta 8 | NM_002214.1 |
| 203069_at | synaptic vesicle glycoprotein 2 | NM_014849.1 |
| 213909_at | Homo sapiens cDNA FLJ12280 fis, clone MAMMA1001744 | AU147799 |
| 206315_at | cytokine receptor-like factor 1 | NM_004750.1 |
| 204401_at | potassium intermediate/small conductance calcium-activated channel, subfamily N, member 4 | NM_002250.1 |
| 216331_at | integrin, alpha 7 | AK022548.1 |
| 209663_s_at | integrin, alpha 7 | AF072132.1 |
| 213125_at | DKFZP586L151 protein | AW007573 |
| 202133_at | transcriptional co-activator with PDZ-binding motif (TAZ) | AA081084 |
| 206511_s_at | sine oculis homeobox homolog 2 (Drosophila) | NM_016932.1 |
| 213435_at | KIAA1034 protein | AB028957.1 |
| 206115_at | early growth response 3 | NM_004430.1 |
| 213707_s_at | distal-less homeo box 5 | NM_005221.3 |
| 218181_s_at | hypothetical protein FLJ20373 | NM_017792.1 |
| 209160_at | aldo-keto reductase family 1, member C3 (3-alpha hydroxysteroid dehydrogenase, type II) | AB018580.1 |
| 213905_x_at | biglycan | AA845258 |
| 201261_x_at | biglycan | BC002416.1 |
| 202132_at | transcriptional co-activator with PDZ-binding motif (TAZ) | AA081084 |
| 214701_s_at | fibronectin 1 | AJ276395.1 |
| 213791_at | proenkephalin | NM_006211.1 |

TABLE 4-continued

Genes shown to have decreased expression in umbilical cord tissue-derived
cells as compared to other cell lines assayed
Genes Decreased in Umbilical cord tissue- and Placenta-Derived Cells

| Probe Set ID | Gene name | NCBI Accession Number |
|---|---|---|
| 205422_s_at | integrin, beta-like 1 (with EGF-like repeat domains) | NM_004791.1 |
| 214927_at | Homo sapiens mRNA full length insert cDNA clone EUROIMAGE 1968422 | AL359052.1 |
| 206070_s_at | EphA3 | AF213459.1 |
| 212805_at | KIAA0367 protein | AB002365.1 |
| 219789_at | natriuretic peptide receptor C/guanylate cyclase C (atrionatriuretic peptide receptor C) | AI628360 |
| 219054_at | hypothetical protein FLJ14054 | NM_024563.1 |
| 213429_at | Homo sapiens mRNA; cDNA DKFZp564B222 (from clone DKFZp564B222) | AW025579 |
| 204929_s_at | vesicle-associated membrane protein 5 (myobrevin) | NM_006634.1 |
| 201843_s_at | EGF-containing fibulin-like extracellular matrix protein 1 | NM_004105.2 |
| 221478_at | BCL2/adenovirus E1B 19 kDa interacting protein 3-like | AL132665.1 |
| 201792_at | AE binding protein 1 | NM_001129.2 |
| 204570_at | cytochrome c oxidase subunit VIIa polypeptide 1 (muscle) | NM_001864.1 |
| 201621_at | neuroblastoma, suppression of tumorigenicity 1 | NM_005380.1 |
| 202718_at | insulin-like growth factor binding protein 2, 36 kDa | NM_000597.1 |

Tables 5, 6, and 7 show the expression of genes increased in human fibroblasts (Table 5), ICBM cells (Table 6), and MSCs (Table 7).

TABLE 5

Genes that were shown to have increased expression in
fibroblasts as compared to the other cell lines assayed
Genes increased in fibroblasts dual specificity phosphatase 2
KIAA0527 protein
Homo sapiens cDNA: FLJ23224 fis, clone ADSU02206
dynein, cytoplasmic, intermediate polypeptide 1
ankyrin 3, node of Ranvier (ankyrin G)
inhibin, beta A (activin A, activin AB alpha polypeptide)
ectonucleotide pyrophosphatase/phosphodiesterase 4 (putative function)
KIAA1053 protein
microtubule-associated protein 1A
zinc finger protein 41
HSPC019 protein
Homo sapiens cDNA: FLJ23564 fis, clone LNG10773
Homo sapiens mRNA; cDNA DKFZp564A072 (from clone DKFZp564A072)
LIM protein (similar to rat protein kinase C-binding enigma)
inhibitor of kappa light polypeptide gene enhancer in B-cells, kinase complex-associated protein
hypothetical protein FLJ22004
Human (clone CTG-A4) mRNA sequence
ESTs, Moderately similar to cytokine receptor-like factor 2; cytokine receptor CRL2 precursor [Homo sapiens]
transforming growth factor, beta 2
hypothetical protein MGC29643
antigen identified by monoclonal antibody MRC OX-2
putative X-linked retinopathy protein

TABLE 6

Genes that were shown to have increased expression
in the ICBM-derived cells as compared to the other cell lines assayed.
Genes Increased In ICBM Cells cardiac ankyrin repeat protein
MHC class I region ORF
integrin, alpha 10
hypothetical protein FLJ22362
UDP-N-acetyl-alpha-D-galactosamine:polypeptide N-acetylgalactosaminyltransferase 3 (GalNAc-T3)
interferon-induced protein 44

TABLE 6-continued

Genes that were shown to have increased expression
in the ICBM-derived cells as compared to the other cell lines assayed.
Genes Increased In ICBM Cells SRY (sex determining region Y)-box 9 (campomelic dysplasia, autosomal sex-reversal)
keratin associated protein 1-1
hippocalcin-like 1
jagged 1 (Alagille syndrome)
proteoglycan 1, secretory granule

TABLE 7

Genes that were shown to have increased expression in the
MSC cells as compared to the other cell lines assayed.
Genes Increased In MSC Cells interleukin 26
maltase-glucoamylase (alpha-glucosidase)
nuclear receptor subfamily 4, group A, member 2
v-fos FBJ murine osteosarcoma viral oncogene homolog
hypothetical protein DC42
nuclear receptor subfamily 4, group A, member 2
FBJ murine osteosarcoma viral oncogene homolog B
WNT1 inducible signaling pathway protein 1
MCF.2 cell line derived transforming sequence
potassium channel, subfamily K, member 15
cartilage paired-class homeoprotein 1
Homo sapiens cDNA FLJ12232 fis, clone MAMMA1001206
Homo sapiens cDNA FLJ34668 fis, clone LIVER2000775
jun B proto-oncogene
B-cell CLL/lymphoma 6 (zinc finger protein 51)
zinc finger protein 36, C3H type, homolog (mouse)

The foregoing analysis included cells derived from three different umbilical cords and two different lines of dermal fibroblasts, three lines of mesenchymal stem cells, and three lines of iliac crest bone marrow cells. The mRNA that was expressed by these cells was analyzed using an oligonucleotide array that contained probes for 22,000 genes. Results showed that 290 genes are differentially expressed in these five different cell types. These genes include seven genes specifically increased in the umbilical cord tissue-derived cells. Fifty-four genes were found to have specifically lower expression levels in umbilical cord tissue-derived cells, as compared with the other cell types. The expression of selected genes has been confirmed by PCR. These results demonstrate that umbilical cord tissue-derived cells have a distinct gene expression profile, for example, as compared to bone marrow-derived cells and fibroblasts.

EXAMPLE 5

Cell Markers in Umbilical Cord Tissue-Derived Cells

As demonstrated above, six "signature" genes were identified for umbilical cord tissue-derived cells: oxidized LDL receptor 1, interleukin-8, rennin, reticulon, chemokine receptor ligand 3 (CXC ligand 3), and granulocyte chemotactic protein 2 (GCP-2). These "signature" genes were expressed at relatively high levels in postpartum-derived cells.

The procedures described in this example were conducted to verify the microarray data and find concordance/discordance between gene and protein expression, as well as to establish a series of reliable assay for detection of unique identifiers for umbilical cord tissue-derived cells.

Umbilical cord tissue-derived cells (four isolates), and Normal Human Dermal Fibroblasts (NHDF; neonatal and adult) were grown in Growth Medium with penicillin/streptomycin in a gelatin-coated T75 flask. Mesechymal Stem Cells (MSCs) were grown in Mesenchymal Stem Cell Growth Medium Bullet kit (MSCGM; Cambrex, Walkerville, Md.).

For the IL-8 protocol, cells were thawed from liquid nitrogen and plated in gelatin-coated flasks at 5,000 cells/cm$^2$, grown for 48 hours in Growth Medium and then grown for further 8 hours in 10 milliliters of serum starvation medium [DMEM—low glucose (Gibco, Carlsbad, Calif.), penicillin/streptomycin (Gibco, Carlsbad, Calif.) and 0.1% (w/v) Bovine Serum Albumin (BSA; Sigma, St. Louis, Mo.)]. After this treatment RNA was extracted and the supernatants were centrifuged at 150×g for 5 minutes to remove cellular debris. Supernatants were then frozen at −80° C. for ELISA analysis.

Postpartum cells derived from the umbilical cord, as well as human fibroblasts derived from human neonatal foreskin were cultured in Growth Medium in gelatin-coated T75 flasks. Cells were frozen at passage 11 in liquid nitrogen. Cells were thawed and transferred to 15-milliliter centrifuge tubes. After centrifugation at 150×g for 5 minutes, the supernatant was discarded. Cells were resuspended in 4 milliliters culture medium and counted. Cells were grown in a 75 cm$^2$ flask containing 15 milliliters of Growth Medium at 375,000 cell/flask for 24 hours. The medium was changed to a serum starvation medium for 8 hours. Serum starvation medium was collected at the end of incubation, centrifuged at 14,000×g for 5 minutes (and stored at −20° C.).

To estimate the number of cells in each flask, 2 milliliters of trypsin/EDTA (Gibco, Carlsbad, Calif.) was added each flask. After cells detached from the flask, trypsin activity was neutralized with 8 milliliters of Growth Medium. Cells were transferred to a 15 milliliters centrifuge tube and centrifuged at 150×g for 5 minutes. Supernatant was removed and 1 milliliter Growth Medium was added to each tube to resuspend the cells. Cell number was estimated using a hemocytometer.

The amount of IL-8 secreted by the cells into serum starvation medium was analyzed using ELISA assays (R&D Systems, Minneapolis, Minn.). All assays were tested according to the instructions provided by the manufacturer.

RNA was extracted from confluent umbilical cord tissue-derived cells and fibroblasts or for IL-8 expression from cells treated as described above. Cells were lysed with 350 microliters buffer RLT containing beta-mercaptoethanol (Sigma, St. Louis, Mo.) according to the manufacturer's instructions (RNeasy Mini Kit; Qiagen, Valencia, Calif.). RNA was extracted according to the manufacturer's instructions (RNeasy Mini Kit; Qiagen, Valencia, Calif.) and subjected to DNase treatment (2.7 U/sample) (Sigma St. Louis, Mo.). RNA was eluted with 50 microliters DEPC-treated water and stored at −80° C.

RNA was also extracted from human umbilical cord tissue. Tissue (30 milligram) was suspended in 700 microliters of buffer RLT containing 2-mercaptoethanol. Samples were mechanically homogenized and the RNA extraction proceeded according to manufacturer's specification. RNA was extracted with 50 microliters of DEPC-treated water and stored at −80° C. RNA was reversed transcribed using random hexamers with the TaqMan reverse transcription reagents (Applied Biosystems, Foster City, Calif.) at 25° C. for 10 minutes, 37° C. for 60 minutes, and 95° C. for 10 minutes. Samples were stored at −20° C.

Genes identified by cDNA microarray as uniquely regulated in postpartum cells (signature genes—including oxidized LDL receptor, interleukin-8, rennin and reticulon), were further investigated using real-time and conventional PCR.

PCR was performed on cDNA samples using Assays-on-Demand™ gene expression products: oxidized LDL receptor (Hs00234028); rennin (Hs00166915); reticulon (Hs00382515); CXC ligand 3 (Hs00171061); GCP-2 (Hs00605742); IL-8 (Hs00174103); and GAPDH (Applied Biosystems, Foster City, Calif.) were mixed with cDNA and TaqMan Universal PCR master mix according to the manufacturer's instructions (Applied Biosystems, Foster City, Calif.) using a 7000 sequence detection system with ABI Prism 7000 SDS software (Applied Biosystems, Foster City, Calif.). Thermal cycle conditions were initially 50° C. for 2 min and 95° C. for 10 min, followed by 40 cycles of 95° C. for 15 sec and 60° C. for 1 min. PCR data was analyzed according to manufacturer's specifications (User Bulletin #2 from Applied Biosystems for ABI Prism 7700 Sequence Detection System).

Conventional PCR was performed using an ABI PRISM 7700 (Perkin Elmer Applied Biosystems, Boston, Mass., USA) to confirm the results from real-time PCR. PCR was performed using 2 microliters of cDNA solution, 1×AmpliTaq Gold universal mix PCR reaction buffer (Applied Biosystems, Foster City, Calif.) and initial denaturation at 94° C. for 5 minutes. Amplification was optimized for each primer set. For IL-8, CXC ligand 3, and reticulon (94° C. for 15 seconds, 55° C. for 15 seconds and 72° C. for 30 seconds for 30 cycles); for rennin (94° C. for 15 seconds, 53° C. for 15 seconds and 72° C. for 30 seconds for 38 cycles); for oxidized LDL receptor and GAPDH (94° C. for 15 seconds, 55° C. for 15 seconds and 72° C. for 30 seconds for 33 cycles). Primers used for amplification are listed in Table 8. Primer concentration in the final PCR reaction was 1 micromolar except for GAPDH, which was 0.5 micromolar. GAPDH primers were the same as real-time PCR, except that the manufacturer's TaqMan probe was not added to the final PCR reaction. Samples were run on 2% (w/v) agarose gel and stained with ethidium bromide (Sigma, St. Louis, Mo.). Images were captured using a 667 Universal Twinpack film (VWR International, South Plainfield, N.J.) using a focal-length Polaroid camera (VWR International, South Plainfield, N.J.).

TABLE 8

Primers Used

| Primer name | | Primers | |
|---|---|---|---|
| Oxidized LDL receptor | S: | 5'-GAGAAATCCAAAGAGCAAATGG-3' | (SEQ ID NO: 1) |
| Renin | A: | 5'-AGAATGGAAAACTGGAATAGG-3' | (SEQ ID NO: 2) |
| | S: | 5'-TCTTCGATGCTTCGGATTCC-3' | (SEQ ID NO: 3) |
| | A: | 5'-GAATTCTCGGAATCTCTGTTG-3' | (SEQ ID NO: 4) |
| Reticulon | S: | 5'-TTACAAGCAGTGCAGAAAACC-3' | (SEQ ID NO: 5) |
| | A: | 5'-AGTAAACATTGAAACCACAGCC-3' | (SEQ ID NO: 6) |
| Interleukin-8 | S: | 5'-TCTGCAGCTCTGTGTGAAGG-3' | (SEQ ID NO: 7) |
| | A: | 5'-CTTCAAAAACTTCTCCACAACC-3' | (SEQ ID NO: 8) |
| Chemokine (CXC) ligand 3 | S: | 5'-CCCACGCCACGCTCTCC-3' | (SEQ ID NO: 9) |
| | A: | 5'-TCCTGTCAGTTGGTGCTCC-3' | (SEQ ID NO: 10) |

Cells were fixed with cold 4% (w/v) paraformaldehyde (Sigma-Aldrich, St. Louis, Mo.) for 10 minutes at room temperature. One isolate at passage 0 (P0) (directly after isolation) and two isolates at passage 11 (P11), and fibroblasts (P11) were used. Immunocytochemistry was performed using antibodies directed against the following epitopes: vimentin (1:500, Sigma, St. Louis, Mo.), desmin (1:150; Sigma—raised against rabbit; or 1:300; Chemicon, Temecula, Calif.—raised against mouse), alpha-smooth muscle actin (SMA; 1:400; Sigma), cytokeratin 18 (CK18; 1:400; Sigma), von Willebrand Factor (vWF; 1:200; Sigma), and CD34 (human CD34 Class III; 1:100; DAKOCytomation, Carpinteria, Calif.). In addition, the following markers were tested on passage 11 postpartum cells: anti-human GRO alpha-PE (1:100; Becton Dickinson, Franklin Lakes, N.J.), anti-human GCP-2 (1:100; Santa Cruz Biotech, Santa Cruz, Calif.), anti-human oxidized LDL receptor 1 (ox-LDL R1; 1:100; Santa Cruz Biotech), and anti-human NOGA-A (1:100; Santa Cruz, Biotech).

Cultures were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma, St. Louis, Mo.) for 30 minutes to access intracellular antigens. Where the epitope of interest was located on the cell surface (CD34, ox-LDL R1), Triton X-100 was omitted in all steps of the procedure in order to prevent epitope loss. Furthermore, in instances where the primary antibody was raised against goat (GCP-2, ox-LDL R1, NOGO-A), 3% (v/v) donkey serum was used in place of goat serum throughout. Primary antibodies, diluted in blocking solution, were then applied to the cultures for a period of 1 hour at room temperature. The primary antibody solutions were removed and the cultures were washed with PBS prior to application of secondary antibody solutions (1 hour at room temperature) containing block along with goat anti-mouse IgG-Texas Red (1:250; Molecular Probes, Eugene, Oreg.) and/or goat anti-rabbit IgG-Alexa 488 (1:250; Molecular Probes) or donkey anti-goat IgG-FITC (1:150, Santa Cruz Biotech). Cultures were then washed and 10 micromolar DAPI (Molecular Probes) applied for 10 minutes to visualize cell nuclei.

Following immunostaining, fluorescence was visualized using an appropriate fluorescence filter on an Olympus inverted epi-fluorescent microscope (Olympus, Melville, N.Y.). In all cases, positive staining represented fluorescence signal above control staining where the entire procedure outlined above was followed with the exception of application of a primary antibody solution. Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Adherent cells in flasks were washed in phosphate buffered saline (PBS) (Gibco, Carlsbad, Calif.) and detached with Trypsin/EDTA (Gibco, Carlsbad, Calif.). Cells were harvested, centrifuged, and re-suspended 3% (v/v) FBS in PBS at a cell concentration of $1\times10^7$ per milliliter. One hundred microliter aliquots were delivered to conical tubes. Cells stained for intracellular antigens were penneablized with Penn/Wash buffer (BD Pharmingen, San Diego, Calif.). Antibody was added to aliquots as per manufactures specifications and the cells were incubated for in the dark for 30 minutes at 4° C. After incubation, cells were washed with PBS and centrifuged to remove excess antibody. Cells requiring a secondary antibody were resuspended in 100 microliters of 3% FBS. Secondary antibody was added as per manufactures specification and the cells were incubated in the dark for 30 minutes at 4° C. After incubation, cells were washed with PBS and centrifuged to remove excess secondary antibody. Washed cells were resuspended in 0.5 milliliters PBS and analyzed by flow cytometry. The following antibodies were used: oxidized LDL receptor 1 (sc-5813; Santa Cruz, Biotech), GROa (555042; BD Pharmingen, Bedford, Mass.), Mouse IgG1 kappa, (P-4685 and M-5284; Sigma), Donkey against Goat IgG (sc-3743; Santa Cruz, Biotech.). Flow cytometry analysis was performed with FACScalibur (Becton Dickinson San Jose, Calif.).

The data obtained from real-time PCR were analyzed by the ΔΔCT method and expressed on a logarithmic scale. Levels of reticulon and oxidized LDL receptor expression were higher in umbilical cord tissue-derived cells as compared to other cells. No significant difference in the expression levels of CXC ligand 3 and GCP-2 were found between postpartum-derived cells and controls. The results of real-time PCR were confirmed by conventional PCR. Sequencing of PCR products further validated these observations. No significant difference in the expression level of CXC ligand 3 was found between postpartum-derived cells and controls using conventional PCR CXC ligand 3 primers listed above.

The production of the cytokine, IL-8 in postpartum was elevated in both Growth Medium-cultured and serum-starved postpartum-derived cells. All real-time PCR data was validated with conventional PCR and by sequencing PCR products.

When supernatants of cells grown in serum-free medium were examined for the presence of IL-8, the highest amounts were detected in media derived from umbilical cells and some isolates of placenta cells (Table 9). No IL-8 was detected in medium derived from human dermal fibroblasts.

TABLE 9

IL-8 protein amount measured by ELISA

| Cell type | IL-8 |
|---|---|
| hFibro | ND |
| Umb Isolate 1 | 2058.42 ± 144.67 |
| Umb Isolate 2 | 2368.86 ± 22.73 |

Values picograms/million cells, n = 2, sem;
ND = Not Detected

Cells derived from the human umbilical cord tissue at passage 0 were probed for the production of selected proteins by immunocytochemical analysis. Immediately after isolation (passage 0), cells were fixed with 4% paraformaldehyde and exposed to antibodies for six proteins: von Willebrand Factor, CD34, cytokeratin 18, desmin, alpha-smooth muscle actin, and vimentin. Umbilical cord tissue-derived cells were positive for alpha-smooth muscle actin and vimentin, with the staining pattern consistent through passage 11.

Concordance between gene expression levels measured by microarray and PCR (both real-time and conventional) has been established for four genes: oxidized LDL receptor 1, rennin, reticulon, and IL-8. The expression of these genes was differentially regulated at the mRNA level in PPDCs, with IL-8 also differentially regulated at the protein level. Cells derived from the human umbilical cord tissue at passage 0 were probed for the expression of alpha-smooth muscle actin and vimentin, and were positive for both. The staining pattern was preserved through passage 11.

EXAMPLE 6

In Vitro Immunological Evaluation of Postpartum-Derived Cells

Postpartum-derived cells (PPDCs) were evaluated in vitro for their immunological characteristics in an effort to predict the immunological response, if any, these cells would elicit upon in vivo transplantation. PPDCs were assayed by flow cytometry for the presence of HLA-DR, HLA-DP, HLA-DQ, CD80, CD86, and B7-H2. These proteins are expressed by antigen-presenting cells (APC) and are required for the direct stimulation of naïve CD4+ T cells (Abbas & Lichtman, CELLULAR AND MOLECULAR IMMUNOLOGY, 5th Ed. (2003) Saunders, Philadelphia, p. 171). The cell lines were also analyzed by flow cytometry for the expression of HLA-G (Abbas & Lichtman, 2003, supra), CD 178 (Coumans, et al., (1999) *Journal of Immunological Methods* 224, 185-196), and PD-L2 (Abbas & Lichtman, 2003, supra; Brown, et. al. (2003) *The Journal of Immunology* 170, 1257-1266). The expression of these proteins by cells residing in placental tissues is thought to mediate the immuno-privileged status of placental tissues in utero. To predict the extent to which placenta- and umbilical cord tissue-derived cell lines elicit an immune response in vivo, the cell lines were tested in a one-way mixed lymphocyte reaction (MLR).

Cells were cultured to confluence in Growth Medium containing penicillin/streptomycin in T75 flasks (Corning, Corning, N.Y.) coated with 2% gelatin (Sigma, St. Louis, Mo.).

Cells were washed in phosphate buffered saline (PBS) (Gibco, Carlsbad, Calif.) and detached with Trypsin/EDTA (Gibco, Carlsbad, Mo.). Cells were harvested, centrifuged, and re-suspended in 3% (v/v) FBS in PBS at a cell concentration of $1 \times 10^7$ per milliliter. Antibody (Table 10) was added to one hundred microliters of cell suspension as per manufacturer's specifications and incubated in the dark for 30 minutes at 4° C. After incubation, cells were washed with PBS and centrifuged to remove unbound antibody. Cells were re-suspended in five hundred microliters of PBS and analyzed by flow cytometry using a FACSCalibur instrument (Becton Dickinson, San Jose, Calif.).

TABLE 10

Antibodies

| Antibody | Manufacturer | Catalog Number |
|---|---|---|
| HLA-DRDPDQ | BD Pharmingen (San Diego, CA) | 555558 |
| CD80 | BD Pharmingen (San Diego, CA) | 557227 |
| CD86 | BD Pharmingen (San Diego, CA) | 555665 |
| B7-H2 | BD Pharmingen (San Diego, CA) | 552502 |
| HLA-G | Abcam (Cambridgeshire, UK) | ab 7904-100 |
| CD 178 | Santa Cruz (San Cruz, CA) | sc-19681 |
| PD-L2 | BD Pharmingen (San Diego, CA) | 557846 |
| Mouse IgG2a | Sigma (St. Louis, MO) | F-6522 |
| Mouse IgG1kappa | Sigma (St. Louis, MO) | P-4685 |

Cryopreserved vials of passage 10 umbilical cord tissue-derived cells labeled as cell line A were sent on dry ice to CTBR (Senneville, Quebec) to conduct a mixed lymphocyte reaction using CTBR SOP No. CAC-031. Peripheral blood mononuclear cells (PBMCs) were collected from multiple male and female volunteer donors. Stimulator (donor) allogeneic PBMC, autologous PBMC, and postpartum cell lines were treated with mitomycin C. Autologous and mitomycin C-treated stimulator cells were added to responder (recipient) PBMCs and cultured for 4 days. After incubation, [$^3$H]thymidine was added to each sample and cultured for 18 hours. Following harvest of the cells, radiolabeled DNA was extracted, and [$^3$H]-thymidine incorporation was measured using a scintillation counter.

The stimulation index for the allogeneic donor (SIAD) was calculated as the mean proliferation of the receiver plus mitomycin C-treated allogeneic donor divided by the baseline proliferation of the receiver. The stimulation index of the PPDCs was calculated as the mean proliferation of the receiver plus mitomycin C-treated postpartum cell line divided by the baseline proliferation of the receiver.

Six human volunteer blood donors were screened to identify a single allogeneic donor that will exhibit a robust proliferation response in a mixed lymphocyte reaction with the other five blood donors. This donor was selected as the allogeneic positive control donor. The remaining five blood donors were selected as recipients. The allogeneic positive control donor and placenta cell lines were mitomycin C-treated and cultured in a mixed lymphocyte reaction with the five individual allogeneic receivers. Reactions were performed in triplicate using two cell culture plates with three receivers per plate (Table 11). The average stimulation index ranged from 6.5 (plate 1) to 9 (plate 2) and the allogeneic donor positive controls ranged from 42.75 (plate 1) to 70 (plate 2) (Table 12).

TABLE 11

Mixed Lymphocyte Reaction Data-Cell Line A (Umbilical cord)
DPM for Proliferation Assay

| Analytical number | Culture System | Replicates 1 | 2 | 3 | Mean | SD | CV |
|---|---|---|---|---|---|---|---|
| Plate ID: Plate 1 | | | | | | | |
| IM04-2478 | Proliferation baseline of receiver | 1074 | 406 | 391 | 623.7 | 390.07 | 62.5 |
| | Control of autostimulation (Mitomycin C treated autologous cells) | 672 | 510 | 1402 | 861.3 | 475.19 | 55.2 |
| | MLR allogenic donor IM04-2477 (Mitomycin C treated) | 43777 | 48391 | 38231 | 43466.3 | 5087.12 | 11.7 |
| | MLR with cell line (Mitomycin C treated cell type A) | 2914 | 5622 | 6109 | 4881.7 | 1721.36 | 35.3 |
| SI (donor) | | | | | 70 | | |
| SI (cell line) | | | | | 8 | | |
| IM04-2479 | Proliferation baseline of receiver | 530 | 508 | 527 | 521.7 | 11.93 | 2.3 |
| | Control of autostimulation (Mitomycin C treated autologous cells) | 701 | 567 | 1111 | 793.0 | 283.43 | 35.7 |
| | MLR allogenic donor IM04-2477 (Mitomycin C treated) | 25593 | 24732 | 22707 | 24344.0 | 1481.61 | 6.1 |
| | MLR with cell line (Mitomycin C treated cell type A) | 5086 | 3932 | 1497 | 3505.0 | 1832.21 | 52.3 |
| SI (donor) | | | | | 47 | | |
| SI (cell line) | | | | | 7 | | |
| IM04-2480 | Proliferation baseline of receiver | 1192 | 854 | 1330 | 1125.3 | 244.90 | 21.8 |
| | Control of autostimulation (Mitomycin C treated autologous cells) | 2963 | 993 | 2197 | 2051.0 | 993.08 | 48.4 |
| | MLR allogenic donor IM04-2477 (Mitomycin C treated) | 25416 | 29721 | 23757 | 26298.0 | 3078.27 | 11.7 |
| | MLR with cell line (Mitomycin C treated cell type A) | 2596 | 5076 | 3426 | 3699.3 | 1262.39 | 34.1 |
| SI (donor) | | | | | 23 | | |
| SI (cell line) | | | | | 3 | | |
| IM04-2481 | Proliferation baseline of receiver | 695 | 451 | 555 | 567.0 | 122.44 | 21.6 |
| | Control of autostimulation (Mitomycin C treated autologous cells) | 738 | 1252 | 464 | 818.0 | 400.04 | 48.9 |
| | MLR allogenic donor IM04-2477 (Mitomycin C treated) | 13177 | 24885 | 15444 | 17835.3 | 6209.52 | 34.8 |
| | MLR with cell line (Mitomycin C treated cell type A) | 4495 | 3671 | 4674 | 4280.0 | 534.95 | 12.5 |
| SI (donor) | | | | | 31 | | |
| SI (cell line) | | | | | 8 | | |
| Plate ID: Plate 2 | | | | | | | |
| IM04-2482 | Proliferation baseline of receiver | 432 | 533 | 274 | 413.0 | 130.54 | 31.6 |
| | Control of autostimulation (Mitomycin C treated autologous cells) | 1459 | 633 | 598 | 896.7 | 487.31 | 54.3 |
| | MLR allogenic donor IM04-2477 (Mitomycin C treated) | 24286 | 30823 | 31346 | 28818.3 | 3933.82 | 13.7 |
| | MLR with cell line (Mitomycin C treated cell type A) | 2762 | 1502 | 6723 | 3662.3 | 2724.46 | 74.4 |
| SI (donor) | | | | | 70 | | |
| SI (cell line) | | | | | 9 | | |
| IM04-2477 (allogenic donor) | Proliferation baseline of receiver | 312 | 419 | 349 | 360.0 | 54.34 | 15.1 |
| | control of autostimulation (Mitomycin treated autologous cells) | 567 | 604 | 374 | 515.0 | 123.50 | 24.0 |
| Cell line type A | Proliferation baseline of receiver | 5101 | 3735 | 2973 | 3936.3 | 1078.19 | 27.4 |
| | Control of autostimulation (Mitomycin treated autologous cells) | 1924 | 4570 | 2153 | 2882.3 | 1466.04 | 50.9 |

TABLE 12

Average stimulation index of umbilical cord tissue-derived cells and an allogeneic donor in a mixed lymphocyte reaction with five individual allogeneic receivers.

Average Stimulation Index

| | Recipient | Umbilicus |
|---|---|---|
| Plate 1 (receivers 1-4) | 42.75 | 6.5 |
| Plate 2 (receivers 5) | 70 | 9 |

Histograms of umbilical cord tissue-derived cells analyzed by flow cytometry show negative expression of HLA-DR, DP, DQ, CD80, CD86, and B7-H2, as noted by fluorescence value consistent with the IgG control, indicating that umbilical cell lines lack the cell surface molecules required to directly stimulate CD4+ T cells. Histograms of umbilical cord tissue-derived cells analyzed by flow cytometry show positive expression of PD-L2, as noted by the increased value of fluorescence relative to the IgG control, and negative expression of CD178 and HLA-G, as noted by fluorescence value consistent with the IgG control.

In the mixed lymphocyte reactions conducted with umbilical cord tissue-derived cell lines the average stimulation index ranged from 6.5 to 9, and that of the allogeneic positive controls ranged from 42.75 to 70. Umbilical cord tissue-derived cell lines were negative for the expression of the stimulating proteins HLA-DR, HLA-DP, HLA-DQ, CD80, CD86, and B7-H2, as measured by flow cytometry. Umbilical cord tissue-derived cell lines were negative for the expression of immuno-modulating proteins HLA-G and CD178 and positive for the expression of PD-L2, as measured by flow cytometry. Allogeneic donor PBMCs contain antigen-presenting cells expressing HLA-DR, DQ, CD8, CD86, and B7-H2, thereby allowing for the stimulation of naïve CD4+ T cells. The absence of antigen-presenting cell surface molecules on placenta- and umbilical cord tissue-derived cells required for the direct stimulation of naïve CD4+ T cells and the presence of PD-L2, an immunomodulating protein, may account for the low stimulation index exhibited by these cells in a MLR as compared to allogeneic controls.

EXAMPLE 7

Secretion of Trophic Factors by Umbilical Cord Tissue-Derived Cells

The secretion of selected trophic factors from umbilical cord tissue-derived cells was measured. Factors selected for detection included: (1) those known to have angiogenic activity, such as hepatocyte growth factor (HGF) (Rosen et al.

(1997) Ciba Found. Symp. 212:215-26), monocyte chemotactic protein 1 (MCP-1) (Salcedo et al. (2000) Blood 96; 34-40), interleukin-8 (IL-8) (Li et al. (2003) J. Immunol. 170:3369-76), keratinocyte growth factor (KGF), basic fibroblast growth factor (bFGF), vascular endothelial growth factor (VEGF) (Hughes et al. (2004) Ann. Thorac. Surg 77:812-8), matrix metalloproteinase 1 (TIMP1), angiopoietin 2 (ANG2), platelet derived growth factor (PDGF-bb), thrombopoietin (TPO), heparin-binding epidermal growth factor (HB-EGF), stromal-derived factor 1alpha (SDF-1 alpha); (2) those known to have neurotrophic/neuroprotective activity, such as brain-derived neurotrophic factor (BDNF) (Cheng et al. (2003) Dev. Biol. 258; 319-33), interleukin-6 (IL-6), granulocyte chemotactic protein-2 (GCP-2), transforming growth factor beta2 (TGFbeta2); and (3) those known to have chemokine activity, such as macrophage inflammatory protein 1 alpha (MIP1a), macrophage inflammatory protein 1beta (MIP1b), monocyte chemoattractant-1 (MCP-1), Rantes (regulated on activation, normal T cell expressed and secreted), I309, thymus and activation-regulated chemokine (TARC), Eotaxin, macrophage-derived chemokine (MDC), IL-8).

Cells from the umbilical cord as well as human fibroblasts derived from human neonatal foreskin were cultured in Growth Medium with penicillin/streptomycin on gelatin-coated T75 flasks. Cells were cryopreserved at passage 11 and stored in liquid nitrogen. After thawing of the cells, Growth Medium was added to the cells followed by transfer to a 15 milliliter centrifuge tube and centrifugation of the cells at 150×g for 5 minutes. The supernatant was discarded. The cell pellet was resuspended in 4 milliliters Growth Medium, and cells were counted. Cells were seeded at 375,000 cells/75 cm$^2$ flask containing 15 milliliters of Growth Medium and cultured for 24 hours. The medium was changed to a serum-free medium (DMEM-low glucose (Gibco), 0.1% (w/v) bovine serum albumin (Sigma), penicillin/streptomycin (Gibco)) for 8 hours. Conditioned serum-free medium was collected at the end of incubation by centrifugation at 14,000×g for 5 minutes and stored at −20° C. To estimate the number of cells in each flask, cells were washed with PBS and detached using 2 milliliters trypsin/EDTA. Trypsin activity was inhibited by addition of 8 milliliters Growth Medium. Cells were centrifuged at 150×g for 5 minutes. Supernatant was removed, and cells were resuspended in 1 milliliter Growth Medium. Cell number was estimated using a hemocytometer.

Cells were grown at 37° C. in 5% carbon dioxide and atmospheric oxygen. Placenta-derived cells (batch 101503) also were grown in 5% oxygen or beta-mercaptoethanol (BME). The amount of MCP-1, IL-6, VEGF, SDF-1alpha, GCP-2, IL-8, and TGF-beta 2 produced by each cell sample was measured by an ELISA assay (R&D Systems, Minneapolis, Minn.). All assays were performed according to the manufacturer's instructions.

Chemokines (MIP1a, MIP1b, MCP-1, Rantes, I309, TARC, Eotaxin, MDC, IL8), BDNF, and angiogenic factors (HGF, KGF, bFGF, VEGF, TIMP1, ANG2, PDGF-bb, TPO, HB-EGF were measured using SEARCHLIGHT® Proteome Arrays (Pierce Biotechnology Inc.). The Proteome Arrays are multiplexed sandwich ELISAs for the quantitative measurement of two to 16 proteins per well. The arrays are produced by spotting a 2×2, 3×3, or 4×4 pattern of four to 16 different capture antibodies into each well of a 96-well plate. Following a sandwich ELISA procedure, the entire plate is imaged to capture chemiluminescent signal generated at each spot within each well of the plate. The amount of signal generated in each spot is proportional to the amount of target protein in the original standard or sample.

MCP-1 and IL-6 were secreted by umbilical cord tissue-derived cells and dermal fibroblasts (Table 13). SDF-1 alpha was secreted by fibroblasts. GCP-2 and IL-8 were secreted by umbilical cord tissue-derived cells cultured in the presence of BME or 5% $O_2$-GCP-2 also was secreted by human fibroblasts. TGF-beta2 was not detectable by ELISA assay.

TABLE 13

ELISA assay results

| | MCP-1 | IL-6 | VEGF | SDF-1☐ | GCP-2 | IL-8 | TGF-β2 |
|---|---|---|---|---|---|---|---|
| Fibroblast | 17 ± 1 | 61 ± 3 | 29 ± 2 | 19 ± 1 | 21 ± 1 | ND | ND |
| Umbilical cord (022803) | 1150 ± 74 | 4234 ± 289 | ND | ND | 160 ± 11 | 2058 ± 145 | ND |
| Umbilical cord (071003) | 2794 ± 84 | 1356 ± 43 | ND | ND | 2184 ± 98 | 2369 ± 23 | ND |

Values presented are picograms/milliliter/million cells (n = 2, sem);
ND = Not Detected.

TIMP1, TPO, KGF, HGF, FGF, HBEGF, BDNF, MIP1b, MCP1, RANTES, I309, TARC, MDC, and IL-8 were secreted from umbilical cord tissue-derived cells (Tables 14 and 15). No Ang2, VEGF, or PDGF-bb were detected.

TABLE 14

SearchLight ® Multiplexed ELISA assay results

| | TIMP1 | ANG2 | PDGFbb | TPO | KGF | HGF | FGF | VEGF | HBEGF | BDNF |
|---|---|---|---|---|---|---|---|---|---|---|
| Hfb | 19306.3 | ND | ND | 230.5 | 5.0 | ND | ND | 27.9 | 1.3 | ND |
| U1 | 57718.4 | ND | ND | 1240.0 | 5.8 | 559.3 | 148.7 | ND | 9.3 | 165.7 |
| U3 | 21850.0 | ND | ND | 1134.5 | 9.0 | 195.6 | 30.8 | ND | 5.4 | 388.6 | hFB = human fibroblasts,
UI = umbilical cord tissue-derived cells (022803),
U3 = umbilical cord tissue-derived cells (071003),
ND = Not Detected.

TABLE 15

SearchLight ® Multiplexed ELISA assay results

|     | MIP1a | MIP1b | MCP1   | RANTES | I309 | TARC | Eotaxin | MDC  | IL8     |
|-----|-------|-------|--------|--------|------|------|---------|------|---------|
| hFB | ND    | ND    | 39.6   | ND     | ND   | 0.1  | ND      | ND   | 204.9   |
| P1  | 79.5  | ND    | 228.4  | 4.1    | ND   | 3.8  | 12.2    | ND   | 413.5   |
| U1  | ND    | 8.0   | 1694.2 | ND     | 22.4 | 37.6 | ND      | 18.9 | 51930.1 |
| P3  | ND    | ND    | 102.7  | ND     | ND   | 0.4  | ND      | ND   | 63.8    |
| U3  | ND    | 5.2   | 2018.7 | 41.5   | 11.6 | 21.4 | ND      | 4.8  | 10515.9 | hFB = human fibroblasts,
U1 = umbilical cord tissue-derived cells (022803),
U3 = umbilical cord tissue-derived cells (071003),
ND = Not Detected.

Umbilical cord tissue-derived cells secreted a number of trophic factors. Some of these trophic factors, such as HGF, bFGF, MCP-1 and IL-8, play important roles in angiogenesis. Other trophic factors, such as BDNF and IL-6, have important roles in neural regeneration.

EXAMPLE 8

Inhibition of IFN-gamma-Induced Expression of HLA-DR, DP, DQ on Expanded Human Umbilical Cord Tissue-Derived Cells by HMG-CoA Reductase Inhibitors Culture-expanded human umbilical cord tissue-derived cells (022803 P4) were seeded into 6-well tissue culture plates and cultured in Dulbecco's Modified Eagles Media (DMEM)-low glucose, 15% fetal bovine serum (FBS), penicillin/streptomycin (P/S), Betamercaptoethanol (BME) to approximately 70% confluence. The cells were then treated with media containing 10 µM of respective HMG-CoA reductase inhibitor (Simvastatic acid (Alexis Biochemicals, Lausen, Switzerland) formulated as 10 mM stock reagents in DMSO) or DMSO vehicle—0.1% (Sigma, St. Louis, Mo.) and incubated overnight. The media was removed by aspiration and replaced with media containing 500 U/ml rhIFN-gamma (BD Pharmingen, Franklin Lakes, N.J.) and 10M of respective HMG-CoA reductase inhibitor and incubated for 3 days. On day three, cells were harvested with trypsin.

Harvested cells were washed once with PBS and re-suspended in 100 µl of 3% FBS in PBS with 20 µl FITC-labeled HLA-DR,DP,DQ (BD Biosciences, Franklin Lakes, N.J.) or FITC-labeled IgG antibody (BD Biosciences, Franklin Lakes, N.J.) and incubated for one hour. Cells were washed once in PBS and resuspended in 500 µl PBS and analyzed on a FACSCalibur flow cytometer (BS Biosciences, Franklin Lakes, N.J.).

TABLE 16

HLA-DR, DP, DQ expression of hUTC as measured by FITC fluorescence intensity values of pre-treated with HMG-CoA reductase inhibitor and further treated with inflammatory cytokine IFN-gamma

| HMG-CoA Reductase Inhibitor Treatment | IgG control | | IFN-gamma-treated | | No cytokine treatment | |
|---|---|---|---|---|---|---|
| | mean | Std dev | mean | Std dev | Mean | Std dev |
| Untreated | 4.88 | 5.12 | 274.23 | 219.04 | 5.56 | 8.97 |
| 0.1% DMSO vehicle control | 4.09 | 5.67 | 294.08 | 257.08 | 5.54 | 5.46 |
| Simvastatin | 4.4 | 2.38 | 5.57 | 3.98 | 5.66 | 3.25 |

As shown in Table 16, untreated and 0.1% DMSO vehicle control human umbilical cord tissue-derived cells incubated with the inflammatory cytokine IFN-gamma showed an increase in HLA-DR, DP, DQ expression as seen by increased fluorescence detected by flow cytometry. Human umbilical cord tissue-derived cells pre-treated with a HMG-CoA reductase inhibitor and subsequently incubated with IFN-gamma showed HLA-DR, DP, DQ expression similar to untreated and vehicle controls.

This data indicates that HMG-CoA reductase inhibits inflammatory cytokine-mediated expression of HLA-DR, DP, DQ in human umbilical cord tissue-derived cells.

EXAMPLE 9

Renoprotective Efficacy of Human Umbilical Cord Tissue-Derived Cells in Rodent Model of Drug-Induced Acute Renal Failure Fifty-eight, female C57BL/6J mice were purchased from The Jackson Laboratory (Bar Harbor, Me.). Table 17 describes the experimental design that was implemented in this study.

TABLE 17

Experimental design. Mouse mesenchymal stem cells (mMSC). Human mesenchymal stem cells (hMSCs). Hanks Balanced Salt Solution vehicle control (HBSS). Number of viable cells injected (Cell dose). Human umbilical cord tissue-derived cells (hUTC)

| Treatment group | Number of animals | Gender | Test material | Cell dose |
|---|---|---|---|---|
| 1 | 14 | Female | HBSS | NA |
| 2 | 10 | Female | mMSC | $0.2 \times 10^6$ |
| 3 | 10 | Female | hMSC | $0.2 \times 10^6$ |
| 4 | 10 | Female | hUTC | $0.2 \times 10^6$ |
| 5 | 14 | Female | hUTC | $0.4 \times 10^6$ |

Acute renal failure was induced in mice using two subcutaneous injections of cis-diaminedichloroplatinum (cisplatin) (Sigma Co. Cat# P4394) at a concentration of 10 mg/kg each, followed by infusion of cells or Hanks Balanced Salt Solution (HBSS), without $Ca^{++}/Mg^{++}$ (Invitrogen, Cat#14025, Lot#1300696) twenty-four to forty-eight hours after the initial cisplatin injection. FIG. 1 shows the sequence of events for the execution of this study.

Passage 10 hUTCs (lot#120304) were isolated and expanded and cryopreserved at <−120° C. (liquid nitrogen vapor phase). Following manufacturer's instructions, hMSCs (Cambrex (Lonza), Walkersville, Md.) Cat # PT-2501, Lot # 4F1560) were expanded to passage 6 and then cryopreserved. Mouse MSC (mMSC) were freshly isolated and expanded.

Briefly, C57BL/6J mouse bone marrow was flushed from the tibia and femur using a 25-gauge needle. Bone marrow was cultured at 1–2×10$^6$ cells/cm$^2$ in Iscove's modified Dulbecco's medium that was supplemented with 10% fetal serum. The nonadherent cells were removed and media was exchanged at 48-72 hours post-seeding, as well as every four days thereafter. When the tissue culture flasks were near confluency, mMSCs were enzymatically removed from the culture flask. After two passages, mMSCs were harvested and prepared for transplantation. Both hUTC and hMSCs demonstrated a normal karyotype and were devoid of pathogen and mycoplasma contamination.

At the time of cell injection, hUTCs and hMSCs were thawed at 37° C. and washed two times with HBSS. Cells were counted using a hemocytometer and cell viability was determined by trypan blue dye exclusion. Cells were reconstituted at a concentration of 0.2×10$^6$/200 μl HBSS or 0.4×10$^6$ cells/200 μl HBSS. Cells suspended in HBSS or HBSS alone (as negative control) were injected into the anterior facial vein using a 1 mL syringe fitted with a 27-gauge needle.

Figure 2:
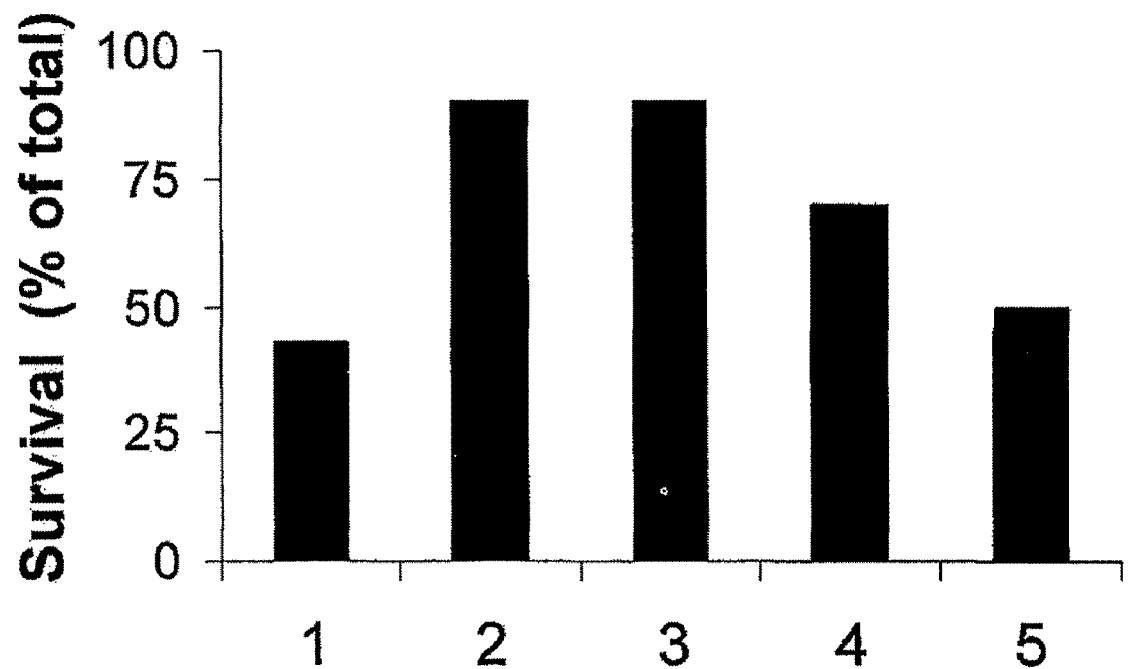
FIG. 2 shows the animal survival rate after induction of kidney damage and transplantation with umbilical cord tissue-derived cells. Treatment group number shown on the x-axis.

To determine the animal survival rate, the number of living animals on day 7 post cell transplantation was divided by the initial number of animals in the treatment group. As shown in Table 18 and FIG. 2, HBSS vehicle treatment resulted in only 43% of the animals surviving on day 7-post cell translation. However, both mMSC and hMSC treatment resulted in 90% animal survival. The lower dose (0.2×10$^6$ cells) injection of hUTCs resulted in 70% of the animals surviving on day 7, and the higher dose (0.4×10$^6$ cells) hUTC treatment resulted in only 50% animal survival.

TABLE 18

Survival rate. On day 7-post cell transplantation, the percentage of surviving animals was determined

| Treatment | Dose | Percent survival |
|---|---|---|
| 1 | NA | 43 |
| 2 | 0.2 × 10$^6$ | 90 |
| 3 | 0.2 × 10$^6$ | 90 |
| 4 | 0.2 × 10$^6$ | 70 |
| 5 | 0.4 × 10$^6$ | 50 |

Blood samples (50 μl) were collected from the tail vein prior to cisplatin injections (day-1) and on days 3, 5, and 7 post cell transplantation. Serum was prepared from the blood samples and stored at −80° C. in EDTA treated tubes until the time of analysis. Food was removed, overnight, from all animals prior to blood sampling. Blood-Urea-Nitrogen (BUN) measurements were conducted using a COBAS Mira Chemical Analyzer (Roche, Switzerland). Serum creatinine (SCr) was analyzed using an Advia 1650 Chemical Analyzer (Bayer, Pittsburgh, Pa.).

Figure 3:
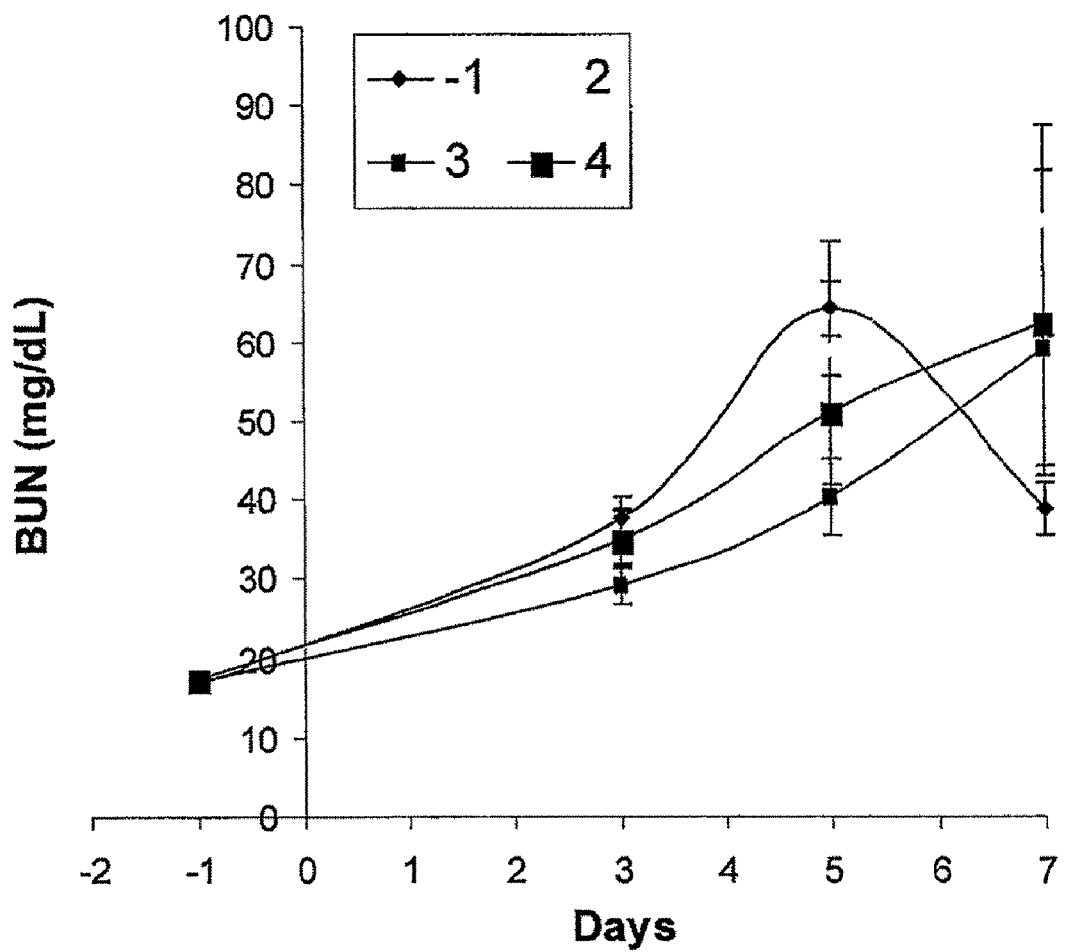
FIG. 3 shows BUN measurements in mice. Serum samples were collected on day 1-, 3-, 5- and 7-post cell transplantation and BUN was measured. Error bars represent SEM.

Prior to injury, HBSS, mMSC, hMSC, lower dose hUTC and higher dose hUTC all showed normal BUN values of 16.89 mg/dl, 17.19 mg/dl, 17.21 mg/dl, 17.47 mg/dl, 17.33 mg/dl respectively (Table 19, FIG. 3). However, on day five all treatment groups showed elevated BUN levels. HBSS treatment resulted in an average BUN of 64.37 mg/dl and mMSC treatment 58.96 mg/dl. However, both hMSC and lower dose hUTC treatment resulted in reduced BUN values of 40.44 mg/dl and 51.32 mg/dl respectively, while a higher dose hUTC treatment showed an elevated BUN of 97.28 mg/dl. No statistical differences were observed between vehicle and treatment groups. This was due to the variability that is typically seen with BUN measurements. Day 7 measurements showed a similar trending data, however a dramatic reduction in vehicle group BUN values was observed. This made it difficult to accurately assess the effects of cell treatment on renal function at 7 days post transplantation.

TABLE 19

BUN Measurements

| | \multicolumn{8}{c}{Day:} |
|---|---|---|---|---|---|---|---|---|
| | −1 | 3 | 5 | 7 | −1 | 3 | 5 | 7 |
| | \multicolumn{4}{c}{Treatment group: 1} | \multicolumn{4}{c}{Treatment group: 2} |
| BUN (mg/dl) | 18.85 | 35.20 | 32.83 | 41.68 | 11.22 | 37.57 | 55.84 | 66.73 |
| | 20.75 | 41.61 | 78.62 | 45.96 | 22.70 | 33.80 | 79.56 | 111.80 |
| | 15.85 | 28.59 | 32.88 | 51.88 | 17.57 | 46.28 | 97.34 | 121.74 |
| | 15.91 | 52.75 | 112.33 | 28.77 | 19.55 | 26.73 | 37.88 | 60.97 |
| | 21.02 | 40.60 | 57.43 | 24.39 | 17.81 | 34.15 | 49.94 | 116.65 |
| | 14.36 | 42.72 | 46.98 | 30.67 | 14.27 | 48.59 | 89.96 | 23.68 |
| | 17.45 | 30.83 | 39.09 | 41.68 | 19.63 | 17.98 | 11.54 | 74.05 |
| | 19.99 | 35.22 | 80.53 | 45.96 | 17.17 | 27.27 | 50.23 | 78.61 |
| | 19.69 | 28.38 | 88.69 | | 15.95 | 45.71 | 58.37 | 25.30 |
| | 14.27 | 25.75 | 120.36 | | 15.99 | | | |
| | 12.16 | 59.32 | 77.01 | | | | | |
| | 16.23 | 38.21 | 35.80 | | | | | |
| | 15.15 | 31.66 | 34.25 | | | | | |
| | 15.15 | | | | | | | |
| Average | 16.92 | 37.76 | 64.37 | 38.87 | 17.19 | 35.34 | 58.96 | 75.50 |
| Std: | 2.74 | 9.80 | 30.75 | 9.74 | 3.15 | 10.32 | 26.74 | 36.49 |
| SEM | 0.71 | 2.72 | 8.53 | 3.44 | 1.00 | 3.44 | 8.91 | 12.16 |
| | \multicolumn{4}{c}{Treatment group: 3} | \multicolumn{4}{c}{Treatment group: 4} |
| BUN (mg/dl) | 15.77 | 19.07 | 20.60 | 41.86 | 14.52 | 35.76 | 72.09 | 108.61 |
| | 17.79 | 24.94 | 36.81 | 38.75 | 17.24 | 34.48 | 68.90 | 33.84 |
| | 16.59 | 25.75 | 32.03 | 44.21 | 14.23 | 56.19 | 62.37 | 35.62 |
| | 17.09 | 31.60 | 40.95 | 117.98 | 17.65 | 27.25 | 23.32 | 23.39 |
| | 18.46 | 37.49 | 51.86 | 43.78 | 16.83 | 24.76 | 30.53 | 111.16 |
| | 16.72 | 38.31 | 69.33 | 39.17 | 15.39 | 20.93 | 21.88 | |
| | 15.76 | 34.87 | 47.99 | 24.02 | 18.23 | 34.01 | 89.88 | |
| | 17.55 | 17.22 | 17.55 | 157.38 | 20.76 | 33.72 | 73.36 | |
| | 17.28 | 34.23 | 49.43 | 28.04 | 20.14 | 46.90 | 65.91 | |
| | 19.05 | 29.33 | 37.84 | | 19.69 | | | |
| Average | 17.21 | 29.28 | 40.44 | 59.47 | 17.47 | 34.89 | 51.32 | 62.52 |
| Std: | 1.07 | 7.39 | 15.32 | 45.94 | 2.30 | 10.94 | 28.43 | 43.50 |
| SEM | 0.34 | 2.34 | 4.84 | 15.31 | 0.73 | 3.65 | 9.48 | 19.45 |

| | \multicolumn{4}{c}{Day:} |
|---|---|---|---|---|
| | −1 | 3 | 5 | 7 |
| | \multicolumn{4}{c}{Treatment group: 5} |
| BUN (mg/dl) | 15.78 | 104.42 | 92.85 | 222.03 |
| | 15.22 | 44.20 | 92.10 | 47.15 |
| | 14.34 | 42.41 | 53.20 | 74.12 |
| | 11.70 | 27.39 | 29.54 | |
| | 22.54 | 28.69 | 118.43 | |
| | 19.44 | 43.17 | 92.68 | |
| | 18.72 | 55.16 | 113.65 | |
| | 18.83 | 33.37 | 43.05 | |
| | 21.28 | 142.07 | 54.15 | |
| | 13.02 | 26.43 | 111.03 | |
| | 17.45 | 25.46 | 269.38 | |
| | 18.56 | 78.26 | | |
| | 18.41 | | | |
| | 17.30 | | | |
| Average | 17.33 | 54.25 | 97.28 | 114.43 |
| Std: | 3.04 | 36.41 | 64.75 | 94.15 |
| SEM | 0.81 | 10.51 | 19.52 | 54.36 |

Figure 4:
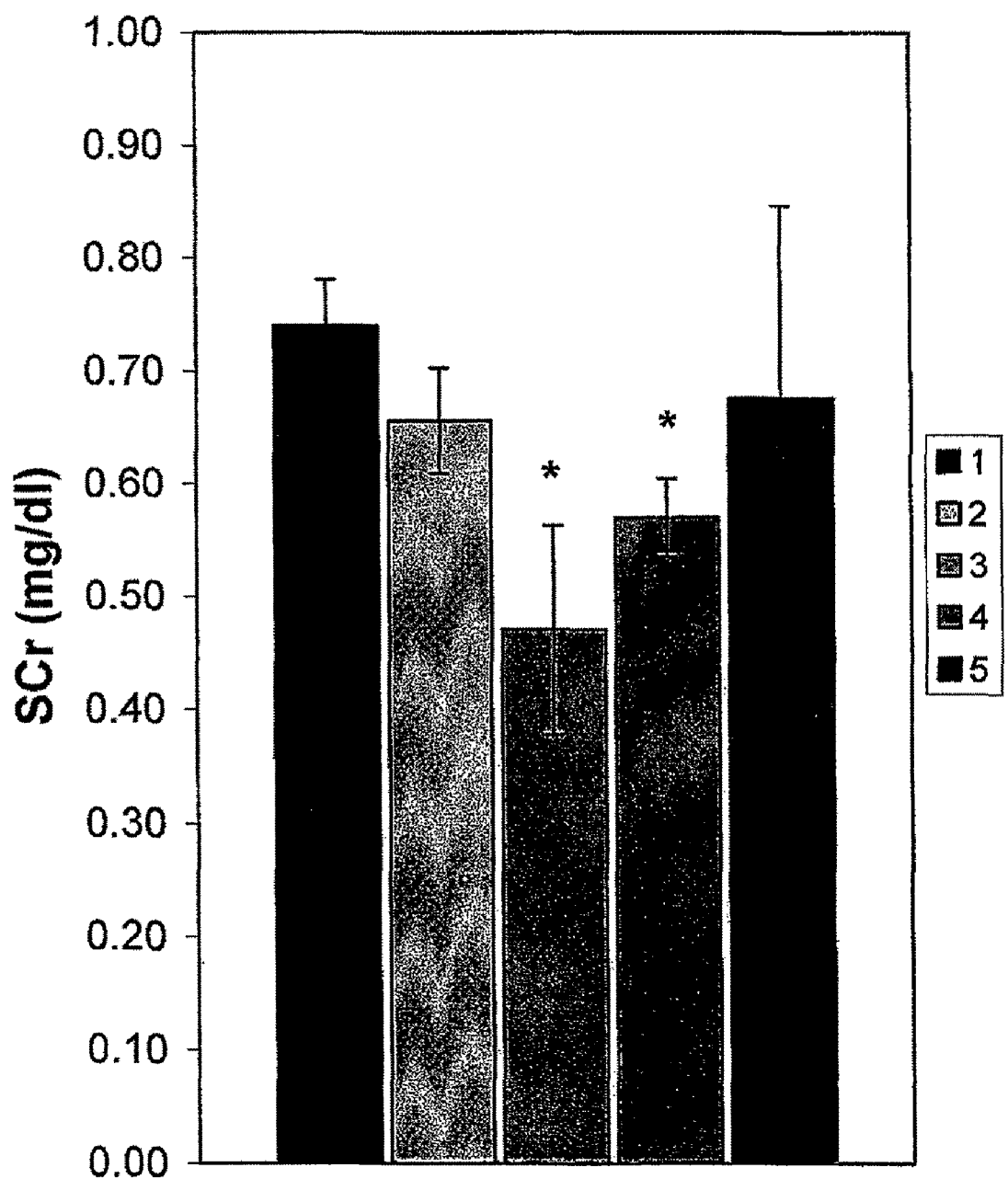
FIG. 4 shows the results from serum creatinine measurements. Error bars represent the standard error of the mean. (*) P<0.03.

Table 20 and FIG. 4 shows SCr measurements from day 5 serum samples. HBSS and mMSC treatment resulted in mean creatinine values of 0.74 mg/dl and 0.66 mg/dl, respectively. A statistically significant reduction in SCr was observed after hMSC or lower dose hUTC treatment (P<0.03). hMSC treatment resulted in a mean SCr value of 0.47 mg/dl and lower dose hUTC treatment resulted in a mean SCr value of 0.57 mg/dl.

TABLE 20

Serum creatinine. SCr was measured on day 5-post cell transplantation. Standard deviation (std). Standard error of the mean (SEM)

| Treatment Group | Test material | Creatinine mg/dl | Mean | Std | SEM | P-value |
|---|---|---|---|---|---|---|
| 1 | HBSS | 0.64 | 0.74 | 0.09 | 0.04 | na |
|   | HBSS | 0.72 |   |   |   |   |
|   | HBSS | 0.72 |   |   |   |   |
|   | HBSS | 0.89 |   |   |   |   |
|   | HBSS | 0.73 |   |   |   |   |
| 2 | mMSC | 0.64 | 0.66 | 0.10 | 0.05 | 0.213 |
|   | mMSC | 0.72 |   |   |   |   |
|   | mMSC | 0.72 |   |   |   |   |
|   | mMSC | 0.48 |   |   |   |   |
|   | mMSC | 0.72 |   |   |   |   |
| 3 | hMSC | 0.24 | 0.47 | 0.21 | 0.09 | 0.008 |
|   | hMSC | 0.27 |   |   |   |   |
|   | hMSC | 0.56 |   |   |   |   |
|   | hMSC | 0.56 |   |   |   |   |
| 4 | hUTC | 0.64 | 0.57 | 0.08 | 0.03 | 0.028 |
|   | hUTC | 0.45 |   |   |   |   |
|   | hUTC | 0.56 |   |   |   |   |
|   | hUTC | 0.64 |   |   |   |   |
| 5 | hUTC | 1.28 | 0.68 | 0.38 | 0.17 | 0.789 |
|   | hUTC | 0.26 |   |   |   |   |
|   | hUTC | 0.48 |   |   |   |   |
|   | hUTC | 0.72 |   |   |   |   |

Two mice per treatment group were sacrificed on day 7 post cell transplantation and tissues were fixed by transcardial perfusion with saline, followed by perfusion and immersion in 4% paraformaldehyde. Kidneys were removed from the mice and processed for histology. H&E stained sections were then assessed for histological injury. Two trained pathologists blindly assessed and scored the degree of renal tubular degeneration.

Figure 5:
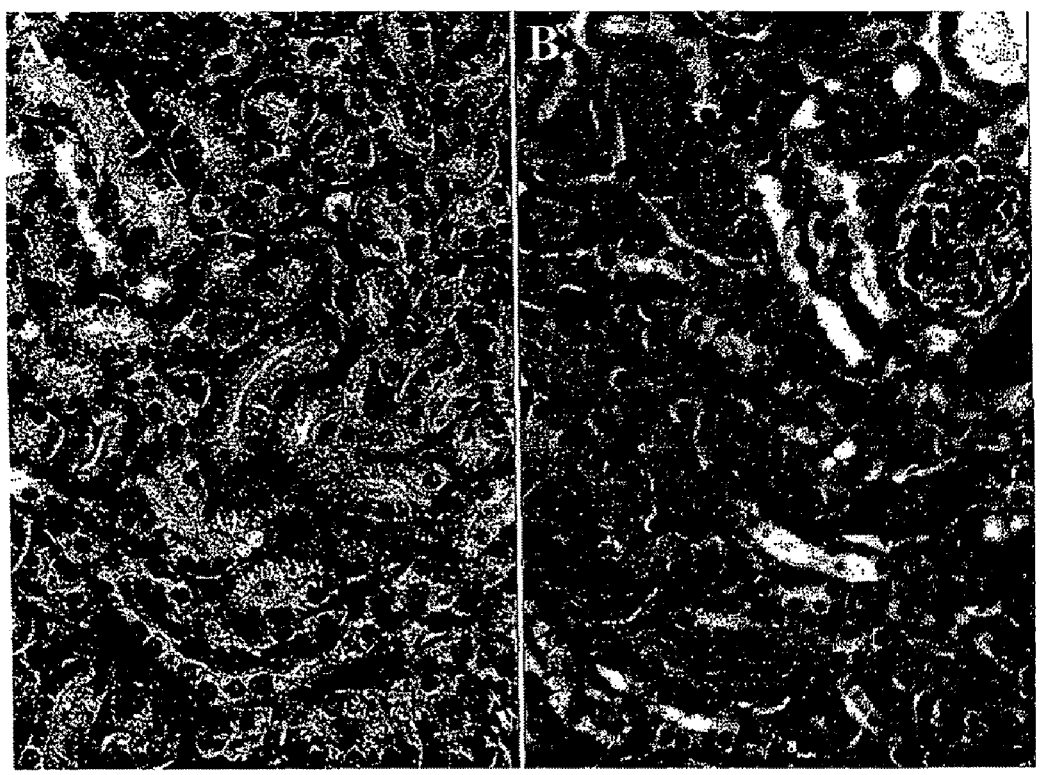
FIG. 5 shows representative histological images. Histological sections were scored for degree of tubular degeneration. A) Vehicle treatment group. B) hUTC (0.2e6 cell dose) treatment group. Representative tubule with significant degeneration.

Tubular necrosis was qualitatively measured in histological sections from HBSS, hMSC and lower dose hUTC treated animals. Tubular degeneration was scored on a scale ranging from 1 to 4 (1=minimal damage, 2=mild damage, 3=moderate damage, 4=severe damage). As shown in Table 21 and FIG. 5, both vehicle and hMSC treatment resulted in mild tubular degeneration, with a mean injury score of 2.5. However, a lower dose hUTC treatment resulted in minimal tubular damage with a mean injury score of 1.9 indicative of the renoprotective potential of hUTC.

TABLE 21

Histological injury evaluation. Extent of tubular degeneration was scored independently, by two pathologist (Pathologist A, B). Pathologists were blinded to the treatment group assignments

|   | Vehicle |   | hMSC |   | hUTC (low dose) |   |
|---|---|---|---|---|---|---|
| Animal Number | 1 | 2 | 3 | 4 | 5 | 6 |
| Pathologist A | 3 | 3 | 3 | 2 | 2.5 | 2 |
| Pathologist B | 2 | 2 | 3 | 2 | 1 | 2 |
| Mean Score | Mild (2.5) |   | Mild (2.5) |   | Minimal (1.9) |   |

Values represent injury scores using the following assessment scale, 1 = minimal, 2 = mild, 3 = moderate, 4 = severe.

The data show that both hUTCs and hMSCs protect the kidneys from cisplatin-induced nephrotoxicity. This study utilizes a very high concentration of cisplatin and therefore represents a model of severe nephrotoxicity. Future studies will utilize a lower, sub-lethal dose of cisplatin. This lower dose nephrotoxicity model will be more representative of the type of injury observed in humans. In addition, intravenous administration of hUTCs will occur at least twenty-four hours after cisplatin infusion. This will ensure that the blood levels of cisplatin are very low and less likely to exert negative affects on hUTCs.

Treatment of injured mice with $0.2 \times 10^6$ hUTC resulted in an increased rate of survival, a 23% reduction in SCr and reduced tubular degeneration as compared to vehicle treated animals. These significant findings indicate that hUTC might protect the kidney from drug-induced acute renal failure.

EXAMPLE 10

Evaluation of the Renoprotective Efficacy of Human Umbilical Cord Tissue-Derived Cells in a Rat Model of Cisplatin Induced Nephrotoxicity Nephrotoxicity was induced in thirty-nine male Sprague Dawley rats. Cis-diaminedichloroplatinum (cisplatin) (Sigma Co. Cat# P4394, Lot# 076K1697) was administered (6 mg/kg) via intraperitoneal (IP) injection, twenty-four hours prior to cell administration. The animals were dosed at a volume of 5 mL/kg, and dose levels were based upon the most recently collected body weight.

Passage 10, hUTC (lot#Q091506) were isolated, expanded, and cryopreserved at <−120° C. (liquid nitrogen vapor phase). hUTC demonstrated a normal karyotype and were devoid of pathogen and mycoplasma contamination.

At the time of cell transplantation, hUTC were thawed at 37° C., washed two times with HBSS and resuspended in HBSS at the appropriate concentration. Animals were dosed once, twenty-four hours after cisplatin administration, on Day 1 via intravenous (IV) injection with vehicle (Hanks Balanced Salt Solution (HBSS), without $Ca^{++}/Mg^{++}$ (Invitrogen, Cat#14025, Lot #1226569)) or with hUTC at a volume of 2 mL and an approximate infusion rate of two minutes. See Table 22 for treatment group assignments. Group 1 received vehicle only, and Groups 2-4 received hUTC at levels of $0.3 \times 10^6$, $1 \times 10^6$ and $3 \times 10^6$ cells per animal. The animals were approximately 7-8 weeks old at the time of dosing.

TABLE 22

Experimental Design

| Treatment group | Number of animals | Gender | Test material | Cell dose |
|---|---|---|---|---|
| 1 | 10 | Male | Vehicle | NA |
| 2 | 10 | Male | hUTC | $0.3 \times 10^6$ |
| 3 | 9 | Male | hUTC | $1.0 \times 0^6$ |
| 4 | 10 | Male | hUTC | $3.0 \times 0^6$ |

Blood samples were collected prior to cell or vehicle treatment (day 1) and on days 4, 6 and 8-post cisplatin treatment by puncture of a tail vein. Blood samples were processed for serum, and then both BUN and SCr were measured using an Olympus AU640 chemistry immuno analyzer.

Figure 6:
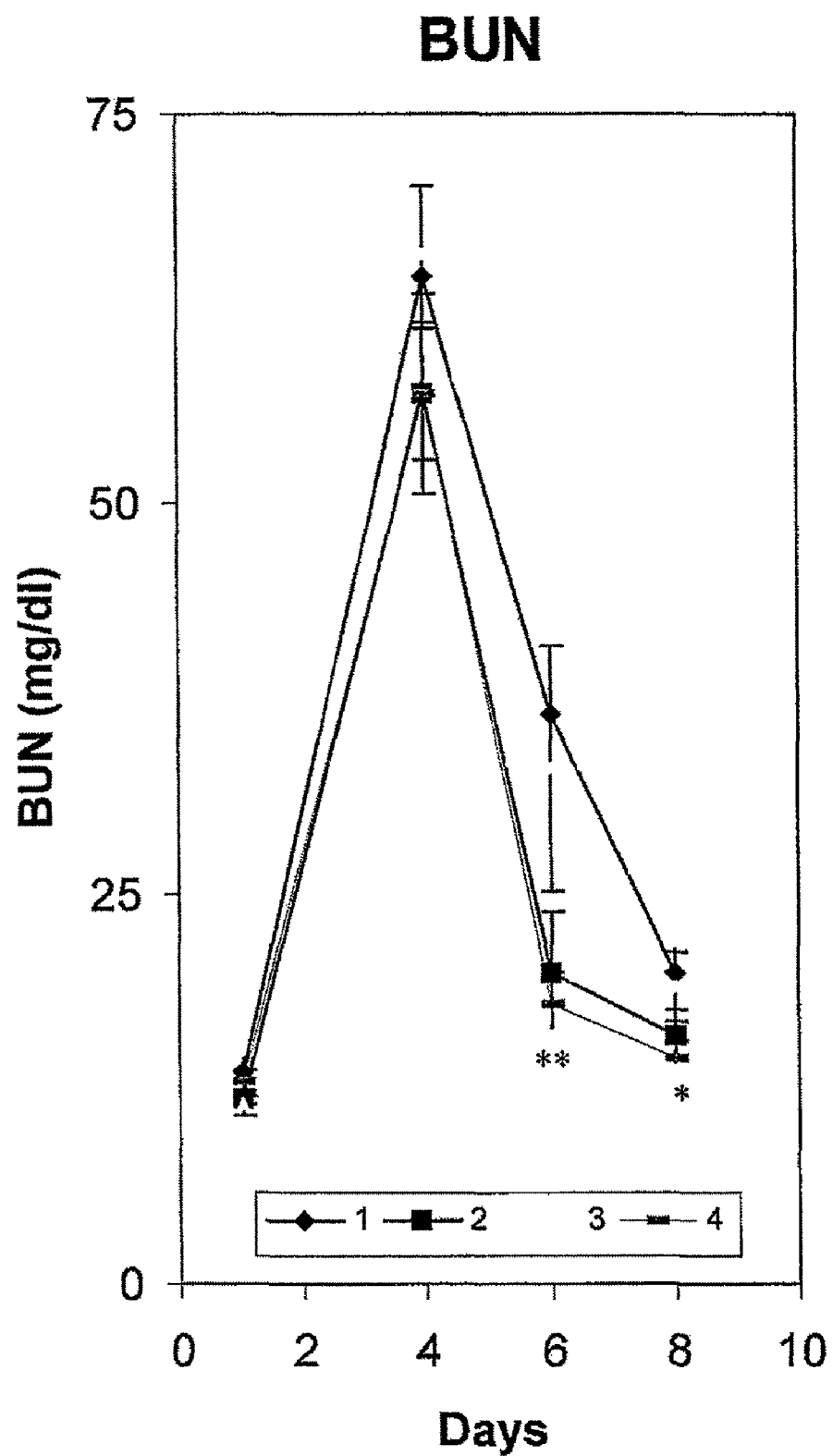
FIG. 6 shows BUN analysis in rats. Error bars represent standard error of the mean. ** p value<0.005. * p value<0.03.
Figure 7:
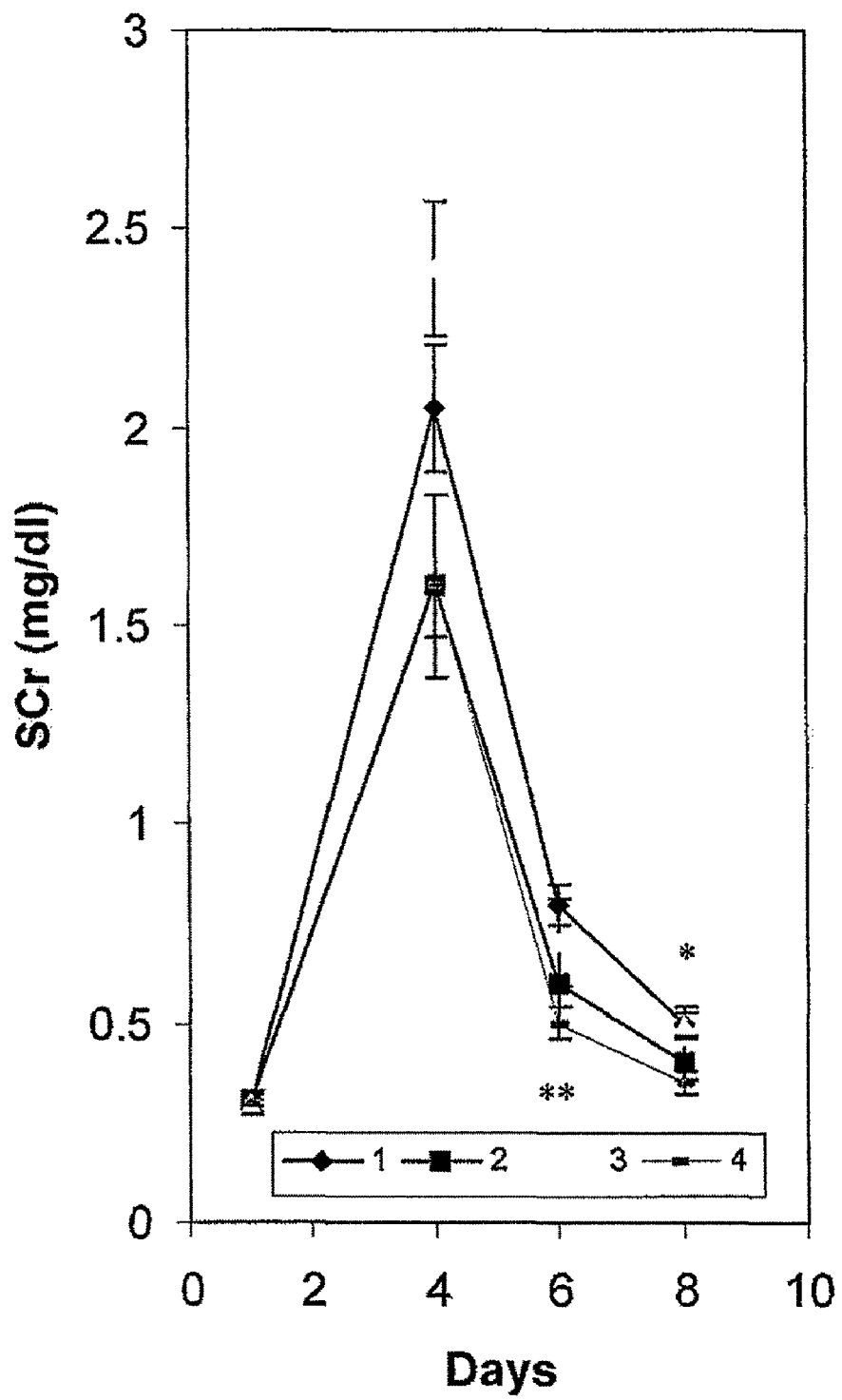
FIG. 7 shows SCr analysis in rats. Error bars represent standard error of the mean. ** p value<0.005. * p value<0.03.

Blood samples were evaluated for Bun and SCr on Days 1, 4, 6, and 8 (Table 23, FIG. 6, FIG. 7). All animals were administered cisplatin (Groups 1-4) and showed similar baseline levels, with marked increases in mean BUN and SCr levels for all groups from Day 1 to Day 4. All treatment groups showed a marked increase in both Bun and SCr levels, with the treatment group mean levels ranging from 12-13 mg/dL (Bun) and 0.3 mg/dL (SCr) on Day 1 to 62-68 mg/dL (Bun) and 1.8-2.2 mg/dL (SCr) on Day 4. However, vehicle control animals (Group 1) showed decreased mean Bun and SCr by Day 6 (34±10.4 mg/dL and 0.8±0.2 mg/dL, respectively), which further decreased by Day 8, approaching baseline levels (19±4.1 mg/dL and 0.5±0.1 mg/dL, respectively). This suggests that the nephrotoxicity was transient and began to reverse by Day 6 with Bun and SCr levels nearly at baseline by Day 8. Likewise, the Bun and SCr levels for the animals administered hUTC (Groups 2-4) were comparable or slightly lower than those of the vehicle control animals (Group 1). There appeared to be little effect of cell treatment at a dose level of $0.3\times10^6$ (Group 2) and $1\times10^6$ cells/animal (Group 3) on both days 6 and 8. However, treatment with hUTC at a dose level of $3\times10^6$ cells/animal (Group 4) resulted in a significant decrease in both mean Bun and SCr values on Day 6 (20±6.1 mg/dL and 0.5±0.12 mg/dL, respectively).

TABLE 23

Serum chemistry analysis

| Treatment group | | Day 1 | Day 4 | Day 6 | Day 8 |
|---|---|---|---|---|---|
| BUN | | | | | |
| 1 - vehicle | Mean (mg/dl) | 13.5 | 64.5 | 36.5 | 20 |
| | SEM (mg/dl) | 0.99 | 4.36 | 3.29 | 1.45 |
| 2 - 0.3 × 10$^6$ | Mean | 12 | 57 | 20 | 16 |
| | SEM | 0.51 | 4.22 | 3.87 | 1.54 |
| 3 - 1.0 × 10$^6$ | Mean | 11.5 | 66 | 33 | 19 |
| | SEM | 0.62 | 4.47 | 7.85 | 2.19 |
| 4 - 3.0 × 10$^6$ | Mean | 13 | 57 | 18 | 14.5 |
| | SEM | 0.77 | 6.47 | 1.93 | 1.12 |
| SCr | | | | | |
| 1 - vehicle | Mean (mg/dl) | 0.3 | 2.05 | 0.8 | 0.5 |
| | SEM (mg/dl) | 0.01 | 0.16 | 0.05 | 0.03 |
| 2 - 0.3 × 10$^6$ | Mean | 0.3 | 1.6 | 0.6 | 0.4 |
| | SEM | 0.01 | 0.13 | 0.06 | 0.04 |
| 3 - 1.0 × 10$^6$ | Mean | 0.3 | 2.4 | 0.7 | 0.5 |
| | SEM | 0.02 | 0.17 | 0.11 | 0.04 |
| 4 - 3.0 × 10$^6$ | Mean | 0.3 | 1.6 | 0.5 | 0.35 |
| | SEM | 0.03 | 0.23 | 0.04 | 0.03 |

Before cell treatment and on days 4, 6, and 8 (before necropsy), animals were placed into metabolism cages, and urine samples were collected on ice, after a duration of approximately 8-10 hours. Urine volume was measured and the total duration of the urine collection period was recorded. Urine samples were then analyzed for creatinine using an Olympus AU640 chemistry immuno analyzer. Creatinine clearance (CrCl) was determined using the following equation; CrCl=urine creatinine (mg/dL)×urine volume (mL/hour)/[serum creatinine (mg/dL)×body weight (kg)].

Figure 8:
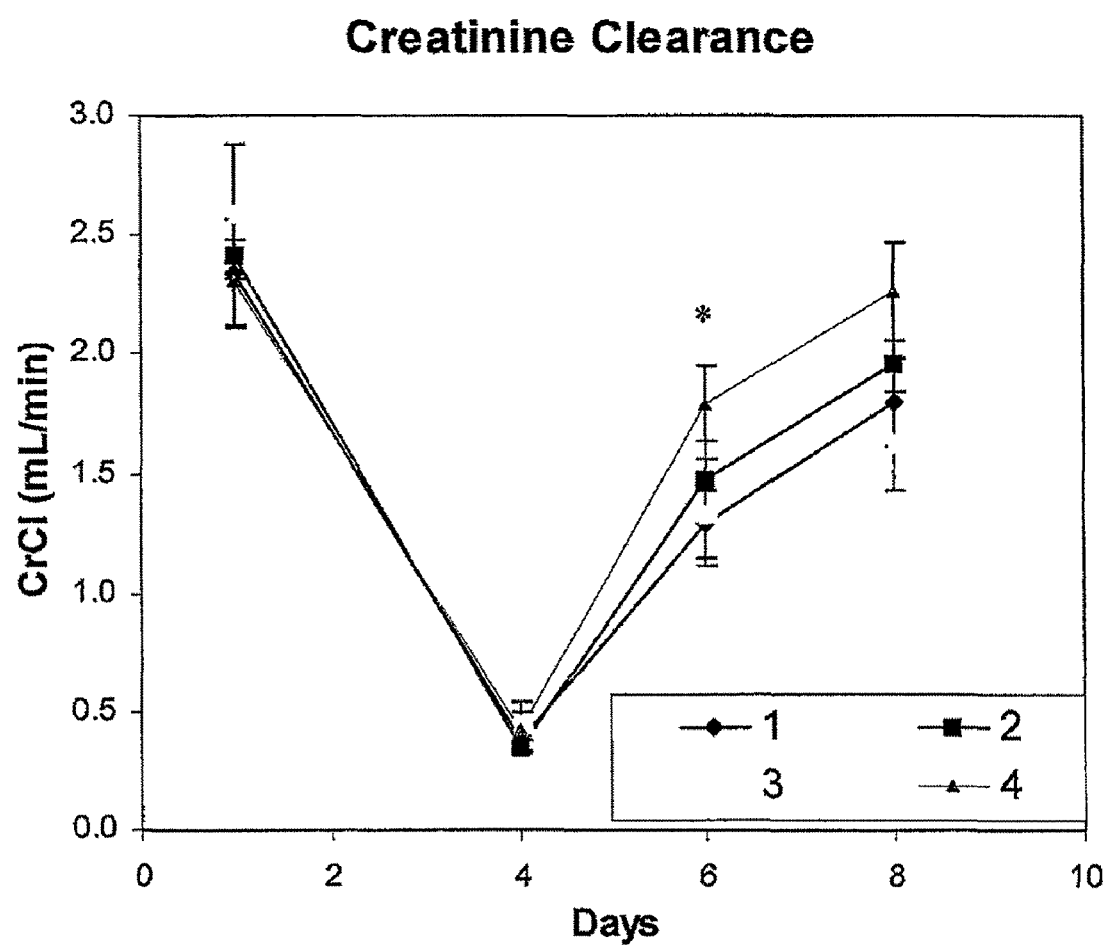
FIG. 8 shows CrCl analysis in rats. Error bars represent standard error of the mean. * p value<0.03.

Urine samples were evaluated for SCr on Days 1, 4, 6, and 8 and then CrCl was calculated (Table 24, FIG. 8). All animals were administered cisplatin and showed similar baseline levels, with a dramatic decrease in mean CrCl values for all groups from Day 1 to Day 4. All treatment groups showed a marked increase in CrCl, with the mean levels ranging from 2.304-2.595 ml/min on Day 1 to 0.381-0.459 ml/min on Day 4. Vehicle control animals showed an increase in CrCl on Day 6 (1.290 ml/min), which further increased by Day 8, approaching baseline levels (1.802 ml/min). This confirms the transient nature of the nephrotoxic injury as renal function began to improve by Day 6 with CrCl levels nearly at baseline by Day 8. Likewise, CrCl for the animals administered hUTC (Groups 2-4) were comparable or slightly lower than those of the vehicle control animals. Treatment with hUTC at a dose level of $3\times10^6$ cells/animal (Group 4) showed an improved CrCl, compared to vehicle control, on Day 6 (1.792 ml/min verses 1.290 mL/min in the vehicle control).

TABLE 24

CrCl Analysis

| Treatment group | | Day 1 | Day 4 | Day 6 | Day 8 |
|---|---|---|---|---|---|
| 1 - vehicle | Mean (mL/min) | 2.337 | 0.381 | 1.290 | 1.802 |
| | SEM (mL/min) | 0.225 | 0.056 | 0.143 | 0.185 |
| 2 - 0.3 × 10$^6$ | Mean | 2.415 | 0.350 | 1.471 | 1.956 |
| | SEM | 0.164 | 0.030 | 0.168 | 0.214 |
| 3 - 1.0 × 10$^6$ | Mean | 2.595 | 0.459 | 1.340 | 1.632 |
| | SEM | 0.282 | 0.078 | 0.220 | 0.204 |
| 4 - 3.0 × 10$^6$ | Mean | 2.304 | 0.420 | 1.792 | 2.264 |
| | SEM | 0.177 | 0.080 | 0.152 | 0.202 |

The renoprotective effects of hUTC in a rat model of cisplatin-induced nephrotoxicity are described. Administration of $3.0e^6$ hUTC resulted in a moderate reduction in BUN, SCr and an increase in CrCl compared to vehicle control treatment. Cisplatin is one of the most common anti tumor agents used in the chemotherapy of malignancies. Therefore, the administration of hUTC protects the kidney for nephrotoxic injury, ultimately improving the outcome and quality of life for cancer patients undergoing chemotherapy. In addition, hUTC treatment may reduce the severity of acute tubular necrosis and even prevent ARF associated with other medical interventions such as those observed after cardiovascular surgery as well as in some patients receiving antimicrobial drugs, iodide contrast agents, anesthetics, immunosuppressants and analgesics.

EXAMPLE 11

Evaluation of the Renoprotective Efficacy of Human Umbilical Cord Tissue-Derived Cells in a Rodent Model of Obstructive Nephropathy The purpose of this prophetic example is to evaluate the renoprotective effects of human umbilical cord tissue-derived cells (hUTC) in a unilateral ureter obstruction (UUO) model of renal injury. The UUO model is an effective model for short-term, obstructive nephropathy and tubulointerstitial fibrosis. To evaluate renoprotective efficacy, cell biodistribution, blood-urea-nitrogen (BUN), serum creatinine (SCr) and histological injury will be assessed in injured mice twelve days post cell transplantation.

Female C57BL/6J mice (The Jackson Laboratory, Bar Harbor, Me.) will be anesthetized with 1-3% Isofluorane. The abdomen of each animal will be shaved and cleaned with 70% alcohol, followed by betadine. A midline, abdominal incision will be made. The abdominal wall will be opened and the intestines will be moved out onto the chest and protected with wet gauze. The left kidney will be located and the ureter dissected free of fat. Two, 8-0 non-absorbable ties will be placed on the ureter. The intestines will then be returned to the abdomen and one cubic centimeter of warm saline will be placed into the peritoneal cavity. The muscle layer will be closed with 4-0 Dexon and the skin closed with staples. Isoflurane will be discontinued and the mice will be allowed to recover with 100% oxygen on a heating pad until ambulatory.

Immediately after animals recovered from surgery, hUTC will be thawed at 37° C., washed two times in Hanks Balanced Salt Solution w/o Ca$^{++}$/Mg$^{++}$ (HBSS) and resuspended in one milliliter of HBSS. Cells will then be counted using a hemocytometer and cell viability will be determined by trypan blue dye exclusion. Cells will be reconstituted at a concentration of $1.0\times106$ viable cells/milliliter in HBSS. Cells suspended in 200 microliters of HBSS will then be transplanted, via tail vein injection, using a one-milliliter syringe fitted with a 27-gauge needle.

All animals will be sacrificed on day 12 post cell transplantation by carbon dioxide asphyxiation. Kidneys, lungs, brain and heart will be removed from each animal. Half of each kidney will then be fixed in 10% neutral buffered formalin for histological analysis. The remaining kidney half, and all other organs will be snap frozen in liquid nitrogen. All frozen organs will then be homogenized using an Omni TH homogenizer fitted with a 7 mm disposable rotor stator generator probe (Omni International, Inc., Marietta, Ga.). Total RNA will then be extracted using an RNeasy Plus Mini Kit (Qiagen, Valencia, Calif.). RNA will be eluted with 50 µL DEPC-treated water and quantified using a Nanoprop 1000 (Nanoprop Technologies, Wilmington, Del.). RNA will be reverse transcribed using random hexamers and Taqman reverse transcription reagents (Applied Biosystems, Foster City, Calif.). PCR reactions will be performed on cDNA samples using human specific β2 microglobulin primer probes (catalogue number 4310886E, Applied Biosystems, Foster City, Calif.). PCR will be performed using an ABI Prism 7900 HT Sequence Detection System (Applied Biosystems, Foster City, Calif.).

At the time of necropsy, whole blood will be collected, allowed to clot, placed into microcentrifuge tubes, and centrifuged at 2500 rpm for 15 minutes to separate serum from other blood components. Serum samples will then be analyzed using a VetAce Chemistry Analyzer (Alpha Wassermann Diagnostic Technologies, LLC, West Caldwell, N.J.).

Fixed kidney tissue will be embedded in paraffin wax, sectioned (5 µm-thick) and stained with hematoxylin/eosin (H&E) and Masson's Trichrome. The sections will then be scored for tubular injury (tubular necrosis, dilation, interstitial cellular infiltrate) and interstitial fibrosis (collagen deposition) using a scoring index ranging from 1 to 4 (1=minimal, 2=mild, 3=moderate, 4=severe). The evaluator will be blinded to the treatment group assignments.

It is expected that administration of human umbilical cord tissue-derived cells will result in a reduction in the overall content of tubular injury as assessed by histological evaluation.

EXAMPLE 12

Evaluation of the Renoprotective Efficacy of Local Human Umbilical Cord Tissue-Derived Cell Transplantation in a 5/6 Remnant Model of Chronic Kidney Disease The purpose of this prophetic example is to determine the renoprotective effects of local, subcapsular implantation of hUTC in a rodent model of chronic renal disease.

SD rats (n=30; 8 week-old, male) with an initial weight of 200-250 g will be used for these experiments. The rats will be anesthetized with an intraperitoneal injection (5 mg/kg) of a 4:1 solution of ketamine hydrochloride and xylazine hydrochloride. Kidney failure will be induced by a two-stage nephrectomy procedure. The upper and lower parts of the left kidney (two thirds of one kidney) will be resected using silk ligature while preserving the renal capsule. Ten days later, the right kidney will be removed, leaving approximately ⅙ of the total kidney mass (⅚ nephrectomy). Applying soft pressure with methylcellulose will stop bleeding, and the peritoneum and skin will be closed in layers with resorbable 4-O Vicryl sutures.

Five weeks after the ⅚-nephrectomy procedure, hUTC will be transplanted under the capsule of the remaining tissue of rats with kidney failure using fibrin gel matrix. Fibrinogen solution (1.0 mL) containing hUTC (60 million cells) and thrombin solution (1.0 mL) will be prepared. Rats will be anesthetized, and the remnant kidney will be exposed by a midline laparotomy. Through a syringe designed for simultaneous injection of the fibrin and thrombin solutions, 0.1 mL of the 1:1 (volume ratio) mixture of thrombin and fibrinogen solution containing cells will be injected into the subcapsular space through an 18-gauge hypodermic needle. As a control, ⅚ nephrectomized rats will be injected with fibrin matrix only.

Serum samples will be obtained on days 0 (prior to ⅚ nephrectomy) and on day 1 (day of cell transplantation), days 7, 14, 21, 28 and 35 (day of necropsy). Blood urea nitrogen and creatinine will be quantified using a VetAce Chemistry Analyzer (Alpha Wassermann Diagnostic Technologies, LLC, West Caldwell, N.J.).

Animals in all groups will be sacrificed five weeks post cell transplantation by carbon dioxide asphyxiation. Kidneys will be removed for histology and transcriptional analysis. Half of each kidney will be snap-frozen in liquid nitrogen for RT-PCR analysis. Messenger RNA will be isolated from the frozen kidney tissue by study coordinator and subjected to transcriptional analysis utilizing low-density microarray cards containing pro-fibrotic and inflammatory genes. The remaining corneal kidney section will be fixed in 10% neutral buffered formalin for downstream histological analysis.

Kidney tissue fixed for histology will be histologically processed, sectioned (5 µm-thick) and stained with hematoxylin/eosin. Tubular injury will be evaluated and scored by a veterinary pathology.

In this study, subcapsular transplantation of 6.0e6 hUTC embedded in fibrin is expected to slow the progression of renal injury in ⅚ nephrectomized rodents. It is expected that both serum creatinine and blood urea nitrogen values will be significantly reduced in the hUTC treated animals as compared to the control animals. In addition, histological injury assessment should reveal a reduction in tubular necrosis and tubular dilation in the treated animals. A reduction in the overall extent of inflammatory gene expression in hUTC treated rodent kidneys relative to control group kidneys is also expected to be observed.

What is claimed:

1. A method of treating a patient having a disease of or damage to at least one kidney, comprising administering to the patient a homogeneous population of cells obtained from human umbilical cord tissue in an amount effective to treat the disease or damage, wherein the umbilical cord tissue is substantially free of blood, and wherein the population of cells is capable of self-renewal and expansion in culture and has the potential to differentiate; does not produce CD31, CD34, CD117 or HLA-DR; and expresses, relative to a human fibroblast, mesenchymal stem cell, or iliac crest bone marrow cell, increased levels of interleukin 8 and reticulon 1.

2. The method of claim 1, wherein the population of cells expresses oxidized low density lipoprotein receptor 1, reticulon, chemokine receptor ligand 3, or granulocyte chemotactic protein 2.

3. The method of claim 1, wherein the population of cells expresses CD10, CD13, CD44, CD73, and CD90.

4. The method of claim 1, wherein the population of cells is administered by injection or infusion.

5. The method of claim 1, wherein the population of cells is administered encapsulated within an implantable device.

6. The method of claim 1, wherein the population of cells is administered by implantation of a matrix comprising the population of cells.

7. The method of claim 1, wherein the population of cells is administered with at least one other cell type.

8. The method of claim 7, wherein the at least one other cell type is administered simultaneously with, or before, or after, the population of cells obtained from human umbilical cord tissue.

9. The method of claim 1, wherein the population of cells is administered with at least one agent.

10. The method of claim 9, wherein the at least one agent is administered simultaneously with, before, or after administration of the population of cells obtained from human umbilical cord tissue.

11. The method of claim 1, wherein the population of cells exert a trophic effect on the kidney of the patient.

12. The method of claim 1, wherein the damage to the kidney is induced by age, trauma, toxin exposure, drug exposure, radiation exposure, oxidation, immune-complex deposition, or transplant rejection.

13. A method of treating a patient having a disease of or damage to at least one kidney, comprising administering to the patient a composition comprising a soluble cell fraction prepared from a homogeneous population of cells obtained from human umbilical cord tissue, wherein the umbilical cord tissue is substantially free of blood, and wherein the population of cells is capable of self-renewal and expansion in culture and has the potential to differentiate; does not produce CD31, CD34, CD117 or HLA-DR; and expresses, relative to a human fibroblast, mesenchymal stem cell, or iliac crest bone marrow cell increased levels of interleukin 8 and reticulon 1.

14. A method of treating a patient having a disease of or damage to at least one kidney, comprising administering to the patient a composition comprising a homogeneous population of cells obtained from human umbilical cord tissue and a lysate, extracellular matrix, or conditioned medium prepared from said homogeneous population of cells obtained from human umbilical cord tissue, wherein the umbilical cord tissue is substantially free of blood, and wherein the population of cells is capable of self-renewal and expansion in culture and has the potential to differentiate; does not produce CD31, CD34, CD117 or HLA-DR; and expresses, relative to a human fibroblast, mesenchymal stem cell, or iliac crest bone marrow cell increased levels of interleukin 8 and reticulon 1.

* * * * *

SEQUENCE LISTING

<160> NUMBER OF SEQ ID NOS: 10

<210> SEQ ID NO 1
<211> LENGTH: 22
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 1
gagaaatcca aagagcaaat gg                                              22

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agaatggaaa actggaatag g                                               21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tcttcgatgc ttcggattcc                                                 20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gaattctcgg aatctctgtt g                                               21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttacaagcag tgcagaaaac c                                               21

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agtaaacatt gaaaccacag cc                                              22

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 7
tctgcagctc tgtgtgaagg                                            20

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cttcaaaaac ttctccacaa cc                                         22

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cccacgccac gctctcc                                               17

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tcctgtcagt tggtgctcc                                             19
```